(12) United States Patent
Strand et al.

(10) Patent No.: US 8,080,145 B2
(45) Date of Patent: Dec. 20, 2011

(54) METHOD AND APPARATUS DETERMINING THE ISOELECTRIC POINT OF CHARGED ANALYTE

(75) Inventors: David Strand, Sherborn, MA (US); Dan M. Leatzow, Butte, MT (US)

(73) Assignee: Protasis Corporation, Marlborough, MA (US)

( * ) Notice: Subject to any disclaimer, the term of this patent is extended or adjusted under 35 U.S.C. 154(b) by 1458 days.

(21) Appl. No.: 10/542,493

(22) PCT Filed: Jan. 12, 2004

(86) PCT No.: PCT/US2004/000630

§ 371 (c)(1),
(2), (4) Date: Apr. 24, 2006

(87) PCT Pub. No.: WO2004/065937

PCT Pub. Date: Aug. 5, 2004

(65) Prior Publication Data

US 2007/0163884 A1    Jul. 19, 2007

Related U.S. Application Data

(60) Provisional application No. 60/440,105, filed on Jan. 15, 2003, provisional application No. 60/471,681, filed on May 15, 2003.

(51) Int. Cl.
*G01N 27/447* (2006.01)

(52) U.S. Cl. .................................. 204/459; 204/548

(58) Field of Classification Search .................. 204/548, 204/644, 450, 549, 550, 645, 451, 456, 459, 204/461, 610, 600, 601, 606
See application file for complete search history.

(56) References Cited

U.S. PATENT DOCUMENTS

| | | | | |
|---|---|---|---|---|
| 3,664,939 A | * | 5/1972 | Luner et al. | 204/548 |
| 4,666,855 A | * | 5/1987 | Yang et al. | 436/89 |
| 4,680,102 A | | 7/1987 | Ishiwatari | 204/299 R |
| 4,725,343 A | * | 2/1988 | Hjerten et al. | 204/548 |
| 5,110,434 A | * | 5/1992 | Zhu et al. | 204/451 |
| 5,298,143 A | | 3/1994 | Ivory et al. | 204/301 |
| 5,521,155 A | * | 5/1996 | Malabarba et al. | 514/8 |
| 6,277,258 B1 | * | 8/2001 | Ivory et al. | 204/450 |
| 6,284,115 B1 | | 9/2001 | Apffel | 204/518 |
| 6,613,508 B1 | * | 9/2003 | Ness et al. | 435/6 |
| 7,118,660 B2 | * | 10/2006 | Witt | 204/452 |
| 2001/0034435 A1 | | 10/2001 | Nochumson et al. | 536/23.1 |

OTHER PUBLICATIONS

Mazzeo et al. Capillary isoelectric focusing of proteins in uncoated fused-silica capillaries using polymeric additives, Anal. Chem. 1991, 63, 2852-2857.*

(Continued)

*Primary Examiner* — Alex Noguerola
*Assistant Examiner* — Gurpreet Kaur
(74) *Attorney, Agent, or Firm* — Banner & Witcoff, Ltd.

(57) ABSTRACT

Devices are provided for determining the isoelectric point of a charged analyte, comprising a titration chamber and an electrode chamber. The electrode chamber comprises at least two electrodes, for example, an electrode array. Either or both of the titration chamber and the electrode chamber may have a shaped geometry. The electrodes are operative, in conjunction with the shaped geometry of the chamber(s) where appropriate, to generate an electric field gradient in the titration chamber. Permeable material separates the titration chamber and the electrode chamber. A pH Sensor is located in the titration chamber for obtaining the pH of the first fluid. Certain preferred embodiments further include an analyte band detector for detecting the presence and optionally the location of a focused band of charged solute. Methods are provided for determining the isoelectric point of a charged analyte comprising introducing a carrier fluid comprising a Charge analyte into the titration chamber of a device as just described and applying an electric field gradient to focus the charged analyte into a focused band. The pH of the carrier fluid is incremented or adjusted to shift the location of the focused band of charged analyte, and the pH and location of the focused band of charged analyte are obtained for a plurality of locations and pH's and the isoelectric point is determined from such data.

20 Claims, 40 Drawing Sheets

OTHER PUBLICATIONS

Capillary isoelectric focusing with a Universal Concentration Gradient Imaging System Using a Charge-Coupled Photodiode Array, Anal. Chem. 1992, 64, 2934-2941.*

Ackers et al., "Determination of stoichiometry and equilibrium constants for reversibly associating systems by molecular sieve chromatography," *Proc. Nat. Acad. Sci. USA* 53: 342-349 (1965).

Koegler and Ivory, Field Gradient Focusing: A Novel Method for Protein Separation, *Biotechnol. Prog.*, 12:822-836 (1996).

International Search Report issued in PCT/US04/00630.

Written Opinion issued in PCT/US04/00630.

* cited by examiner

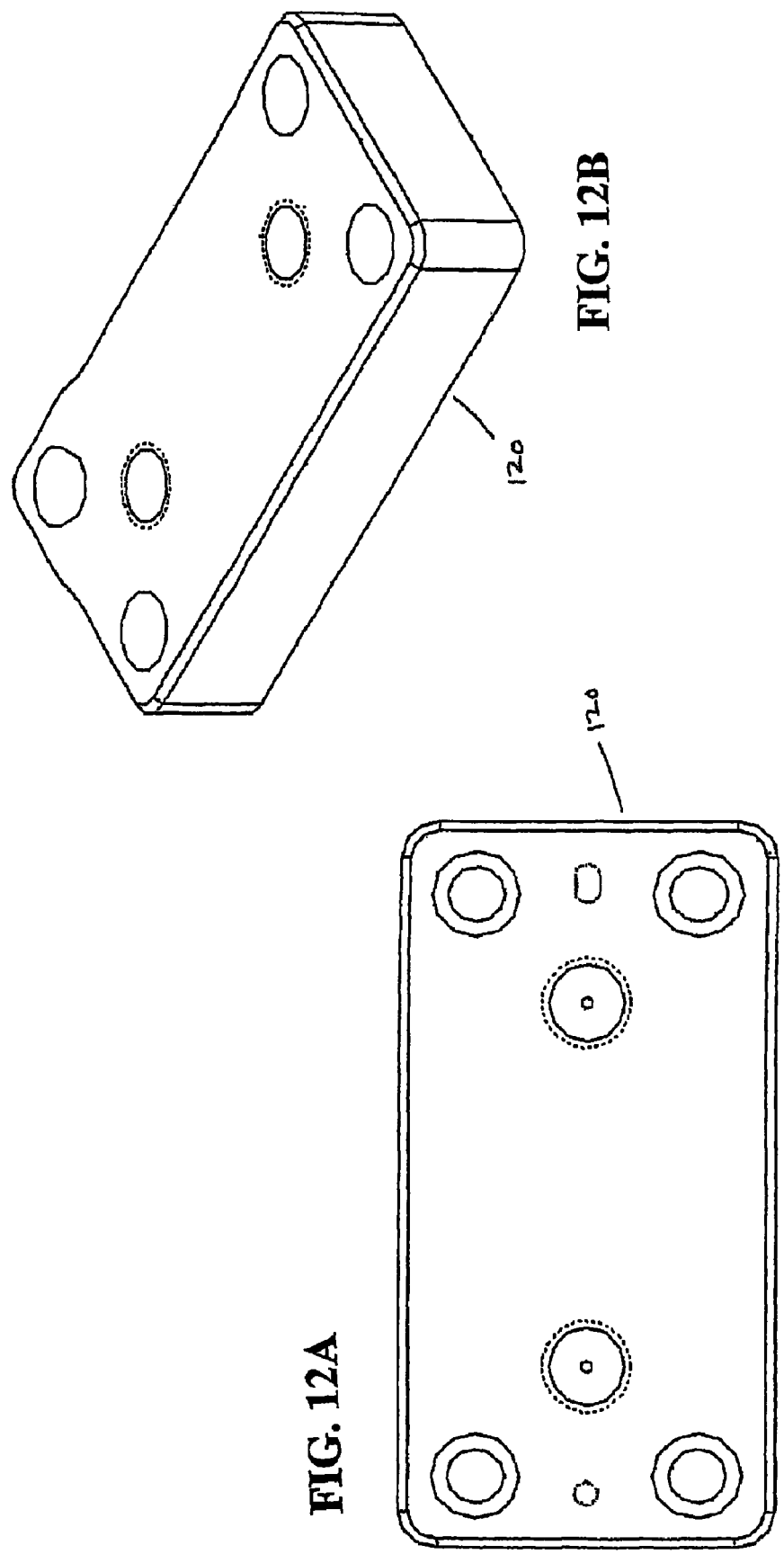

FIG. 40A
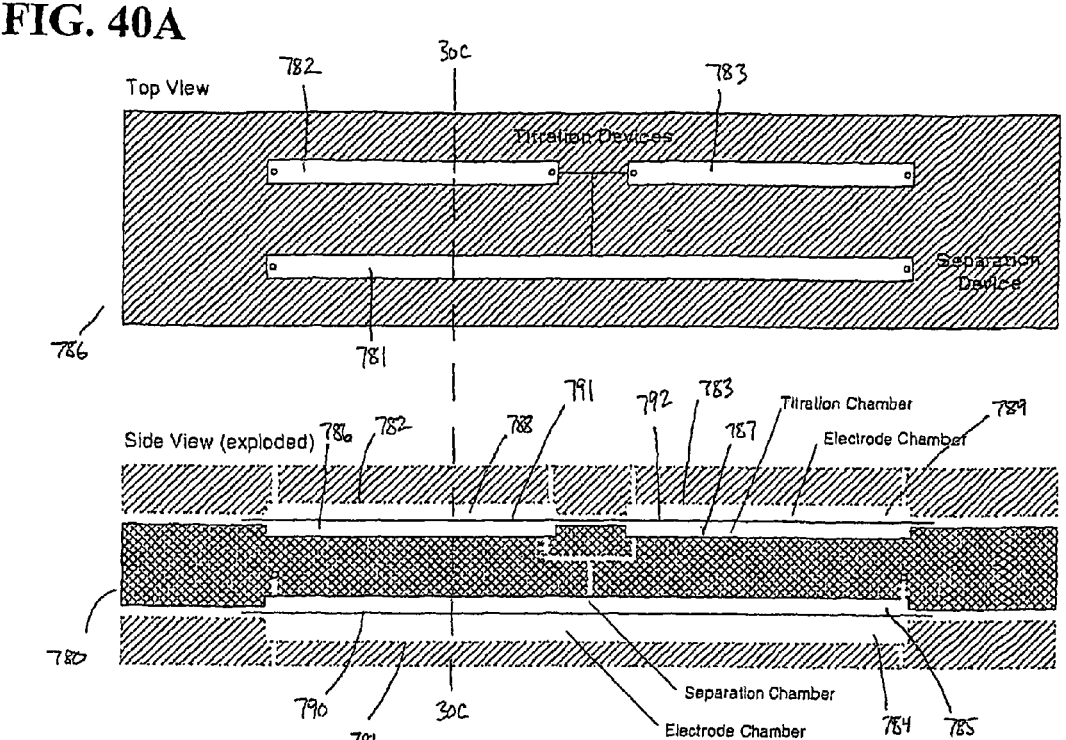
FIG. 40B
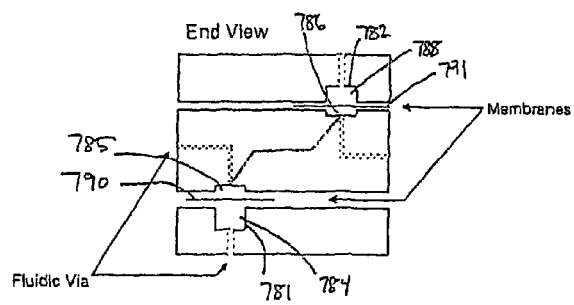
FIG. 40C

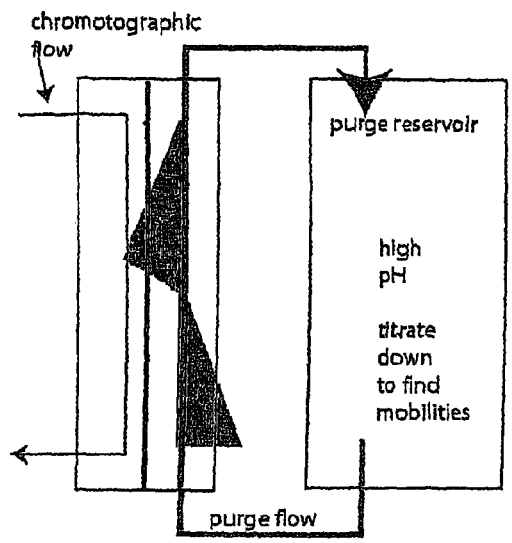
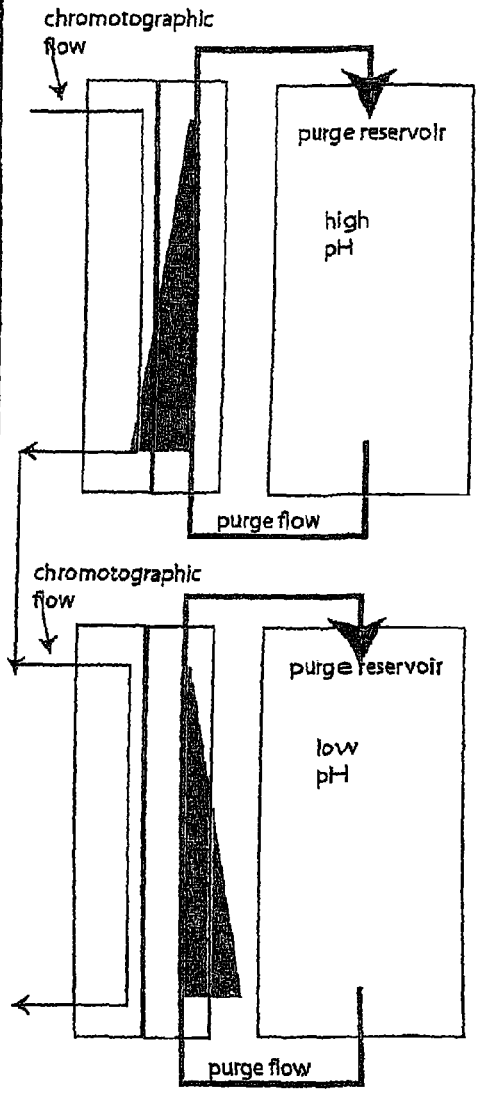
FIG. 41A  FIG. 41B

METHOD AND APPARATUS DETERMINING THE ISOELECTRIC POINT OF CHARGED ANALYTE

CROSS-REFERENCE TO RELATED APPLICATIONS

This application is a 35 U.S.C. §371 National Phase filing of PCT Application No. PCT/US04/000630 filed 12 Jan. 2004, which application claimed priority of the following commonly owned U.S. Provisional Patent Application Ser. No. 60/440,105, filed 15 Jan. 2003 and U.S. Ser. No. 60/471,681, filed 15 May 2003. The PCT application designated the United States and was published in the English language on 5 Aug. 2004 as WO 04/065937 A2.

RELATED APPLICATIONS

This application is related to commonly owned copending Provisional Application Ser. No. 60/440,105 filed Jan. 15, 2003, which is hereby incorporated by reference in its entirety for all purposes.

FIELD OF THE INVENTION

The present invention relates to methods and devices for determining the isoelectric point of an analyte.

BACKGROUND OF THE INVENTION

The isoelectric point is one of the qualities commonly used in the scientific community to characterize analytes. Many biomolecules (e.g., amino-acids, proteins, and peptides) have an isoelectric point. The isoelectric point (pI) of a molecule in a liquid is the pH value at which the molecule has a zero net charge. As the pH of a buffer in which the molecule resides approaches the molecule's pI, the net charge of the molecule approaches zero, which results in a diminishing electrophoretic mobility. Devices and methods for determining the isoelectric point of biomolecules and other analytes would therefore have significant commercial value, for example, in drug discovery and other pharmaceutical research, pharmaceutical and other chemical testing and production processes, and the like.

A need exists for new methods and devices for determining the isoelectric point of a charged analyte. A further need exists for simpler electrophoretic methods and devices that can effectively separate a mixture of charged analytes, e.g., a mixture of biomolecules, into its component analytes and to determine the isoelectric point of all or some of the component analytes. It is an object of the present invention to fulfill one or more of these needs and in certain preferred embodiments to provide further related advantages. From the following disclosure and the detailed description of certain preferred embodiments, additional objects of the invention and objects of certain preferred embodiments of the invention will be apparent to those skilled in the art, i.e., to those having skill and experience in this area of technology.

SUMMARY

In accordance with one aspect, devices for determining the isoelectric point of a charged analyte comprise a titration chamber (referred to in some instances as a first chamber) and an electrode array isolated from the titration chamber and operative to establish an electric field gradient in the titration chamber. The device includes a pH sensor positioned for exposure to liquid introduced into the titration chamber. Such liquid is referred to in some instances as a flowing liquid or as a carrier liquid. The term "liquid introduced into the titration chamber" is understood to mean liquid that is about to be introduced into, or liquid that already has been introduced into and remains in, or optionally has already exited from the titration chamber. Suitable pH sensors include, for example, various commercially available sensors, e.g., ion selective electrodes and the like. Other suitable pH sensors will be readily apparent to one skilled in the art, given the benefit of the present disclosure. The titration chamber has an inlet and an outlet for passing a fluid sample through the chamber, i.e., an inlet for introducing liquid into the chamber and an outlet for exiting liquid from the chamber. Typically, the titration chamber has a uniform cross-section flow channel. In other preferred embodiments, the titration chamber has a non-uniform cross-section flow channel. As used herein, "non-uniform" refers to a chamber that has a non-uniform cross-section, that is to say, the cross-sectional area of the chamber varies axially along the length of the chamber, length referring to the direction in which fluid flows through the separation chamber. For example, a non-uniform electrode chamber refers to an electrode chamber has a cross-section that varies axially along the length of the chamber in a direction parallel to the flow of fluid through the separation chamber. Such a chamber is at times referred to herein as "configured." In certain preferred embodiments, the device further comprises a second chamber (referred to in some instances as an electrode chamber) with a permeable material between the titration chamber and the electrode chamber. The electrode chamber has an inlet and an outlet for passing a fluid through the chamber and an electrode array operative to be energized to establish an electric field gradient in the first chamber through the permeable membrane. Optionally, the device further comprises an analyte band detector for detecting the presence of and optionally the location of a focused band of charged analyte.

In accordance with another aspect, devices for determining the isoelectric point of a charged analyte comprise a titration chamber (referred to in some instances as a first chamber) and at least two electrodes isolated from the titration chamber and operative to establish an electric field in the titration chamber. The device includes a pH sensor as disclosed above, positioned for exposure to liquid introduced into the titration chamber as described above. The titration chamber has an inlet and an outlet for passing a fluid sample through the chamber, i.e., an inlet for introducing liquid into the chamber and an outlet for exiting liquid from the chamber. The titration chamber has a non-uniform cross-section flow channel, that is to say, the cross-sectional area of the titration chamber varies axially along the chamber. The electrodes generate an electric field which is communicated to the titration chamber, where the non-uniformity of the titration chamber induces a gradient in the electric field. The titration chamber in certain preferred embodiments has a substantially uniform height (height here meaning the direction normal to the plane of the membrane) and a non-uniform or non-constant width (width here meaning the direction perpendicular to the overall direction of flow and parallel to the plane of the membrane). In other preferred embodiments, the titration chamber has a substantially uniform width and a varying or non-uniform height. Still other preferred embodiments employ a titration chamber of non-uniform width and non-uniform height. Other preferred embodiments include a titration chamber defined by one or more non-linear walls, for example, a series of faces or facets, some or all having non-uniform dimensions; or wherein the titration chamber has a curved cross-section, such as, for example, a half-circular cross-section, that varies axially, as, for example, a half-cone-shaped chamber. Other suitable titration chamber configurations will be readily apparent to those of skill in the art, given the benefit of the present disclosure.

In yet another aspect, devices for determining the isoelectric point of a charged analyte comprise a titration chamber (referred to in some instances as a first chamber). The device includes a pH sensor as disclosed above, positioned for exposure to liquid introduced into the titration chamber as described above. The titration chamber has an inlet and an outlet for passing a fluid sample through the chamber, i.e., an inlet for introducing liquid into the chamber and an outlet for exiting liquid from the chamber. The titration chamber has a uniform cross-section flow channel, that is to say, the cross-sectional area of the titration chamber does not vary axially along the chamber. Devices in accordance with this aspect further comprises a second chamber (referred to in some instances as an electrode chamber or a titration electrode chamber) with a permeable material between the titration chamber and the electrode chamber. The electrode chamber has an inlet and an outlet for passing a fluid through the chamber and at least two electrodes operative to be energized to establish an electric field in the titration chamber through the permeable membrane. The electrode chamber is configured or non-uniform, that is, the electrode chamber has a non-uniform cross-section flow channel. The non-uniformity of the electrode chamber will itself create a gradient in the electric field, the shape of which will in turn be affected by the non-uniformity of the sample channel.

In certain preferred embodiments, the electrode chamber in these embodiments may have a substantially uniform depth (depth here meaning the direction normal to the plane of the membrane) and non-uniform width. In other preferred embodiments, the permeable membrane separating the electrode chamber and the titration chamber is substantially planar. The electrode chamber in these embodiments may have a substantially uniform depth (depth here meaning the direction normal to the plane of the membrane) and non-uniform width, or in the alternative may have a substantially uniform width and a varying or non-uniform depth. Other preferred electrode chamber configurations for such embodiments include an electrode chamber defined by one or more non-linear walls, for example, a series of faces or facets, some or all having non-uniform dimensions; or wherein the electrode chamber has a curved cross-section, such as, for example, a half-circular cross-section, that varies axially, as, for example, a half-cone-shaped chamber. Other suitable configurations of the electrode chamber will be readily apparent to those of skill in the art, given the benefit of the present disclosure. Optionally, the device further comprises an analyte band detector for detecting the presence of and optionally the location of a focused band of charged analyte.

In accordance with another aspect, devices for determining the isoelectric point of a charged analyte comprising a titration chamber, electrodes, and a titration reservoir are provided. The device is operative to generate an electric field gradient in the titration chamber in any of the ways described above, i.e., by a configured titration chamber, a configured electrode chamber, an electrode array, or any combination of the three. The titration reservoir is in communication with the titration chamber. This may be fluid communication, for example, such that liquid from the titration reservoir could mix with a liquid that is in the titration chamber or entering or about to enter the titration chamber, or could in certain preferred embodiments refer to the ability of a fluid contained in the titration reservoir to pass ions into or out of the titration chamber, such that ions could be exchanged between liquid from the titration reservoir and a liquid that is in the titration chamber or entering or about to enter the titration chamber. The reservoir may be provided in any suitable form or format, for example, as one or more remote container of acid, base and/or buffer having fluid communication with the titration chamber via suitable conduit, e.g., tubing or the like. In other preferred embodiments in the form of a system on a chip or the like, the reservoir may be one or more voids in a chip substrate, with fluid pathways, such as microfluidic channels etched into the substrate to the titration chamber, optionally with valves or other fluid flow controls. In other such embodiments, the reservoir may be provided as one or more components attached to or otherwise carried by or integrated with a substrate, housing or the like of a device in accordance with the present disclosure, such components being preferred in some cases as a "component-on-board." Typically the reservoir will have a fluid capacity sufficient for one or more titrations in accordance with the methods disclosed here. Typically, one or more pumps or other devices or components are provided for pumping, preferably for metering the acid, base or buffer into the titration chamber so as to achieve good control of pH adjustment or incrementation.

In accordance with another aspect, devices for determining the isoelectric point of a charged analyte comprising a titration chamber and electrodes as just described. The devices further comprise an analyte band detector and a processor. The devices are operative to generate an electric field gradient in the titration chamber in any of the ways described above, i.e., by a configured titration chamber, a configured electrode chamber, an electrode array, or any combination of the three. The analyte band detector is operative to generate positional signals corresponding to positions of a band of analyte in the titration chamber. The processor is operative to receive positional signals from the analyte band detector and to determine the magnitude of position change of an analyte band in the titration chamber in the course of titration. The analyte band detector can comprise a single detector or a plurality of detectors, for example an array of detectors arranged along at least a portion of the titration chamber. Suitable detectors include potentiometric, conductive, optical, electromagnetic, electrochemical, and the like. In certain preferred embodiments that are in the form of a system on a chip, the detector can be embedded or otherwise integrated into the chip, e.g., into a substrate layer.

In accordance with another aspect, devices for determining the isoelectric point of a charged analyte comprise a titration chamber and at least two electrodes in accordance with the aspects described above and an analyte band detector operative to generate a signal corresponding to detection of a band of analyte downstream of an electric field gradient in the titration chamber. As used herein, "downstream" is defined as being with reference to a flow of liquid through the titration chamber, i.e., liquid flowing into the chamber through the inlet and out of the chamber through the outlet. Suitable analyte band detectors include those described above. Other suitable analyte band detectors will be readily apparent to those skilled in the art, given the benefit of the present disclosure.

In accordance with another aspect, devices for determining the isoelectric point of a charged analyte comprise a titration chamber and electrodes as described in any of the above aspects or embodiments. This aspect further comprises a separation chamber and separation electrodes that are unique from the titration chamber and electrodes associated with it. The separation chamber may itself be configured, that is, may comprise a non-uniform cross-section flow channel, or instead may comprise a uniform cross-section flow channel paired with a non-uniform cross-section flow channel electrode chamber or an electrode array, or may comprise any combination of the three, such that an electric field gradient is established in the separation chamber. In certain preferred embodiments, the separation chamber comprises molecular sieve to shift the location of a stationary focused band of charged analyte in the separation chamber for a given set of focusing process parameters. The separation chamber and the titration chamber are in fluid communication, for example, such that a charged analyte could be separated from other charged analytes in the separation chamber and could be eluted into the titration chamber, where the isoelectric point of the charged analyte could be determined in accordance with the methods and devices disclosed herein.

In operation under suitable focusing process parameters, the chambers of certain preferred embodiments of the devices disclosed above typically are filled with liquid sufficiently electrically conductive to establish an electric field gradient in the separation chamber when the electrodes are energized. The permeable membrane between the chambers preferably is operative to establish selective communication between the titration chamber and the electrode chamber, at least sufficiently to provide selective mass transport between the chambers, or between the electrodes and the titration chamber where no electrode chamber is present; the permeable membrane also prevents the target analyte from passing to the electrode chamber or to the electrodes. The chambers typically are elongate and partly or wholly overlying one another in their longitudinal dimension. The electrodes of the electrode chamber are operative to establish an electric field in the electrode chamber, which is communicated through the porous conductive membrane to the titration chamber. In those embodiments described here that comprise a porous membrane, the membrane is at least conductive in that it does not prevent the electric field in the chamber and it is porous in the sense that it is permeable to buffer species or the like without allowing contact of the target analyte with the electrodes. In certain embodiments, the membrane does not substantially affect the electric field generated by the electrodes and does not affect the electric field experienced by the separation chamber. A gradient is induced in the electric field by the non-uniformity of the sample channel, the non-uniformity of the electrode chamber, the electrode array, or any combination of the three. Where an electrode array is present, the electrode array typically includes a plurality of electrodes arranged along the length of the electrode chamber, with each electrode optionally capable of being individually controlled, i.e., energized at a level selected independently of the energization level of other electrodes of the array. In certain preferred embodiments the electrode array is operative to generate an electric field gradient profile which can be dynamically controlled.

Preferred embodiments of the devices disclosed here are suitable for focusing charged analytes and for separating mixtures of charged analytes, including analytes such as DNA or other naturally occurring or artificial biomacromolecules having the same or similar charge to mass ratios and electrophoretic mobilities, i.e., the same or similar magnitude of charge per unit length of the biomacromolecules (or charge per unit of molecular weight) at a given pH of the buffer solution in which the sample is presented, and then for determining the isoelectric point of one or more of the charged analytes. Such embodiments typically incorporate molecular sieve in the titration, separation or both chambers as is further described below.

In accordance with a method aspect, devices in accordance with any of those disclosed immediately above are employed. A fluid sample is flowed through the titration chamber. An electric field gradient is established and maintained (with or without adjustment or change during the focusing process) in the focusing chamber using the electrodes of any of the above-disclosed devices. Where an electrode array is employed, optionally the electrodes of the array are individually monitored and controlled. Optionally, for example, the voltage applied to each electrode is controlled by a computer-controlled circuit board or suitable processor or the like in operative connection to a suitable voltage source. Charged analyte is focused in a flowing liquid in an electric field gradient to form in the flowing liquid a stationary focused band of the charged analyte at a position in the electric field gradient. Certain preferred embodiments of such methods simultaneously focus multiple charged analytes from a fluid sample. Each of the multiple analytes is focused in the chamber at a stable position spatially separated from the focusing location of others of the analytes. In certain applications, one or more of such stationary focused bands may comprise multiple analytes. Once the charged analyte is focused, the pH of the fluid flowing through the titration chamber is incremented at least once by an amount sufficient to change the position of the focused band of the charged analyte within the electric field gradient, and pH and corresponding position data for the charged analyte are obtained, comprising determining the pH of the flowing liquid and the corresponding position of the focused band of the charged analyte at a plurality of band positions within the electric field gradient. The isoelectric point of the charged analyte is determined based on the pH and corresponding position data. It should be understood that the titration chamber in which the analyte is focused for titration is, in certain preferred embodiments, the separation chamber employed for initial isolation of the analyte from or in the fluid sample. In other preferred embodiments, an analyte is first isolated in a separation chamber, e.g., in a chamber in accordance with those described above or in the separation chamber of a dynamic field gradient focusing (DFGF) device, as disclosed in U.S. Pat. No. 6,277,258, incorporated herein in its entirety for all purposes.

In certain preferred embodiments, the isoelectric point is determined by extrapolation. In other preferred embodiments, the pH is incremented to a plurality of pH values above the isoelectric point of the charged analyte and to a plurality of pH values below the isoelectric point of the charged analyte; the isoelectric point can then be determined by interpolation. In yet other preferred embodiments, the pH is incremented from above the isoelectric point downward until an upper bracketing pH is reached at which the analyte elutes; the pH is incremented upward from below the isoelectric point until a lower bracketing pH is reached at which the analyte elutes; the upper bracketing pH and the lower bracketing pH are obtained, and the isoelectric point is determined by averaging the upper and lower bracketing pH values. Optionally, an analyte band detector at the outlet of the titration chamber notes the time at which the band of charged analyte elutes, and the pH of the carrier at the time of elution is obtained. In certain preferred embodiments, this is accomplished by fractioning the analyte into two portions and running the portions into two separate such devices. In another preferred embodiment, the analyte is run in one direction on a first device, the analyte elutes out of the device at which point the pH is rapidly adjusted to a suitable pH for the subsequent run, and the analyte is introduced into a second such device and run in the opposite direction. In yet another preferred embodiment, the sample is run on a single such device, first in one direction and then, having had the pH rapidly adjusted to a suitable pH for the subsequent run, the analyte is introduced back into the device and run in the other direction. As used in this discussion, direction refers to the adjustment of the pH of the fluid during the run, i.e. from a lower to a higher pH or from a higher to a lower pH. Other suitable designs for systems for analyzing an analyte in multiple directions will be readily apparent to those of ordinary skill in the art, given the benefit of the present disclosure.

It should be understood that reference above and elsewhere herein to a fluid sample passed through the flow or focusing chamber can mean a single fluid sample passed one or more times through the chamber or a series of two or more fluid samples passed in turn through the chamber. Similarly, it can mean a fluid whose composition changes over time during processing.

In certain preferred embodiments, devices and methods in accordance with aspects provided here can further include integration of detection and pH signals with software to allow automation and computer optimization of solute loading, separation, elution, focusing and pI determination steps.

BRIEF DESCRIPTION OF THE DRAWINGS

The foregoing aspects and many of the attendant advantages of the methods and devices disclosed here will be appreciated with reference to the following detailed description, when taken in conjunction with the accompanying drawings, wherein:

FIG. 3—NOT BEING USED

FIG. 4—NOT BEING USED

FIG. 8—NOT BEING USED;

FIG. 9—NOT BEING USED;

FIG. 11-16 are attached and shown.

FIG. 17—NOT BEING USED;

FIG. 18—NOT BEING USED;

FIG. 19—NOT BEING USED;

FIG. 40A is a top view, in cross-section, of a device incorporating a system in accordance with another preferred embodiment;

FIG. 40B is an exploded side view, in cross-section, of the device of FIG. 30A;

FIG. 40C is an exploded end-view of the device of FIGS. 30A and 30B;

FIGS. 41A and B are flow charts illustrating methods in accordance with preferred embodiments of the invention.

DETAILED DESCRIPTION

Figure 1:
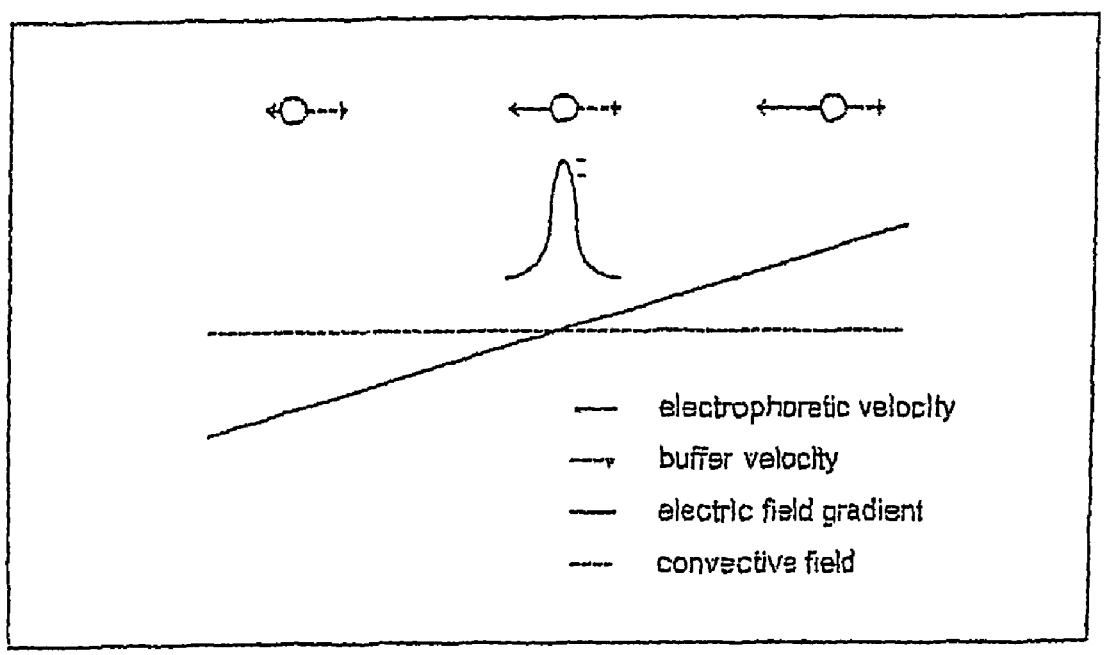
FIG. 1 is a graph illustrating the principles of EFGF.

Unless otherwise indicated or unless otherwise clear from the context in which it is described, aspects or features described below of preferred embodiments should be understood to be disclosed generally for use with other embodiments of the devices and methods disclosed herein. Also, in accordance with traditional patent usage, the use of the indefinite article "a" in the following is intended to mean one or more than one, that is, at least one, unless otherwise clear from the context in which it is used. It should be understood that the mere usage of the phrase "at least one" or like phrases, in certain instances, is alone not an indication that usages of the individual article "a" in other instances means only one.

Without wishing to be bound by theory of operation, it currently is understood that the electric field gradient serves to provide a counter force to the force of the fluid flowing through the titration chamber so as to hold a charged analyte in a stable location, typically as a band of charged analyte, for a given pH. Stable means that the location of the band of focused charged analyte remains substantially constant as long as the conditions of the analysis remain substantially constant. As the pH of the fluid in which the charged analyte is focused, i.e. the carrier liquid, is incremented, the net or apparent charge of the charged analyte changes, thus causing the charged analyte to shift in the electric field gradient. As used herein, incrementing the pH refers to changing the pH of the fluid in a fashion that permits the focused band of charged analyte to move to a new location and either remain focused as it shifts or refocus at the new location, i.e. the incrementation is at a rate to permit such. If the pH is incremented to a pH close enough to the isoelectric point of the charged analyte, the analyte takes on a net or apparent charge of zero, or takes on a net or effective charge of low enough magnitude that the electric field gradient cannot exert sufficient force to hold or focus the analyte in the titration chamber, and the analyte "washes out" or elutes from the titration chamber. By determining the pH and the location of the focused band of charged analyte within the titration chamber, the isoelectric point can be determined.

"Electrophoretic device" as used herein refers to any device which employs opposing hydrodynamic and electrophoretic forces to affect the location of a charged analyte within the device. As used here, the term "focus" and other forms of that word are used generally to mean concentrating a desired analyte (i.e., a target species dissolved or suspended in a sample fluid) in the separation chamber of an electrophoresis device in accordance with the above disclosure. It will be readily understood that this may inherently include separating that analyte from the carrier fluid and often from one or more other analytes that do not concentrate at the same location in the chamber under the focusing process parameters employed. The term "separating" and other forms of that word, unless otherwise indicated by context or the like, generally are used to describe the result of the present invention, optionally employing molecular sieve in the separation chamber, i.e., separating the desired analyte from the sample fluid and, in certain preferred embodiments, from other analytes. As noted above, the electrode chamber includes electrodes for generating a focusing electric field gradient. The separation chamber is in electrical communication and mass or ionic communication with the electrode, chamber through the porous, conductive membrane. "Communication" or "electrical communication" as used herein refers to the ability of the electric field that is generated by the electrode array to be transferred, or to have an effect, within the separation chamber, and may be by any means which accomplishes this. The porous membrane retains analytes in the separation chamber and is permeable to certain molecules such that the electrode chamber and separation chamber are in communication as noted above. Generally, an eluant is introduced into and flows through the separation chamber containing the charged analyte. The eluant flow is opposed to the direction of electrophoretic migration of the analyte.

As noted above, a "configured" chamber refers to a chamber, i.e. a separation chamber or an electrode chamber, that has a non-uniform cross-section flow channel, that is to say, the cross-sectional area of the separation chamber varies axially along the chamber. It will of course be apparent to one skilled in the art that such configuration or non-uniformity occurs within the electric field, that is to say, the electric field generated by the electrodes encompasses a portion of the separation chamber that is configured.

Reference throughout this disclosure to focusing an analyte in a flowing liquid and incrementing the pH of the flowing liquid is meant to include both (1) employing the same chamber to initially focus the analyte and then to determine the pI of the charged analyte and (2) prefocusing the analyte, for example, in a DFGF device as described in U.S. Pat. No. 6,277,258, and then injecting or otherwise feeding the concentrated analyte into a titration chamber for pI determination in accordance with the methods and devices disclosed here. Reference to a flowing liquid or to the flowing liquid is understood to include the possibility that the composition of the flowing liquid may be changed. Certainly in accordance with devices and methods disclosed herein, it is understood that an acid, base, or buffer fluid or the like may be added or subtracted to or from the flowing liquid during the incrementation or adjustment portion of the process.

A charged analyte, as used herein, refers to an analyte that exhibits a net or apparent charge of a magnitude greater than zero at at least some pH and that exhibits a net charge of zero at at least one pH. Preferably, the charged analyte will exhibit a net charge of zero magnitude at a single pH (i.e. will have an isoelectric point) and will exhibit a positive net or apparent charge at pH's below the isoelectric point and will exhibit a negative net or apparent charge at pH's above the isoelectric point. Typical charged analytes include charged biological analytes and biomacromolecules such as proteins, peptides, oligonucleotides, polynucleotides, hormones, biomarkers, DNA, RNA and the like. As described below, mixtures of these charged analytes can be separated and focused prior to pI determination, by electrophoretic devices and methods including those described, for example by the devices and methods found in U.S. Pat. Nos. 5,298,143 and 6,277,258, in U.S. application Ser. No. 60/440,150, entitled "Devices and Methods for Focusing Analytes in an Electric Field Gradient," filed on 15 Jan. 200; U.S. application Ser. No. 60/440,105, entitled "Method and Apparatus for Determining the Isoelectric Point of a Charged Analyte," filed on 15 Jan. 2003 U.S. application Ser. No. 60/430,493, entitled "Electrophoresis Device, System and Method for Sample Management and Hyphenation of Analytical Instruments," filed on Dec. 2, 2002; U.S. application Ser. No. 60/447,997, entitled "Electrophoresis Device, System and Method for Sample Management and Hyphenation of Analytical Instruments," filed on Feb. 18, 2003; U.S. application Ser. No. 60/471,616, entitled "Electrophoresis Device, System and Method for Sample Management and Hyphenation of Analytical Instruments," filed on May 19, 2003; U.S. application Ser. No. 60/471,681, entitled "Method and Apparatus for Determining the Isoelectric Point of a Charged Analyte," filed on May 19, 2003; U.S. application Ser. No. 60/471,597, entitled "Devices and Methods for Focusing Analytes in an Electric Field Gradient," filed on May 19, 2003; U.S. application Ser. No. 60/471,623, entitled "Electrophoresis Devices and Methods for Focusing Charged Analytes," filed on May 19, 2003; or in U.S. application Ser. No. 60/471,595, entitled "Electrophoresis Devices and Methods for Focusing Charged Analytes," filed on May 19, 2003, all of which are incorporated herein in their entirety for any and all purposes.

The carrier fluid in certain preferred embodiments comprises a flowing liquid, which may comprise water or advantageously may comprise buffer. Generally, a higher concentration of buffer stabilizes the sample, for example a protein sample, and therefore avoids precipitation. However, in general, high ionic strength means high conductivity of the buffer, which increases the heat generation and power consumption and sets a limit for the highest suitable electric field strength. Typical field strengths include, for example, 180 to 300 v/cm. Suitable liquids will be readily apparent to those of ordinary skill in the art, given the benefits of the present disclosure.

In accordance with certain preferred embodiments, a fluid gradient can be used to provide increased separation between different bands of analytes during the separation and focusing of the charged analyte(s). As used here, fluid gradient refers to variation in the composition of the fluid flowing through the separation chamber during the separation of the analytes. For example, in a separation using two solvents, A and B, the separation may begin with 100% solvent A. As the separation progresses, the amount of solvent B can be increased, e.g., linearly, step-wise, logarithmically, etc., such that the solvent composition introduced into the chamber includes both A and B. Typically, the amount of each solvent in the solvent gradient is controlled by varying the amount of solvent introduced into the chamber. The solvents typically are introduced into the chamber through one or more pumps or other suitable devices. In certain embodiments, it may be necessary to provide a mixing chamber so that the solvent can be mixed prior to introduction of the solvents into the devices described here. In certain embodiments, the solvent gradients are computer controlled to provide high precision for the separations. One skilled in the art, given the benefit of this disclosure, will be able to select suitable solvent gradients for use in the devices and methods disclosed here. Of course, it will be recognized that, upon completing the separation and focusing portion of the analysis, the fluid composition must be held constant, other than the incrementation of the pH, during the determination of the isoelectric point.

In certain preferred embodiments, a hydrodynamic force is provided for flowing the liquid, generally provided by a pump. Typical flow rates range, e.g., from 0.1 to 10 L/min. for analytical applications, and, e.g., from 10 to 200 L/min. for preparative applications. The flow rate is chosen to provide the desired focusing, and where appropriate the desired separation, such that the hydrodynamic force counters the electric field gradient at a position between the weakest and the strongest part of the electric field. In this fashion, the analyte will be retained within the first chamber. Factors that affect the flow rate include the viscosity of the first liquid, strength of the electric field gradient, net charge of the analyte, and the like. Suitable flow rates will depend, therefore, in part upon the electric field gradient that is utilized. Suitable flow rates can be readily determined by routine trial and error.

In accordance with certain preferred embodiments, solvents that are used in the devices and methods disclosed here may be degassed prior to separation of analytes. Without wishing to be bound by any particular scientific theory, it is believed that dissolved gases in the solvents can affect the reproducibility of the flow rates of the solvents. Thus, to achieve constant and reproducible flow rates, it may be necessary to remove at least some of the dissolved gases from any solvents prior to introduction of the solvents into the devices described here. The person of ordinary skill in the art, given the benefit of this disclosure, will be able to select suitable techniques for degassing the solvents including, but not limited to, vacuum filtration of the solvents, e.g., filtration through a fritted funnel, bubbling of inert gases, such as, for example, argon and nitrogen, through the solvents, and the like.

In accordance with certain preferred embodiments, a solvent gradient may be used to provide increased separation between different bands of analytes. As used here, solvent gradient refers to variation in the composition of the solvent during the separation of the analytes. For example, in a separation using two solvents, A and B, the separation may begin with 100% solvent A. As the separation progresses, the amount of solvent B can be increased, e.g., linearly, step-wise, logarithmically, etc., such that the solvent composition introduced into the chamber includes a mixture of both solvents A and B. Typically, the amount of each solvent in the solvent gradient is controlled by varying the amount of solvent introduced into the chamber. The solvents typically are introduced into the chamber through one or more pumps or other suitable devices. In certain embodiments, it may be necessary to provide a mixing chamber so that the solvents can be mixed prior to introduction of the solvents into the devices described here. In certain embodiments, the solvent gradients are computer controlled to provide high precision for the separations. One skilled in the art, given the benefit of this disclosure, will be able to select suitable solvent gradients for use in the devices and methods disclosed here.

In accordance with certain preferred embodiments, lipids may be introduced either in the solvent or in the loaded sample. Without wishing to be bound by any particular scientific theory, lipids typically are either hydrophobic, having only nonpolar groups, or can be amphipathic, having both polar and nonpolar groups. In embodiments where one or more analytes are uncharged, it may be necessary to introduce an amphipathic lipid into the sample. Again without wishing to be bound by any particular scientific theory, the nonpolar group of the lipid can associate with one or more uncharged analytes, e.g., through hydrophobic interactions, hydrogen bonding, dipolar interactions, and the like, while the polar group of the lipid typically remains free to provide an overall charge to the lipid-analyte complex. In certain embodiments, lipids are selected from phosphatidic acid, phospholipids and glycerophospholipids such as, for example, phosphatidylcholine, phosphatidylethanolamine, phosphatidylserine, cardiolipin, phosphatidylglycerol, phosphatidylinositol, and the like. In other embodiments, the lipids may include ether glycerophospholipids, cerebrosides, sphingolipids, and the like. One skilled in the art, given the benefit of this disclosure, will be able to select these and other suitable lipids for use in the devices and methods disclosed here.

In accordance with certain embodiments, the lipids can form micelles that may associate with one or more analytes. Without wishing to be bound by any particular scientific theory, because many lipids include a nonpolar group and a polar group, e.g., amphipathic lipids, when the lipids are placed into an aqueous environment, the lipids typically spontaneously associate with each such that the polar groups are positioned outward towards aqueous solvent and the nonpolar groups are positioned inward away from aqueous solvent. Typically, it is necessary to provide the lipids in a sufficient amount, e.g., a critical micelle concentration (CMC), such that micelles can spontaneously form. That is, when the lipids are present at concentration below the CMC, the predominate form is individual free lipids. When the lipids are present at a concentration greater than or equal to the CMC, the predominant form is micelles. Suitable CMC concentrations will be readily selected by those skilled in the art, given the benefit of this disclosure, and the CMC concentration typically depends on the type of lipid selected.

In accordance with certain preferred embodiments, the lipids may form vesicles, e.g., unilamellar (large unilamellar vesicles (LUVs), small unilamellar vesicles (SUVs)) or multilamellar vesicles. Such vesicles are typically characterized as including one or more bilayers formed when the nonpolar groups of the lipids associate with each other. Suitable methods for preparing vesicles will be readily selected by those skilled in the art, given the benefit of this disclosure, and include but are not limited to extrusion, sonication/extrusion, and the like.

In accordance with other preferred embodiments, in the presence of lipids, micelles and/or vesicles, the analytes can partition between the bulk solvent and the lipids, micelles and/or vesicles. For example, one or more portions of the analyte molecule can interact with a portion of the lipid to form an analyte-lipid complex. Typically an equilibrium is established between free analyte and analyte complexed with lipid. It may be possible to favor this equilibrium depending on the nature of the analyte and the nature of the lipid selected. For example, it is possible to favor the lipid-analyte complex by adding lipid in amounts far in excess of the analyte concentration to shift the equilibrium to form additional analyte-lipid complex. When the predominant form in solution is analyte-lipid complex, the position at which the analyte is focused typically will differ from the position at which free analyte will focus. In certain embodiments, lipid-analyte complex will focus at a position substantially less than free analyte, i.e., under similar separation conditions, free analyte typically can migrate further than analyte-lipid complex. To determine the pI of an analyte, because the native pI of the analyte may be masked or altered by the lipid, it may be necessary to dissociate the analyte-lipid complex to provide free analyte and free lipid. The free analyte can be isolated, and a pI determination may then be performed on the free analyte using the methods disclosed here or other suitable methods readily selected by the person of ordinary skill in the art. One skilled in the art given the benefit of this disclosure will be able to select suitable lipids and suitable amounts of the lipids to favor, or disfavor, lipid-analyte complexes.

In accordance with certain preferred embodiments, lipids, micelles and/or vesicles can be added to a sample to separate analytes of similar molecular weights and/or similar overall charges. Without wishing to by bound by any particular scientific theory, in many instances analytes having similar molecular weights and/or similar overall charges will be difficult to separate from each other and typically will appear as a single band. To facilitate separation of such analytes, lipids, micelles and vesicles can be used. Because there is likely to be some differences between the analytes, e.g., differences in hydrophobicity, composition, three-dimensional structure, surface area properties, and the like, the analytes should interact differently with the lipids, micelles and/or vesicles. For example, if one of the analytes includes a large number of hydrophobic groups, such as amino acids leucine, alanine, valine, etc., then it is possible that these hydrophobic groups will interact more frequently with hydrophobic lipids to reduce entropically disfavored interactions with polar bulk solvent. Accordingly, the use of lipids, micelles and/or vesicles can provide for the ability to baseline separate two or more analytes that behave similarly in the devices provided here. As discussed above, to determine the pI of an analyte, it may be necessary to dissociate the analyte-lipid complex to provide free analyte and free lipid. The free analyte can be isolated, and a pI determination may then be performed on the free analyte using the methods disclosed here or other suitable methods readily selected by the person of ordinary skill in the art.

In accordance with other preferred embodiments, the lipids, micelles and/or vesicles can be used to focus an analyte in a different position than in the absence of any lipids, vesicles or micelles. This result may be desirable for low molecular weight analytes or highly charged analytes, for example, which are difficult to focus at or near a sampling port. For example, without wishing to be bound by any particular scientific theory, it may be difficult to prevent certain analytes from migrating out of the device due to small size, high charge, etc. In the presence of lipids, micelles and vesicles, the analyte-lipid complex can increase the effective size of the analyte, which can reduce its rate of migration in the devices disclosed here. After removal of the analyte-lipid complex, e.g., through an exit port or a sampling port, the analyte-lipid complex can be dissociated and the analyte can be isolated using methods routinely used by the person of ordinary skill in the art, e.g., centrifugation, dialysis, etc. As discussed above, to determine the pI of an analyte, a pI determination may be performed on the free analyte using the methods disclosed here or other suitable methods readily selected by the person of ordinary skill in the art. It will be within the ability of the person of ordinary skill in the art, given the benefit of this disclosure, to select and use suitable lipids, micelles and vesicles, and suitable amounts of these compounds, to control migration of one or more analytes in the devices disclosed here.

In accordance with yet other preferred embodiments, the lipids, micelles and/or vesicles can be used to separate two or more analytes having very similar migration behavior, e.g. two or more analytes that focus at the same position within the chamber. This result may be desirable for samples comprising two or more analytes that are similarly charged, for example, and difficult to separate from each other. For example, without wishing to be bound by any particular scientific theory, it may be difficult to separate analytes having similar charges even if those analytes have different physical or physico-chemical properties, e.g., different hydrophobicities, secondary or tertiary structures, etc. In the presence of lipids, micelles and vesicles, the analyte-lipid complex can increase the effective size of the analyte, which, in certain embodiments, can reduce its rate of migration in the devices disclosed here. Because different analytes may interact differently with the lipids, due to the differences in the physical properties of the analytes, for example, it may be possible to favor the lipid-analyte complex for one analyte and favor free analyte for another analyte so that the two analytes may be separated from each other. After removal of the analyte-lipid complex, e.g., through an exit port or a sampling port, the analyte-lipid complex can be dissociated and the analyte can be isolated using methods routinely used by the person of ordinary skill in the art, e.g., centrifugation, dialysis, etc. As discussed above, to determine the pI of an analyte, a pI determination may be performed on the free analyte using the methods disclosed here or other suitable methods readily selected by the person of ordinary skill in the art. It will be within the ability of the person of ordinary skill in the art, given the benefit of this disclosure, to select and use suitable lipids, micelles and vesicles, and suitable amounts of these compounds, to control migration of one or more analytes in the devices disclosed here.

Certain preferred embodiments include an analyte band detector operative to generate positional signals corresponding to positions of a band of analyte in the titration chamber or operative to generate a signal corresponding to detection of a band of analyte downstream of an electric field gradient in the titration chamber. In certain preferred embodiments, the analyte band detector is located at or just after the titration chamber outlet and is capable of detecting the band of analyte as it elutes from the titration chamber when the pH of the liquid approaches the isoelectric point. In other preferred embodiments, the analyte band detector is located to detect a band of focused analyte within the titration chamber itself, for example by being located within the titration chamber or by being capable of detecting a focused charged band of analyte through a portion of the detector, for example, one or more transparent windows or walls of the titration chamber. Suitable analyte band detectors include, for example, potentiometric detectors, optical detectors such as, e.g., UV-Visible detectors, refractive index detectors, absorption detectors and the like, or electromagnetic detectors, such as capacitive detectors or Hall effect detectors, conductivity detectors, and the like. Optionally, the analyte band detector can be located externally of the titration chamber, wherein the titration chamber comprises walls of viewing ports that are substantially transparent to the detection means. In other words, certain of the walls of the titration chamber permit a sufficient amount of light at a wavelength of interest, that is at a wavelength in which the band of analyte exhibits different optical properties such as absorption, refraction, fluorescence or phosphorescence from the flowing liquid, such that the presence or absence of a band of analyte can be determined. Optionally, the transparent walls or viewing ports are of sufficient length to permit detection across the length of the titration chamber, in particular across the length of the effective electric field within the chamber, such that the location of an analyte peak within the chamber can be determined. In certain preferred embodiments, such as for example where the focused band of charged analyte is visibly different in color or transparency form the flowing liquid, visual observation serves as the analyte band detector. In such embodiments, the operator can note the presence and location of a band of analyte. Other suitable analyte band detectors and configurations will be readily apparent to those of ordinary skill in the art, given the benefit of the present disclosure.

In certain preferred embodiments, devices as disclosed herein comprise a processor operative to receive positional signals from the analyte band detector and to determine the magnitude of position change of an analyte band in the titration chamber in the course of titration. Optionally, the devices include circuitry for extrapolating the pH value at which the focused charged band of analyte elutes from the titration chamber. In certain preferred embodiments, suitable means, for example a freestanding PC or a dedicated processor, perhaps located on-board the device, are provided to receive electronic signals from the analyte band detector. In the course of one or more incremental adjustments of the pH, the processor receives electronic signals from the analyte band detector corresponding to the new position of the analyte band within the titration chamber. As described above, at the isoelectric point the analyte will be substantially uncharged and the band of analyte will be eluted from the titration chamber by the hydrodynamic force of the flowing liquid. Moreover, as the pH is incremented, the net charge of the analyte increases or decreases in magnitude, causing the analyte band to stabilize at different locations along the electric field gradient in the titration chamber. Thus, providing two or more band positions corresponding to known pH values allows for simple extrapolation of the pH at which the analyte would exhibit substantially zero net charge. For example, as the magnitude of the net charge of the analyte approaches zero, the analyte will focus in portions of the electric field gradient of increasing strength; the electric field strength must be higher to compensate for the lower attraction of the analyte brought on by the lowering of the magnitude of the net charge of the analyte in order to counter the hydrodynamic and other forces acting on the analyte. From two or more band positions corresponding to known pH values, the pH at which the analyte reaches various positions in the electric field gradient, for example the pH at which the analyte focuses in the strongest part of the electric field gradient or the pH at which the analyte elutes from the electric field gradient, can be extrapolated. As can be seen, the position of the band of analyte in the chamber is dependant upon the balance of the strength and shape of the electric field gradient, the magnitude of net charge of the analyte, which is pH-dependant, and the hydrodynamic forces, which are typically held constant, acting in the opposite direction of the electromobility forces.

Electrophoresis devices described herein, unless otherwise indicated, are suitable for use both to determine the isoelectric point of a charged analyte and for the optional initial separation and focusing of the charged analyte(s). Such devices are operative to perform electric field gradient focusing (EFGF), employing a counter-balance of chromatographic flow against electromigration to create high resolution, free-solution separation and focusing functionality for a broad range of analytes in buffer systems, including simple buffer systems. Such devices comprise a first chamber, which will be either the titration chamber or the separation chamber (or may function as both the separation and titration chamber where the initial separation and focusing is performed in the same device that the isoelectric point titration is performed) as a focusing chamber and optionally an electrode chamber, which may be uniform or may be non-uniform, separated from the separation chamber by a porous or conductive membrane, e.g., a suitably functionalized dialysis membrane, Nafion® or other ion exchange membrane, which in certain preferred embodiments is substantially planar in configuration. Electrodes are positioned proximate the electrode chamber, i.e., in or near the non-uniform electrode chamber such that the electrode chamber is operative to establish an electric field gradient, which is communicated to the titration/separation chamber. As used herein, the term "titration/separation chamber" is used to refer to either or both of the titration chamber and the optional separation chamber where such exists as a separate chamber. The membrane is effective to pass electrical current and electrolyte ions (e.g., tris-phosphate buffer ions), but not the analyte, i.e., not the target molecule of interest being focused or concentrated in the separation chamber or having its isoelectric point determined in the titration chamber. Certain preferred embodiments of the electrophoresis devices disclosed here are operative to capture and concentrate a sample, as well as route (i.e., release) the sample from the chamber, and have applicability to processes in biotechnology, pharmaceutical or other scientific research and development areas as well as industrial production and testing applications. Certain preferred embodiments of the electrophoresis devices disclosed here provide a dynamic platform for preconcentration and routing of target solutes for subsequent analysis, and can serve as a sample preparation tool. Certain preferred embodiments of the electrophoresis devices disclosed here are substantially planar in configuration, the conductive, porous membrane being substantially flat with the sample flow channel above and the electrode chamber below.

Figure 2:
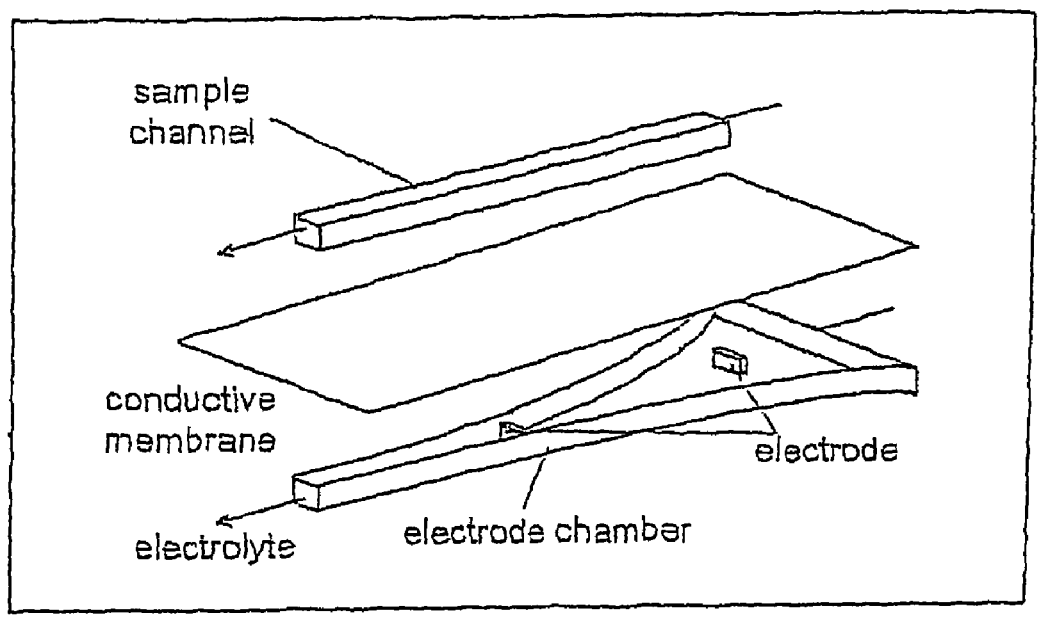
FIG. 2 is an exploded view of an exemplary device.

In certain preferred embodiments the porous, conductive membrane is substantially planar. The electrode chamber is non-uniform axially, that is to say, the cross-section of the electrode chamber varies along the axial length of the channel, such that a gradient is established in an electric field that is generated by the electric field in the electrode chamber and communicated into the titration/separation channel. The electrode channel in certain preferred embodiments has a substantially uniform depth (depth here meaning the direction normal to the plane of the membrane) and a non-uniform or non-constant width (width here meaning the direction perpendicular to the overall direction of flow and parallel to the plane of the membrane). In other preferred embodiments, the electrode chamber has a substantially uniform width and a non-uniform depth. In yet other preferred embodiments, the width and the depth are both non-linear, and may include side walls and a bottom wall that are each nonlinear in the same fashion or to differing degrees, multiple facets that are each non-linear to the same or different degrees, or may form a cone-like shape wherein the walls are curved in a direction normal to the axial direction and non-linear in the axial direction. Combinations of these are also possible. As discussed further below, it will be within the ability of those skilled in this technology area, given the benefit of this disclosure, to employ suitable separation channel geometry, sample flowrate, sample loading, as well as field strength in the electrode chamber to achieve good separation resolution in a short processing or "focusing" time. FIG. 2 is an exploded view of an exemplary device with an electrode pair, as well as the representative orientation of device components. The arrow heads indicated the direction of buffer flow. The electric field gradient would cause solute to migrate in the opposite direction to buffer flow.

Figures 7A, 7B, 7C:
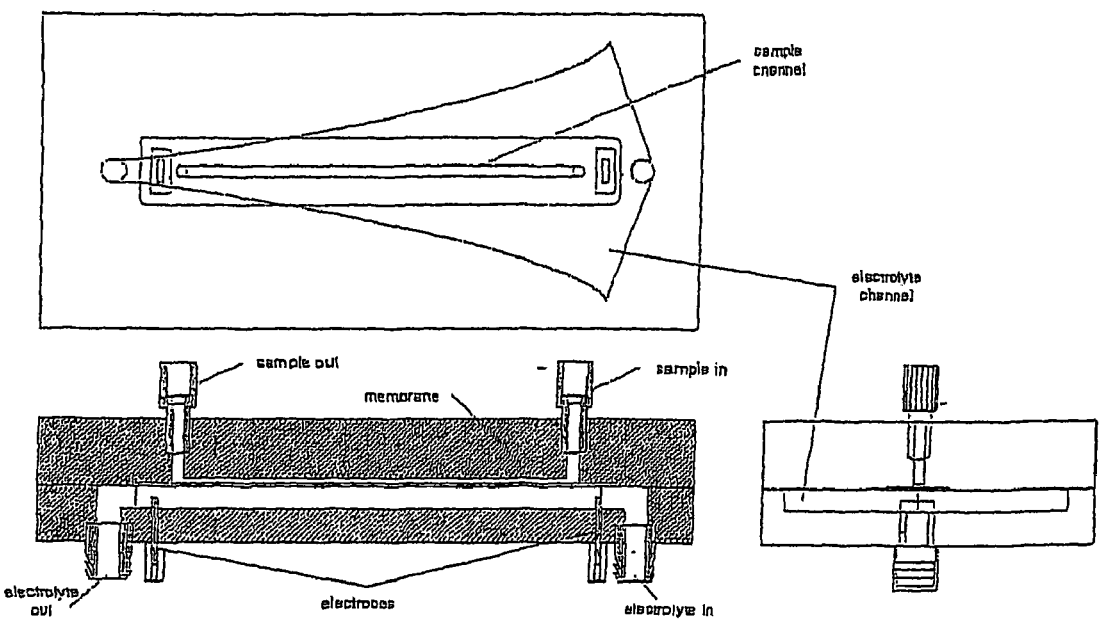
FIG. 7A-C are top views, a cross sectional side view, and a cross-sectional end view, respectively, of an exemplary device.
Figure 10:
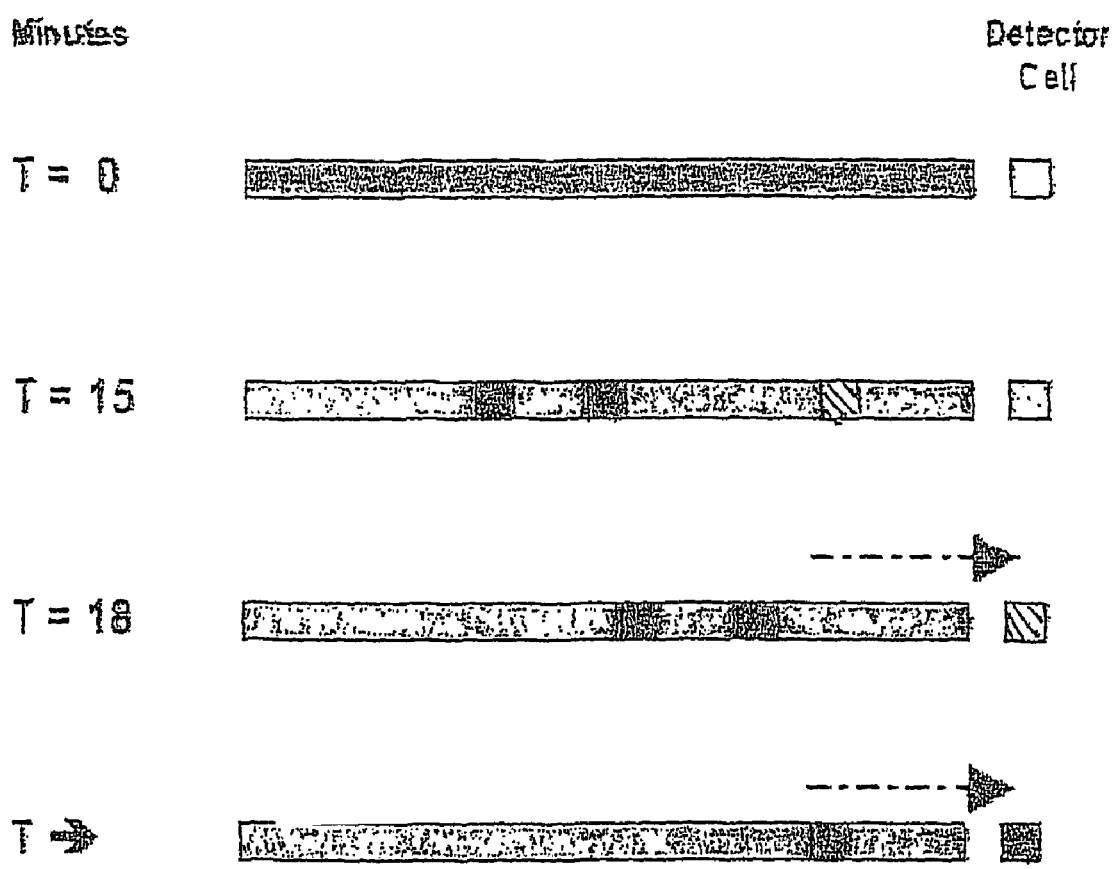
FIG. 10 is a series of images showing focused bands being eluted from an exemplary separation chamber.
Figure 11B:
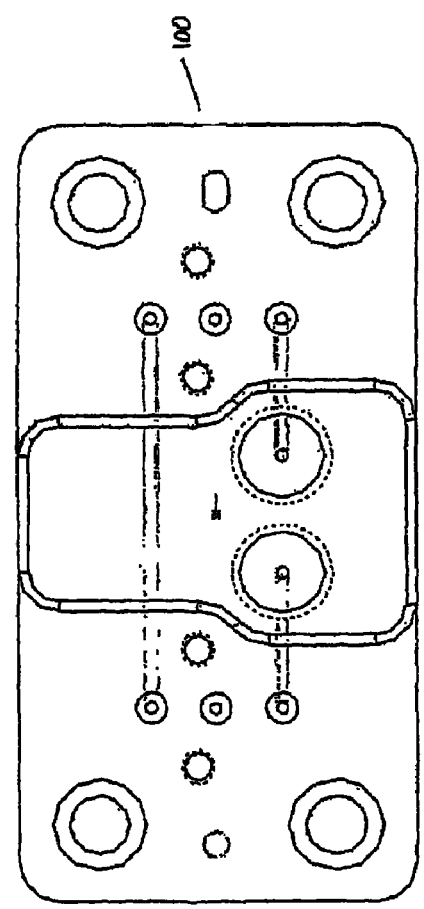
Figure 11A:
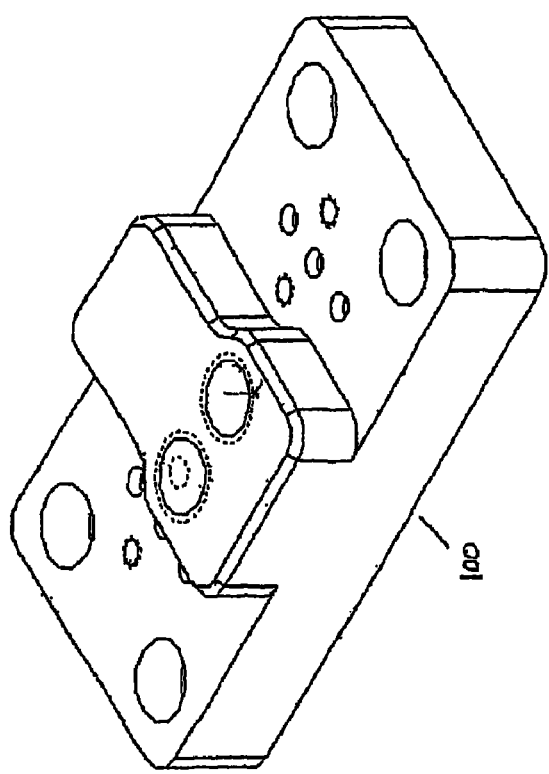
Figure 13B:
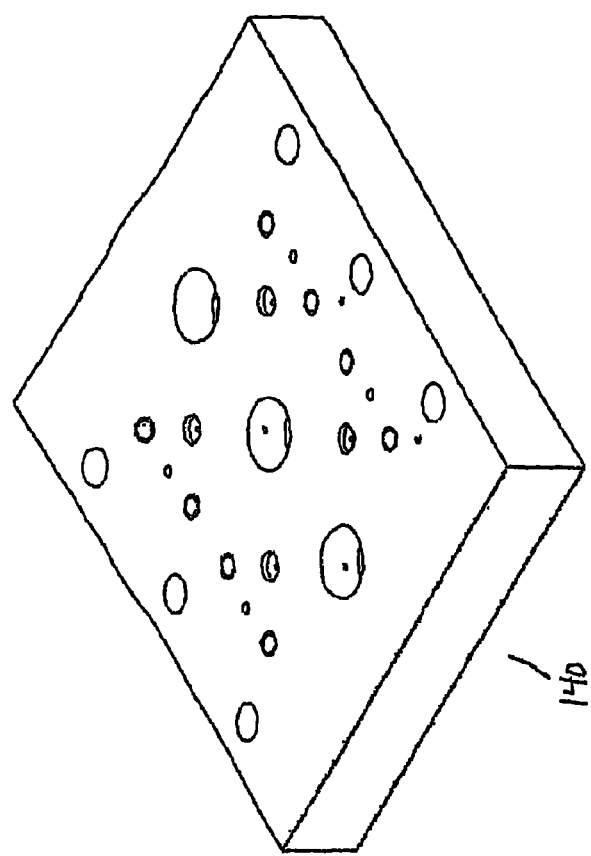
Figure 13A:
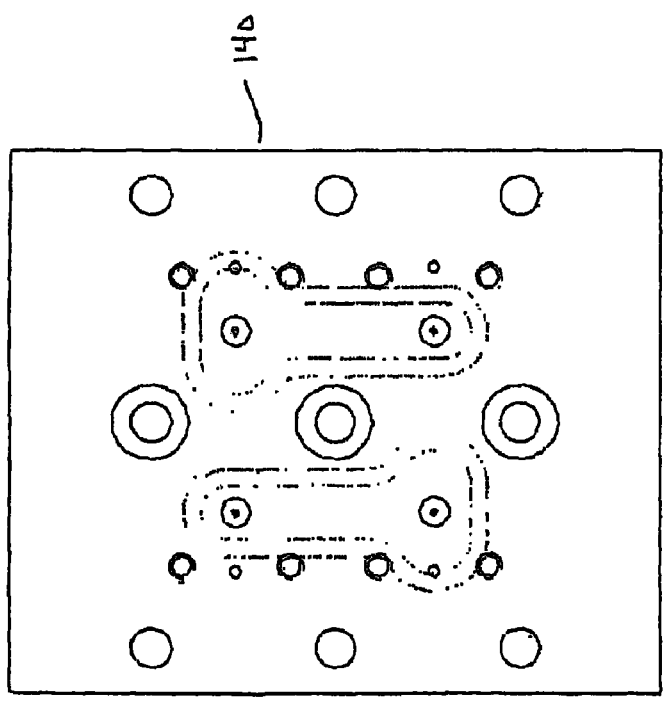
Figure 14:
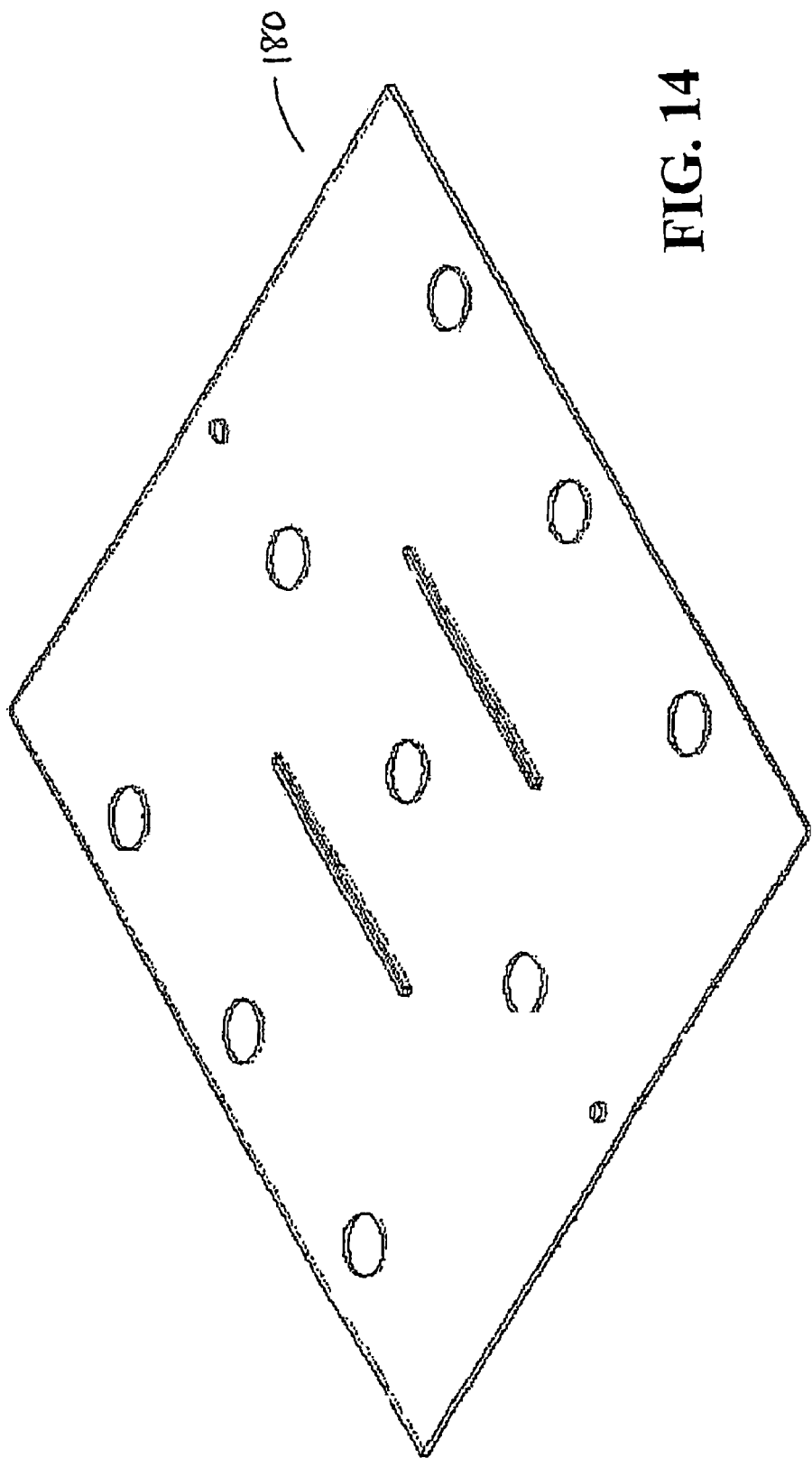
Figure 15B:
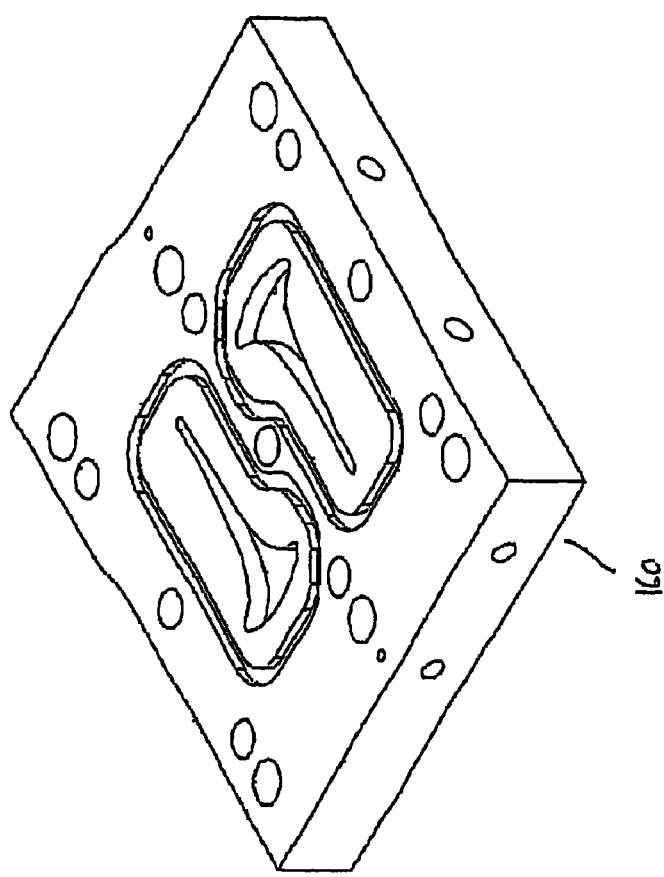
Figure 15A:
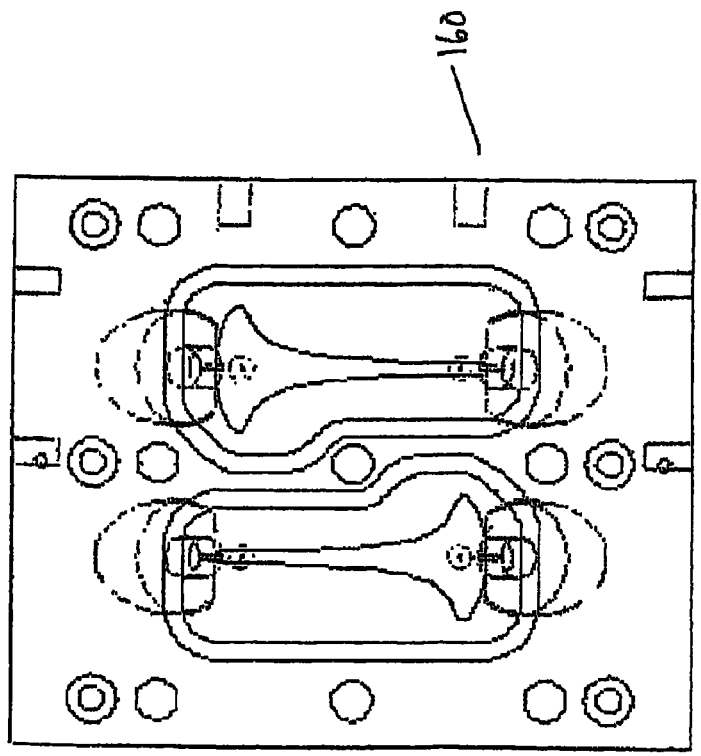
Figure 16:
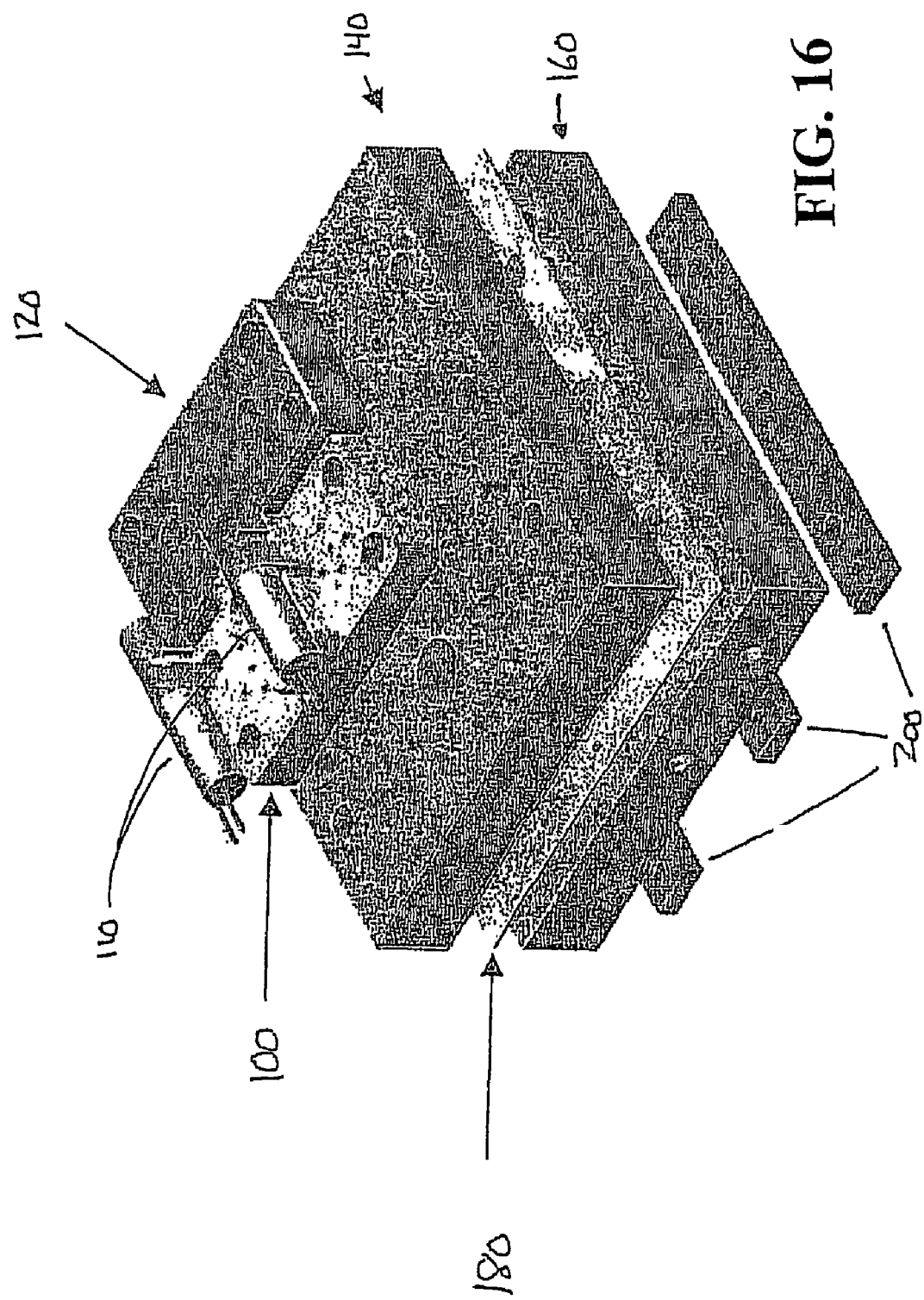

An exemplary configuration for certain of the devices and methods disclosed here is illustrated in FIG. 7, which has a uniform titration chamber and a non-uniform electrode chamber. Since the cross section of the electrode chamber is significantly larger than the titration chamber, the field gradient is primarily determined by the shape of the electrode chamber. Electrolyte sweeps through the electrode chamber to remove electrolysis products and joule heat. The titration chamber may be packed with a chromatographic media to stabilize convective perturbations. The device is seen to be an assembly of three functional layers including the sample focusing channel (upper most layer), the "conductive" membrane, and the electrode chamber (lower most layer). The two chamber layers may be fabricated from common plastics (e.g., acrylic or PEEK with TEFLON AF or quartz components) to allow visualization of the separation processes, however chemical compatibility will be a consideration in material selection. The electrodes, housed in the lower layer, are single electrode elements, typically consisting of either gold or platinum metal to prevent hydrolysis-induced breakdown. Trade-offs in the focusing systems have been observed in balancing the operational range and resolution against the ability to dissipate heat.

In other preferred embodiments, the porous, conductive membrane need not be planar. The electrode chamber in these embodiments is non-uniform in width and substantially uniform in depth. The side walls in certain preferred embodiments may be linear and nonparallel, or in other preferred embodiments one or both side walls is non-linear, for example, hyperbolic in shape. Other suitable configurations for the electrode chamber will be readily apparent to those of ordinary skill in the art, given the benefit of the present disclosure.

The titration/separation chamber is typically a uniform cross-section flow channel or chamber, but may in certain preferred embodiments be non-uniform and can comprise any of the configurations described above for the electrode chambers.

In still other preferred embodiments, the device comprises a titration/separation chamber separated from a non-uniform electrode chamber by a porous, conductive membrane. The electrode chamber comprises an electrode array. The titration/separation chamber typically is located alongside or adjacent the electrode chamber. In certain preferred embodiments, the titration/separation chamber may be partially or completely located within the electrode chamber, as, for example, a chamber enclosed partially or completely by the membrane and located within the electrode chamber. For example, the electrode chamber may be substantially conical, with the titration/separation chamber located entirely within the electrode chamber and separated from the electrode chamber by a tubular membrane, such as, for example, dialysis membrane tubing. The electrode array, typically positioned proximate or within the electrode chamber, is operative to generate an electric field gradient in the electrode chamber which is then further affected by the non-uniformity of the electrode chamber. The electrode chamber and the separation chamber may be of any of the configurations described above.

In other preferred embodiments, the titration/separation chamber is non-uniform axially, that is to say, the cross-section of the titration/separation chamber varies along the axial length of the channel, such that a gradient is established in an electric field that is generated in the titration/separation chamber by the electric field in the electrode chamber. The titration/separation channel in certain preferred embodiments has a substantially uniform height (height here meaning the direction normal to the plane of the membrane) and a non-uniform or non-constant width (width here meaning the direction perpendicular to the overall direction of flow and parallel to the plane of the membrane). In other preferred embodiments, the titration/separation channel has a substantially uniform width and a non-uniform height. In yet other preferred embodiments, the width and the height are both non-linear, and may include side walls and a top wall that are each nonlinear in the same fashion or to differing degrees, multiple facets that are each non-linear to the same or different degrees, or may form a cone-like shape wherein the walls are curved in a direction normal to the axial direction and non-linear in the axial direction. Combinations of these are also possible. As discussed further below, it will be within the ability of those skilled in this technology area, given the benefit of this disclosure, to employ suitable titration/separation channel geometry, sample flowrate, sample loading, as well as field strength in the electrode chamber to achieve good separation resolution in a short processing or "focusing" time.

The electrode chamber in these embodiments is preferably a uniform cross-section flow channel or chamber. In other preferred embodiments, the electrode chamber non-uniform and can comprise any of the electrode chamber embodiments described herein In yet other embodiments, the titration chamber comprises a chamber with an inlet for receiving a flowing liquid into the chamber and an outlet for exiting the flowing liquid from the chamber. In certain preferred embodiments, the electric field gradient is established in the titration chamber by a plurality of electrodes, for example two or more electrodes, e.g., an electrode array comprising more than two electrodes, such as fifty electrodes arranged linearly, located within or adjacent the titration chamber. In other embodiments, a plurality of electrodes is located outside of and alongside the titration chamber, and the titration chamber is in electric communication with the electrode array. In other words, the external electrode array generates an electric field gradient that is transported or transferred to the interior of the titration chamber. In certain preferred embodiments, the titration chamber comprises a porous tube with two electrodes. In other preferred embodiments, the titration chamber is located adjacent to a second chamber that comprises electrodes, for example two or more electrodes, including an electrode array, e.g. an electrode array comprising a plurality of electrodes such as, for example, fifty electrodes arranged linearly, with the two chambers separated by a permeable material, such that buffer ions of a second liquid contained in the second chamber can pass through the permeable material into the first chamber while the analyte of interest, and optionally macromolecules in general, cannot pass through the permeable material. An electric field in the titration chamber is generated by the electrodes, and the gradient is established either by the non-uniformity of the titration chamber, the non-uniformity of the electrode chamber, the electrode array as described in greater detail below, or any combination of the three.

In certain preferred embodiments, the titration chamber is a configured chamber, that is, the titration chamber has a non-uniform cross-section flow channel as described above. In other preferred embodiments, the electrode chamber is non-uniform. The non-uniformity of either of these channels will function to create a gradient in an otherwise uniform electric field, as for example might be generated by two electrodes located at each end of either of the chambers. In yet other preferred embodiments, the electric field gradient in the titration chamber is generated by any combination of a configured titration chamber, a configured electrode chamber, or an electrode array. Other suitable configurations for generating an electric field gradient in the titration chamber will be readily apparent to those skilled in the art, given the benefit of the present disclosure.

Certain preferred embodiments of the electrophoretic devices comprise a layered assembly. The sample channel and the electrode chamber are separated by a porous membrane. The sample channel is a conduit, which may have a shaped geometry, where sample peaks are loaded, held and off-loaded or eluted. The electrode chamber also may have a shaped geometry and has at least one built-in electrode pair, where there is one anode and one cathode. Where an electrode pair is used, at least one of the titration chamber and electrode chamber must be configured, that is, have a shaped geometry. Application of a DC voltage to the electrodes results in an electric field, with an intensity inversely proportional to the combined sample channel and electrode chamber cross-section at a given point. The electric field strength will vary along the axis of flow. To generate a linear electric field gradient, the combined chambers typically will have a hyperbolic shape, but nonlinear fields are possible by selecting the appropriate combined chamber geometry. The magnitude or slope of the field gradient may be manipulated by adjusting the voltage applied to the electrodes. The porous membrane must conductive for the passage of small ionic species and electrical current, thereby communicating the electric field to the sample channel. The pore size of the membrane is such that all molecules designated as samples will be retained in the sample chamber. A buffer system typically is required for the device to maintain stable pH and provide sufficient conductivity to carry the electrical current throughout the fluidic passages of the electrode chamber and sample channel. Typical operating parameters of an apparatus of this type with a 1-inch chamber are shown in Table 1:

| | |
|---|---|
| Sample Amount | 10 micrograms total load |
| Focusing Time | 10 minutes |
| PH Range | 3-9, programmable |
| Temp. Range | 10-25° C. |
| Number of Electrodes | 2 |
| Eluent Flowrate | 1 µL/min. |
| Buffer Flowrate | 1 mL/min. |
| Maximum Voltage | 350 Volts |
| Maximum Current | 45 mA |
| Maximum Field Strength | 200 Volts/cm |

In certain preferred embodiments, the focused analytes can be eluted from the electrophoretic focusing device through one or more separation ports positioned midway along the separation chamber, typically between the inlet port and the outlet port. Basically, the desired analyte can be focused to a region of the chamber from which the analyte can be eluted through a port. Analytes can be eluted from the separation chamber by electric field, pressure, vacuum, or other motive force.

In certain preferred embodiments, a pair of electrodes or optionally an array of electrodes is utilized to generate the electric field, with a gradient arising by means of the configuration of the titration/separation chamber, optionally in conjunction with a configured electrode chamber and/or electrode array, as described above. In such embodiments, the configuration of the separation chamber and/or the electrode chamber is itself subject to dynamic control, either by the user or by computer control. Such embodiments employ, for example, movable or pivotable walls such that the shape and size of the chamber can be altered during the course of a focusing run to provide dynamic control over the strength and/or shape of the electric field gradient.

Where the separation chamber configuration is dynamic, the gradient in the hydrodynamic force is advantageously subject to dynamic control, providing still more flexibility to the separation methods available. Suitable configurations employing dynamically-controlled chamber configurations will be readily apparent to one skilled in the art, given the benefit of the present disclosure.

In still other preferred embodiments, the electrophoretic devices comprise a titration/separation chamber and two or more electrodes separated from the chamber by a material operative to generate an electric field in the separation chamber, wherein the non-uniformity of the separation chamber is operative to establish a gradient in an electric field generated in the separation chamber by electrodes and to generate a gradient in the hydrodynamic force along the separation chamber. In certain preferred embodiments, the separation chamber is a tube with electrodes plated on the interior surface of the tube and coated with a porous, conductive coating membrane. The porous coating is chosen such that it allows small molecules such as buffer ions to pass but prohibits molecules of the size of the analytes from passing through and contacting the electrodes. In other preferred embodiments, the separation chamber comprises a porous tube with electrodes plated on the exterior of the tube. The porous tube is likewise chosen to be porous to small molecules and to prohibit passage of molecules of the size of the analyte(s). Of course, some means must be present to generate a gradient in the electric field. Such a gradient can be generated by either or both of an electrode array and a non-uniform titration/separation chamber in accordance with embodiments described herein. Other suitable configurations of devices that lack an electrode chamber will be readily apparent to those of skill in the art, given the benefit of the present disclosure.

The titration/separation chamber in any of the above embodiments can either be an open channel or can be packed with a media, such as a gel or granular packing, to reduce the convective dispersion and help maintain sharp peaks. In certain preferred embodiments, the titration/separation chamber contains a fluid medium. Suitable fluid media include simple fluids such as, for example, buffered water. Also included are complex fluids, for example, a water/acetonitrile/methanol mixture, or polymer solutions such as, for example, linear polyacrylamide, polyvinyl alcohol, methyl cellulose solutions and the like. The fluid media in certain preferred embodiments further comprises a chromatography support medium or packing. Suitable packings can be of any size or type provided that the solute being focused does not irreversibly bind to the packing. Suitable packings include porous and nonporous, pellicular and tentacle, glass, plastic, ceramic, and any nonconductor or semiconductor. Other suitable packings include ion-exchange, affinity, reverse phase size exclusion, gel filtration and hyperbolic interaction supports.

In certain preferred embodiments, either or both of the titration/separation chamber and electrode chamber comprises cartridge-like inserts that are capable of being easily removed and replaced. The chamber inserts typically reside between an inlet and an outlet for flowing a fluid into and out of the insert chamber. The shape of the chamber is determined by the configuration of the insert. Such a configuration is particularly advantageous in that the configured chamber can be swapped out for chambers of different configurations, making a variety of electric field gradient shapes and strengths available in a single instrument. In other preferred embodiments, the electrode chamber comprises a cartridge-like insert that can be swapped out, for example, to permit changing between a non-configured separation chamber and a configured separation chamber. Typically, the electrode chamber insert will comprise the electrodes. In yet other preferred embodiments, the entire device is contained in an insert that is insertable into an instrument properly set up with appropriate fluidic, electric and other necessary connections. Suitable cartridge configurations will be readily apparent to those of skill in the art, given the benefit of the present disclosure.

Without wishing to be bound by theory, it is presently understood that EFGF devices are based on the principle of opposing two counteracting forces to create a dynamic equilibrium point. The force in one direction is a resultant of bulk fluid flow, commonly referred to a chromatographic flow, which imposes a hydrodynamic velocity on solutes in the stream. In the opposite direction, an electrophoretic velocity is induced with the application of a voltage to the stream containing solutes. The magnitude of the hydrodynamic velocity is proportional to the hydrodynamic radius or apparent size of the solute, and is adjustable with changes in the rate of chromatographic flow and/or with changes in the shape and/or size of the separation chamber. The hydrodynamic velocity will also vary throughout a non-uniform titration/separation chamber as a result of the non-uniformity of the chamber. As such, the hydrodynamic velocity is also dependant upon the shape and size of the titration/separation chamber. In the opposite direction, an electrophoretic velocity is induced with the application of a voltage to the stream containing solutes. The electrophoretic velocity is proportional to the molecular charge of the solute, which is adjustable with changes in solvent pH or composition. The hydrodynamic radius of an analyte is independent of the charge, and thus is independent of the electrophoretic velocity of the analyte. Thus, the provision of a gradient in the electric field and in the flow rate advantageously provides two independent means of achieving separation of charged analytes, thus increasing the likelihood of being able to separate multiple analytes. At a point in the separation path where the opposing velocities are equal in magnitude, yielding a net zero velocity, is the focal point for a particular solute. The focal point is one of a dynamic equilibrium for the solute, whereby any movement from that point results in a non-zero velocity and a restoring force. Upon establishing such an equilibrium, the isoelectric point can be determined as described above.

In establishing a desired electric field gradient, those skilled in the art will recognize that some compensation must be made in the gradient-establishing parameters (i.e. the shape of the electrode chamber or the settings for the electrode array) to address the perturbation or influence in the electric field caused by a non-uniformity of the titration/separation chamber. That is to say, once a particular titration/separation chamber configuration is desired, such that a desired hydrodynamic force gradient is established, that configuration must be taken into account when determining the appropriate configuration of the electrode chamber to achieve the desired shape of the electric field gradient. For example, while a hyperbolic electrode chamber would, in conjunction with a uniform or non-configured separation chamber, lead to a linear field gradient, the electrode chamber must deviate from hyperbolic to achieve a linear field gradient in the presence of a non-uniform separation chamber. Determination of suitable chamber configurations will be readily apparent to those of skill in the art, given the benefit of the present disclosure.

Figure 5:
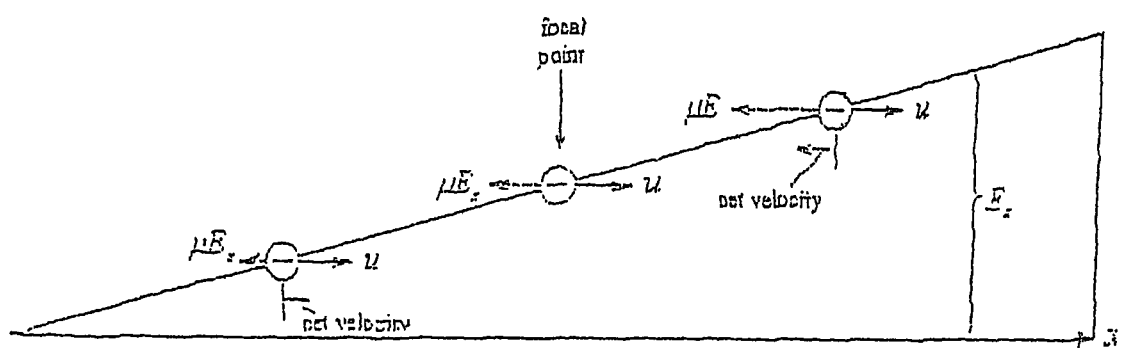
FIG. 5 is a graph further illustrating the principles of EFGF.

When the collected and held-in-place solute or analyte is to be released, for example, where an analyte has been focused in a separation chamber and is to be released into the titration chamber, the electrical field can be decreased or eliminated or the flow rate increased. The concept of electric field gradient focusing is illustrated in FIG. 1, where a constant bulk fluid flow is counteracted by a linear gradient in the electric field strength. A bulk buffer flow pushes solute to the right, while being counteracted by an electrophoretic force in the opposite direction. The magnitude of the electrophoretic force varies along the axis of the separation chamber. FIG. 5 is a further illustration of electric field gradient focusing. In FIG. 5 a charged solute is pushed from left to right by a chromatographic flow. The electric field will impose an electrophoretic migration velocity proportional to the mobility of the solute. At the point where the elution and migration velocities balance is considered the equilibrium focal point for a solute. FIG. 26 further illustrates this concept. First, negatively charged proteins focus in an increasing field gradient with the electric field in the same direction as the convective flow of buffer (A, C, E). Second, positively charged proteins focus in a decreasing field gradient with the electric field in opposite direction as the convective flow (B, D, F). The amount of charge carried on protein molecules are closely related to the pH of the buffer and are generally different from species to species. The migration rate is directly proportional to the amount of charge carried which is generally different from specie to specie. Therefore, distinct stationary accumulation zones for differently charged species are generated along the column. In order to focus the charged protein in the chamber, the direction of electric field, the slope of field gradient and the pH of the elution buffer must be matched. Otherwise, the target protein will be flushed out or concentrated at the very top of the column, allowing no separation at all.

Figure 6:
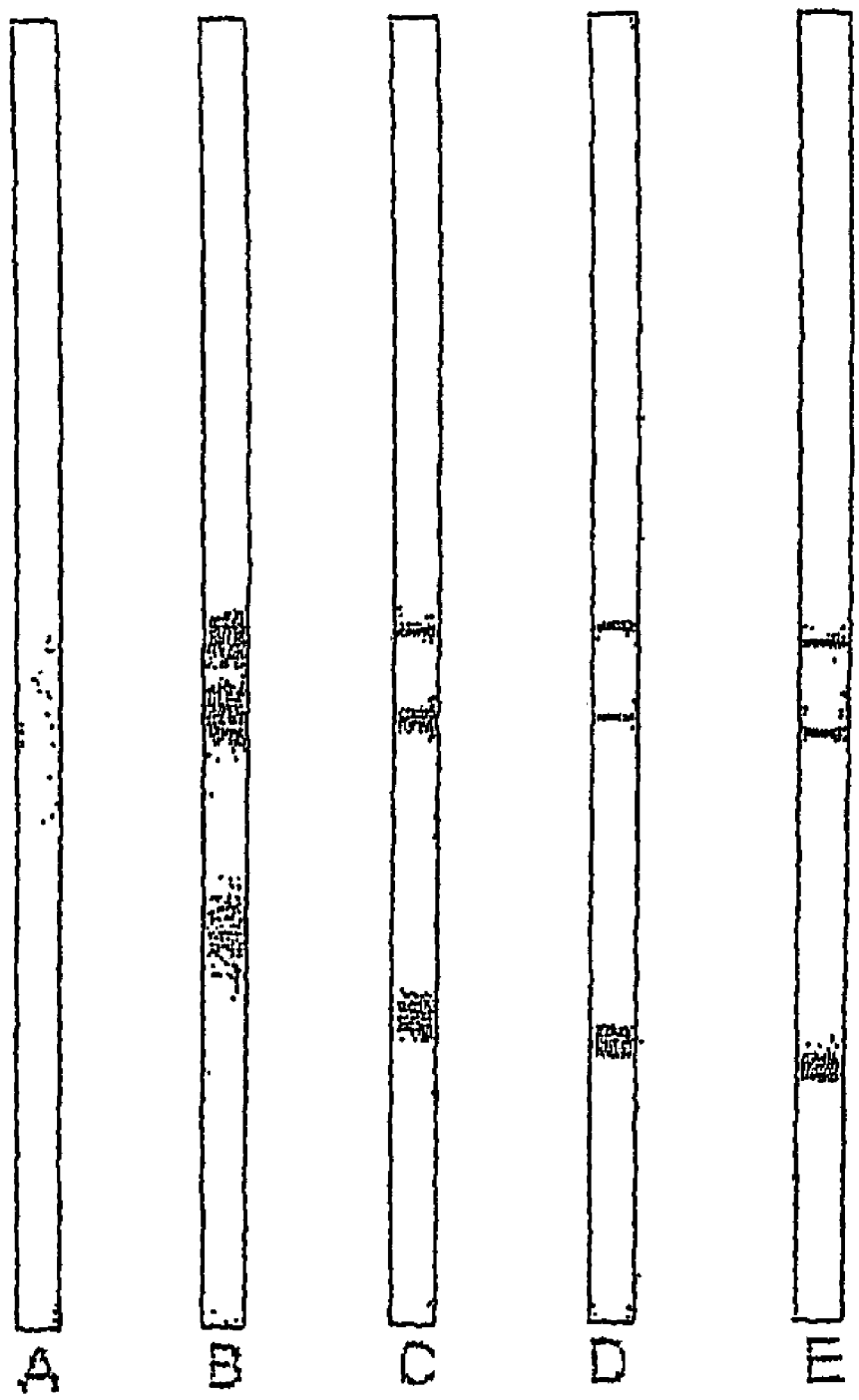
FIG. 6 is a series of images showing three injected proteins coming into focus.

The inherent simplicity of preferred embodiments, e.g., as illustrated in FIG. 2, is advantageous in many applications. Referring again to FIG. 2, the conductive layer (e.g., a dialysis membrane) separates the separation chamber, which is tailored with a hyperbolic curvature to form a linear field gradient, from the electrode chamber. The conductive layer should allow passage of buffer ions and electric current, but should have pore structure that restricts translocation of target molecules from the focusing channel. FIG. 6 presents a series of images extracted from a simulation of a focusing system where three proteins have been injected as a dilute, homogenous mixture. According to model results, a high mobility molecule (small or strongly charged) moves fast to its equilibrium point. Therefore, a focused band can be established in a relatively short amount of time. For a low mobility molecule (big and weakly charged), focusing to equilibrium occurs on a longer time scale. As an example, with field strengths ranging from 20-200 volt/cm, at opposite ends of the chamber, a molecule with an electrophoretic mobility of $5 \times 10^{-5}$ cm2/volt·sec can focus into a 2 mm band in approximate 12 minutes, while a molecule with a mobility of $5 \times 10^{-6}$ cm2/volt·sec will reach its focal point in approximately 2 hours. Slower moving analytes create a challenge for equilibrium focusing techniques, but an increase in focusing speed may be achieved at higher flow rates and higher field strengths. Since it is relatively easy to increase the system flow rate, extension of the operational range primarily focuses on increasing the field strength. The limiting factor to operational conditions may be joule heating and subsequent heat dissipation. It is presently understood that a small-scale device will be capable of 200 V/cm in a 20 mM Tris-phosphate buffer. These field strengths are similar to those used in conventional capillary-scale instruments. It would be advantageous to focus at higher field strengths, but it is believed that in at least certain embodiments fields of 250 V/cm may yield uncontrollable temperature effects and 500 V/cm may prove unrealistic at this scale.

Another exemplary configuration for the devices and methods disclosed here is illustrated in FIG. 7, employing a uniform titration chamber and a configured electrode chamber. Since the cross section of the electrode chamber is significantly larger than the separation chamber, the field gradient is primarily determined by the shape of the electrode chamber. Electrolyte sweeps through the electrode chamber to remove electrolysis products and joule heat. The sample channel may be packed with a chromatographic media to stabilize convective perturbations. The device is seen to be an assembly of three functional layers including the sample focusing channel (upper most layer), the "conductive" membrane, and the electrode chamber (lower most layer). The two chamber layers may be fabricated from common plastics (e.g., acrylic or PEEK with TEFLON AF or quartz components) to allow visualization of the separation processes, however chemical compatibility will be a consideration in material selection. The electrodes, housed in the lower layer, are single electrode elements, typically consisting of either gold or platinum metal to prevent hydrolysis-induced breakdown. Trade-offs in the focusing systems have been observed in balancing the operational range and resolution against the ability to dissipate heat.

In certain preferred embodiments, the separation chamber of an electric field gradient focusing device, for example, a DFGF device, is used first as a separation chamber and subsequently as a titration chamber of the methods and devices disclosed here. Other electrophoretic devices suitable for use in certain preferred embodiments of the methods and devices disclosed here also employing electrode arrays to establish an electric field gradient in a separation chamber are disclosed in U.S. Pat. application Ser. No. 60/440,150, entitled "Devices and Methods for Focusing Analytes in an Electric Field Gradient," filed on 15 Jan. 2003 incorporated herein in its entirety for all purposes. Such devices are described in detail below.

Certain aspects and preferred embodiments provide for incrementing the flowing liquid to a different pH, typically whichever of a higher pH or lower pH results in the pH of the flowing liquid being nearer the isoelectric point of the charged analyte of interest. Such incrementation can be accomplished in certain preferred embodiments by mixing a titrating solution of a differing pH with the flowing liquid, preferably before the flowing liquid flows into the titration chamber, to alter the pH of the flowing liquid. Preferably, the compositions of the titrating solution and the flowing liquid comprise of the same components, i.e. are the same liquids, with the exception of the differences in pH. For example, each of the titrating solution and the flowing liquid can preferably comprise buffers, for example, tris-phosphate buffer, tris-acetate and the like, wherein each of the titrating solution and flowing liquid comprise the same buffer system. Suitable titrating solutions will be readily apparent to those of ordinary skill in the art, given the benefit of the present disclosure.

In certain preferred embodiments, the pH of the flowing liquid is incremented by adjusting the pH of the flowing liquid with a second titrating solution of a different pH. The titrating solution is typically contained in a titration reservoir, from which the titrating solution can be removed, typically by pumping, to adjust the pH of the flowing liquid. The titration reservoir is typically a container, for example a glass jar, which can be easily changed to change titrating solutions, for example when a titrating solution of a different pH is desired. Optionally, the pH of titrating solution is itself adjusted during the analysis, generally while it is in the titration reservoir, such that the titrating solution is continually at a pH of sufficient difference from the carrier liquid to permit incrementation of the carrier liquid but at sufficient closeness to the pH of the carrier liquid to permit greater control over the incrementation of the pH of the carrier liquid. Other suitable titrating reservoirs will be readily apparent to those of ordinary skill in the art, given the benefit of the present disclosure.

The titrating solution in certain preferred embodiments can be mixed directly with the flowing liquid, for example, in a static mixing chamber or an on-line mixer. In other preferred embodiments, the titrating solution does not mix directly with the flowing liquid, but rather is run into a dialyzer, for example, a microdialyzer, that permits ions from the titrating liquid to move into the flowing liquid and increment the pH of the flowing liquid. Other suitable means for adjusting the pH of the first liquid include, for example, metered feeding of acid or base to the flowing liquid or to a second liquid flowing in the electrode chamber. Other suitable means for adjusting the pH of the first liquid will be readily apparent to those of ordinary skill in the art, given the benefit of the present disclosure.

In certain preferred embodiments in which the isoelectric point is determined from pH and corresponding position data of the analyte band within the titration chamber, i.e. where the analyte band is not necessarily eluted from the chamber, the incrementation of the pH of the flowing liquid can be either toward or away from the isoelectric point. This is particularly advantageous for methods in which pH and corresponding position data are collected on either side of the isoelectric point and the isoelectric point is determined from such data, as for example by interpolation, in that separate incrementation systems or separate titration reservoirs need not be employed; the pH can be adjusted, for example, to the isoelectric point from above, the sample can be rapidly quenched to below the isoelectric point, and the pH can then be adjusted to the isoelectric point from below from the same titration reservoir and titration apparatus.

Certain preferred embodiments further comprise a pH sensor for measuring the pH of the carrier fluid which contains the charged analyte. The pH sensor is thus typically located within the carrier fluid. In certain preferred embodiments, the pH sensor is located within the titration chamber. In other preferred embodiment, the pH sensor is located at either the inlet or the outlet of the titration chamber, or just before the inlet or just after the outlet, to measure the pH of the flowing liquid as it just enters or just exits the titration chamber. In preferred embodiments in which the pH of the flowing liquid is incremented at a sufficiently slow rate as to permit monitoring of the pH from a position remote from the titration chamber, the pH sensor may be located remote from the titration chamber. The pH sensor is generally a sensor capable of measuring or determining pH of a range of between 1 and 14, or a subrange thereof. The pH sensor typically comprises a sensor such as an ion-selective electrode or other suitable sensor. Other suitable sensors will be readily apparent to those of ordinary skill in the art, given the benefit of the present disclosure.

In accordance with certain preferred embodiments, a pH sensor is contained either within the titration chamber or proximate the titration chamber, i.e., just at or outside of the inlet or the outlet of the titration chamber for measuring the pH of the flowing liquid. In other preferred embodiments, a second device is connected to the first device, wherein the second device is capable of incrementing the pH flowing liquid in a direction opposite the incrementation of the pH in the first device. Other embodiments contain two such devices, with a sample splitter upstream of the devices such that the charged analyte is split into two portions, with one portion going to each of the devices.

In certain preferred embodiments, the device lacks a pH sensor. Instead, the pH is determined by calculation from knowing the pH of the flowing liquid, the pH of the titrating solution, and the degree to which the two are mixed, i.e. the amount of each that is mixed together, or the degree to which the dialysis of ions from the titration solution to the flowing liquid occurs. Suitable means for calculating the pH of the flowing liquid will be readily apparent to those of ordinary skill in the art, given the benefit of the present disclosure.

The concept of electric field gradient focusing is illustrated in FIG. 1, where a constant bulk fluid flow is counteracted by a linear gradient in the electric field strength. A bulk buffer flow pushes solute to the right, while being counteracted by an electrophoretic force in the opposite direction. The magnitude of the electrophoretic force varies along the axis of the separation chamber. FIG. 26 further illustrates this concept. First, negatively charged proteins focus in an increasing field gradient with the electric field in the same direction as the convective flow of buffer (A, C, E). Second, positively charged proteins focus in a decreasing field gradient with the electric field in opposite direction as the convective flow (B, D, F). The amount of charge carried on protein molecules are closely related to the pH of the buffer and are generally different from species to species. The migration rate is directly proportional to the amount of charge carried which is generally different from specie to specie. Therefore, distinct stationary accumulation zones for differently charged species are generated along the column. In order to focus the charged protein in the chamber, the direction of electric field, the slope of field gradient and the pH of the elution buffer must be matched. Otherwise, the target protein will be flushed out or concentrated at the very top of the column, allowing no separation at all. After focusing, the protein can be eluted from the column by appropriate adjustment of any of these variables.

Certain preferred embodiments of the devices and methods disclosed here comprise means for separating and focusing charged analytes prior to determination of the isoelectric points, preferably by Dynamic Field Gradient Focusing (DFGF) devices or Electric Field Gradient Focusing (EFGF) devices that optionally include a molecular sieve. In certain preferred embodiments, charged analytes can be separated and focused, i.e. concentrated at (about) a single (physical) location in a separation chamber, and then eluted from the chamber and flowed into a titration chamber in accordance with any of the embodiments disclosed here. In other preferred embodiments, the charged analytes are separated and focused, e.g., in the separation chamber of a DFGF, EFGF or other electrophoretic device and then titrated in the same chamber. That is, in such embodiments, the system employs a chamber that is adapted both for electrophoretic focusing and to permit incrementation and measurement of the pH of the flowing liquid. Thus, the isoelectric point is determined in the chamber by any of the methods described herein. Such devices or systems and methods are optionally configured or embodied in a microfluidic platform, e.g., as a so-called "system on a chip." Representative DFGF devices and methods are described below.

A typical DFGF device comprises a first chamber, which may be referred to as a separation chamber, comprising an inlet for introducing a first fluid into the first chamber and an outlet for exiting the first liquid from the first chamber; a second chamber, which may be referred to as an electrode chamber, comprising an electrode array and an inlet for introducing a second liquid into the second chamber and an outlet for exiting the second liquid from the second chamber; and permeable material separating the first and second chambers. The electrode array typically comprises a plurality of electrodes, for example 50 electrodes, arranged linearly along the length of the second, or electrode, chamber.

In certain preferred embodiments, the DFGF device includes a focusing chamber that includes a separation chamber and an electrode chamber separated by a permeable material. Charged analyte separation and focusing occurs in the separation chamber, which optionally includes molecular sieve. The electrode chamber includes an array of electrodes for generating a focusing electric field gradient. The separation chamber is in communication with the electrode chamber through the permeable material. "Electrical communication" as used herein refers to the ability of the electric field gradient that is generated by the electrode array to be transferred, or to have an effect, within the separation chamber, and may be by any means which accomplishes this. The permeable material retains analytes in the separation chamber. Generally, an eluant is introduced into and flows through the separation chamber containing the charged analyte. The eluant flow is opposed to the direction of electrophoretic migration of the analyte.

Various suitable configurations will be apparent to those skilled in the art, given the benefit of this disclosure, for the electrode array associated with the titration chamber and with the separation chamber (if any is used other than the titration chamber). The electric field generated by the electrode array can be DC, AC, or otherwise modulated in time including asymmetric (out of phase) field modulation. The specific nature of the electrode (i.e., size and shape) is not critical. Suitable electrodes include pin-shaped and staple-shaped electrodes, among others. In one embodiment, the electrode array includes a linear array of electrodes (e.g., 50 electrodes arranged linearly) along an axis parallel to the direction of analyte migration. In addition to arrays having electrodes arranged in line with even spacings from one to the next, suitable arrays also include arrays in which the electrodes are not in line and which are not separated by even spacings. Other configurations of electrodes, including two-dimensional electrode arrays, are also within the scope of the methods and devices. Two-dimensional arrays include arrays having rows and columns of electrodes. The second chamber in certain preferred embodiments includes more than one electrode array, for example two electrode arrays on opposite sides of the electrode chamber. Suitable electrode array configurations will be readily apparent to those of ordinary skill in the art, given the benefit of the present disclosure, for example electrode array configurations presented in U.S. Pat. No. 6,277,258, which as noted above is incorporated herein in its entirety for all purposes.

In certain preferred embodiments, each electrode of the array is individually controlled to provide an electric field gradient that can be dynamically controlled (i.e., maintained and adjusted during the course of analyte focusing, separation and/or isoelectric point determination). Control can be manual from the device controller, manually from the device's associated computer, or automatically from the computer once the computer has received feedback from a monitor, such as an optical monitor, for example a video signal, or other suitable monitoring device, following analyte focusing. The controller can sense the electrode's voltage and reset its voltage to its initial setting. Such monitoring allows for computer detection of various peaks, optimization of the separation by locally adjusting the field gradient to tease separated peaks apart, and then pull off those peaks that were selected by the operator either before or during a separation. Suitable configurations of the electrodes, controls, computer equipment and the like will be readily apparent to those of ordinary skill in the art, given the benefit of the present disclosure, for example configurations presented in U.S. Pat. No. 6,277,258, which as noted above is incorporated herein in its entirety for all purposes.

In accordance with certain preferred embodiments, the electronically generated field can take on arbitrary shapes including exponential profiles, steps, and even locally reversed gradients, for example, to elute proteins. The field shape can be monitored and maintained by computer and modified "on-the-fly" on a point-by-point basis, both spatially and temporally. During a run the operator can optimize the local properties of the field to separate individual focused bands of charged analyte, sharpen an individual band, move a band to an offtake port or set up a moving gradient to elute one or more bands from the chamber. With online monitoring, for example optical such as UV-Visible monitoring, or potentiometric monitoring, in place, the operator could be replaced by a computer programmed to detect focused peaks and automatically adjust the field shape to optimize the separation and, when necessary, offload products. Suitable monitoring systems and configurations will be readily apparent to those of ordinary skill in the art, given the benefit of the present disclosure.

Embodiments utilizing an electrode array can optionally include, in addition to the electrode array, an auxiliary electrode pair. In such embodiments, the electrodes of the pair are positioned adjacent opposing ends of the electrode array.

As discussed above, the electrodes in certain preferred embodiments are separated from the separation chamber by a membrane. Suitable membranes allow an electric field to be generated through the membrane material in the separation chamber while desired analytes, for example, macromolecules such as biomacromolecules, are retained in the separation chamber, that is, are not able to directly contact the electrodes. In certain preferred embodiments, the membrane is conductive to heat but not to bulk fluid flow. The membrane advantageously serves to isolate the electrodes from the separation chamber and optionally to avoid disruption of the laminar flow by gas generation or denaturation of charged analyte by contact with the electrodes. Suitable conductive materials include but are not limited to Nafion, cellulose based membranes, membranes having a MWCO of about 100-1000, etc. In certain preferred embodiments, the titration and electrode chambers are separated by the membrane. In such embodiments, the membrane is typically a permeable material. As used herein, a permeable material is one that allows communication through the permeable material while (1) desired analytes, for example macromolecules such as biomacromolecules, are retained in the titration or separation chamber; (2) undesired contaminants can be dialyzed out of the titration or separation chamber; and (3) desired molecules, for example buffer ions, etc., can be dialyzed into the titration or separation chamber. In certain preferred embodiments, the permeable material is conductive to heat and buffer ions but not to bulk fluid flow. The permeable material advantageously serves to isolate the electrodes from the separation chamber to avoid disruption of the laminar flow by gas generation or denaturation of charged analyte by contact with the electrodes. Suitable permeable materials include permeable membranes such as dialysis membranes and ion exchange membranes. Other suitable permeable materials will be readily apparent to those of ordinary skill in the art, given the benefit of the present disclosure.

Certain preferred embodiments incorporate an EFGF device separate from the titration chamber for separating and focusing the charged analyte prior to determining the isoelectric point of the charged analyte. In some preferred embodiments, the charged analyte is separated and focused in an EFGF device and then eluted into a device in accordance with any of the above embodiments for determination of the isoelectric point. In yet other embodiments, the separation, focusing, and determination of the isoelectric point all take place within the same chamber. Devices and methods for separating and focusing charged analytes are disclosed in U.S. Pat. No. 6,227,258. Certain preferred embodiments further comprise a molecular sieve in the EFGF first chamber for separating molecules with similar or the same charge to mass ratios. Such charged analytes can be eluted following separation and focusing to a device in accordance with the above embodiments, or the isoelectric point can be determined within the EFGF cell itself Focusing in an electric field gradient and employing molecular sieve is described in detail in U.S. Patent application Ser. No. 60/440,150, entitled "Devices and Methods for Focusing Analytes in an Electric Field Gradient," filed on 15 Jan. 2003, also incorporated herein in its entirety for any and all purposes.

Other preferred embodiments incorporate an EFGF device separate from the titration chamber for separating and focusing the charged analyte prior to determining the isoelectric point of the charged analyte. In some preferred embodiments, the charged analyte is separated and focused in an EFGF device and then eluted into a device in accordance with any of the above embodiments for determination of the isoelectric point. In yet other embodiments, the separation, focusing, and determination of the isoelectric point all take place within the same chamber. As noted above, certain electrophoretic focusing devices employ molecular sieve in the separating chamber. Such devices are especially suitable for the separation and focusing of multiple analytes simultaneously in a separation chamber. Devices and methods for separating and focusing charged analytes by EFGF, including embodiments employing molecular sieve in the separation chamber, are disclosed in U.S. Pat. No. 6,277,258, in U.S. application Ser. No. 60/440,150, entitled "Devices and Methods for Focusing Analytes in an Electric Field Gradient," filed on 15 Jan. 2003; U.S. application Ser. No. 60/430,493, entitled "Electrophoresis Device, System and Method for Sample Management and Hyphenation of Analytical Instruments," filed on Dec. 2, 2002; U.S. application Ser. No. 60/447,997, entitled "Electrophoresis Device, System and Method for Sample Management and Hyphenation of Analytical Instruments," filed on Feb. 18, 2003; U.S. Application Ser. No. 60/471,616, entitled "Electrophoresis Device, System and Method for Sample Management and Hyphenation of Analytical Instruments," filed on May 19, 2003; U.S. application Ser. No. 60/471,623, entitled "CONFIGURED SEPARATION CHAMBER," filed on May 19, 2003; or in U.S. application Ser. No. 60/471,595, entitled "CONFIGURED ELECTRODE CHAMBER," filed on May 19, 2003, all of which are, as noted above, incorporated herein in their entirety for any and all purposes. Certain preferred embodiments further comprise a molecular sieve in the EFGF sample channel for separating molecules with similar or the same charge to mass ratios. Such charged analytes can be eluted following separation and focusing to a device in accordance with the above embodiments, or the isoelectric point can be determined within the EFGF cell itself. Other suitable means for separating charged analytes prior to determining the isoelectric points will be readily apparent to those of skill in the art, given the benefit of the present disclosure.

As noted above, certain preferred embodiments comprise separating and focusing the charged analytes by DFGF or by EFGF prior to determination of the isoelectric point. In yet other preferred embodiments, the determination of the isoelectric point is made in a DFGF or EFGF cell that includes a pH detector, means for incrementing the pH of the flowing liquid which contains the sample, and a detector for determining the location of a band of focused charged analyte in the first chamber of the DFGF or EFGF cell.

Aspects or features of DFGF and EFGF cells, and methods of operation of such, disclosed by way of example herein should be understood to be disclosed generally for use with other aspects and embodiments of the devices and methods disclosed herein unless otherwise indicated or unless otherwise clear from the context in which it is described.

Typically, when utilizing DFGF, the electric field gradient for both titration chambers and separation chambers is established and maintained using an array of electrodes whose voltages are individually monitored and adjusted by a computer-controlled circuit board. Because the field shape is dynamically controlled from the computer on a point-by-point basis, the field profile can be adjusted during a run to improve the resolution of components.

Suitable fluid media for titration and separation purposes include, e.g., a simple fluid (e.g., buffered water), complex fluid (e.g., a water, acetonitrile, methanol mixture), or polymer solution (e.g., linear polyacrylamide, polyvinyl alcohol, methyl cellulose solutions). The fluid medium can also include a chromatography support medium or packing. Suitable packings can be of any size or type provided that the analyte being focused does not irreversibly bind to the packing. Packings can be porous or nonporous, pellicular or tentacle, glass, plastic, ceramic, any nonconductor or semiconductor. Other suitable packings include ion-exchange, affinity, reverse phase size exclusion, gel filtration, and hydrophobic interaction supports.

Generally, a higher concentration of buffer stabilizes a protein sample and therefore avoids precipitation. However, in general, high ionic strength means high conductivity of the buffer, which increases the heat generation and power consumption and, for DFGF, sets a limit for the highest applicable field strength. Advantageously, the same buffer is used for the titration and separation chambers and their respective electrode chamber, to ensure the ion balance between the two sides. The buffer in the second chamber goes upward in the electrode chamber, effectively removing the tiny gas bubbles generated at the electrodes and acts as coolant to remove the Joule heat generated. In certain preferred embodiments, this second liquid is then run through a cooling apparatus, such as a cooling bath, heat exchanger, etc., to remove the heat from the second liquid and the second liquid is then recycled back into the second chamber. Another important role of the second liquid is to conduct the electric field gradient through the permeable membrane to the separation chamber. Other suitable first and second liquids will be readily apparent to those of ordinary skill in the art, given the benefit of the present disclosure.

In operation, a DFGF-type or EFGF-type separation or focusing device and the titration devices disclosed here typically include the flow of a first liquid through the separation or titration chamber, as the case may be, and the flow of a second liquid through the electrode chamber. Generally, the first liquid is an electrophoretic eluant (e.g., buffer solution) and the second liquid is a coolant. The first liquid can be the same as or different from the second liquid. Depending on the requirements of the particular application, the composition of either the first and/or the second liquid can be changed to achieve the desired result. As noted above, liquid flow through the separation or titration chamber opposes the direction of electrophoretic migration of the analyte and can be driven by any one of a variety of forces including electric field, pressure, vacuum, or other motive force. In a preferred embodiment, the direction of liquid flow through the separation or titration chamber is opposite that through the electrode chamber.

The description of devices and methods of separating and focusing charged analytes that follows is meant to encompass such electrophoretic devices, for example, DFGF-type devices, which devices employ molecular sieve in the separation chamber. The electrophoretic devices operate under a given set of focusing process parameters, including all parameters, both dynamic and non-dynamic, that affect the location of a focused band of charged analyte in the separation chamber, other than the influence of the molecular sieve. With the influence of the molecular sieve, the focusing location is different than it would be in the absence of the molecular sieve. All such parameters are encompassed by the term "focusing process parameters" unless otherwise noted or otherwise clear from context. Such factors include, for example, dynamic factors, or factors that are capable of being changed, such as the particular characteristics such as the shape and strength of the electric field gradient; the composition, concentration and pH of the first liquid; the flow rate of the first liquid; the composition, concentration and pH of the second liquid; the flow rate of the second liquid; and other such dynamic factors. The parameters that make up the focusing process parameters further include nondynamic factors such as the dimensions of the first chamber and second chamber; and other such nondynamic factors.

In simultaneous focusing in a separation chamber of multiple charged analytes having the same or similar charge to mass ratios, the composition and amount of molecular sieve is chosen such that the location of the stationary focused band of each such analyte is shifted in the chamber to a different degree. It should be understood, however, that reference here to each of multiple analytes being shifted to a different degree does not exclude the possibility that in any given stationary focused band there may be more than one analyte, that is, there may be analyte mixtures for which the devices and methods disclosed here are operative to establish focuses bands of subsets of the analytes, each subset containing one or more of the analytes. Typically the analytes are separated on the basis of their molecular weights or masses. This is particularly useful for separating analytes that have the same or similar mobilities that would not adequately separate in a traditional DFGF or EFGF device absent the sieve.

Molecular sieves include any medium or substance, for example suitable organic or inorganic polymer or the like, by which such shifting of the focusing location is achieved. The molecular sieve is selected for its ability to shift the location of the stationary focused band of analyte for simultaneous focusing of multiple charged analytes. Preferably, a molecular sieve is chosen such that the amount to which the stationary focused bands of analyte are shifted for a given set of focusing conditions varies with the size or molecular weight of the analyte. Preferably the degree of shift varies proportionally with the molecular weight of the analyte, for example, such that each stationary focused band of charged analyte is focused at a stable location separate from the other charged analytes. Factors that affect the selection of a particular molecular sieve at a particular concentration include, for example, the size of the molecules to be separated and focused, the pH at which the system is operated, and other such relevant factors that will be apparent to those skilled in the art, given the benefit of this disclosure. In certain preferred embodiments, the molecular sieve comprises a gel, which may be either an organic gel or an inorganic gel or a combination of organic and inorganic gel. The gel may be a fixed gel. A fixed gel optionally may be polymerized within the first chamber, such that it does not substantially flow or move when fluid sample is flowed through the first chamber. Alternatively, the gel may be a soluble gel that is dissolved in the first liquid, such that the gel flows with the first liquid when the first liquid flows through the first chamber. In certain embodiments, the soluble gel is introduced into the chamber and resides there during focusing. As used herein, the term "soluble gel" refers to a gel that is soluble or dissolved in a liquid or fluid, and further refers to gels that form suspensions, emulsions, colloids, and the like. Typically, soluble gels comprise polymers having little or no crosslinking. In certain preferred embodiments, the gel will be comprised of molecules having a molecular weight of between about 2000 and about 100,000. Suitable gels include, for example, linear polyacrylamide, polyvinyl alcohol, methyl cellulose and other derivatized celluloses, and the like. Other suitable molecular sieves include microporous structures composed of either crystalline aluminosilicate, chemically similar to clays and feldspars and belonging to a class of materials known as zeolites, or crystalline aluminophosphates derived from mixtures containing an organic amine or quaternary ammonium salt, or crystalline silicoaluminophosphates which are made by hydrothermal crystallization from a reaction mixture comprising reactive sources of silica, alumina and phosphate, and the like. Those of ordinary skill in the art will be able to select suitable gels and sieves through routine experimentation, utilizing known methods, for example by the methods described in Ackers et al., "Determination of stoichiometry and equilibrium constants for reversibly associating systems by molecular sieve chromatography," Proc. Nat. Acad. Sci. USA 53: 342-349 (1965), the entire disclosure of which is hereby incorporated by reference for all purposes. Other suitable sieves will be readily apparent to those of ordinary skill in the art, given the benefit of the present disclosure.

In accordance with certain preferred embodiments, the devices disclosed here have a first block comprising a first trough having an inlet for introducing liquid to the first trough and an outlet for exiting liquid from the first trough. A second block has a second trough with an inlet for introducing a second liquid to the second trough and an outlet for exiting the second liquid from the second trough. The second trough further comprises electrodes, for example, an electrode array, positioned in the second trough, wherein the first trough and the second trough are substantially coincident and form a channel when the first block is sealed to the second block. A permeable material is provided intermediate the first and second blocks, dividing the channel formed when the first block is sealed to the second block into a first chamber and a second chamber. The second chamber includes the electrodes. The first chamber holds a molecular sieve to shift the location of a stationary focused band of charged analyte in the first chamber for a given set of focusing process parameters. The device as such is in the configuration of a discrete unit, or "chip" or consumable cartridge, for example a microfluidic cartridge, which can be swapped out of a suitable receptacle in a laboratory or processing instrument or the like.

It should be understood that the same block structure can also be employed in the pI titration devices and methods disclosed and described above, and can be employed with the configured chambers as well as the electrode array. Suitable block structures will be readily apparent to those of skill in the art, given the benefit of the present disclosure.

As noted above, the second chamber of the electrophoretic focusing device includes electrodes. The principles noted above regarding electrodes for the titrating chamber are applicable here also and are incorporated here by reference.

As discussed above, the separation and electrode chambers in certain preferred embodiments are separated by a permeable material. The discussion above regarding permeable materials for certain preferred embodiments of the titration chamber is equally applicable here and is incorporated here by reference.

The first and second liquids, that is the liquids for the separation chamber and for the electrode chamber of the electrophoretic focusing device, may comprise water or advantageously may comprise buffer. In general, the liquids disclosed above for the titration devices and methods are useful also in the electrophoretic focusing device, and such discussion is incorporated here by reference.

In certain preferred embodiments, the focused analytes can be eluted from the electrophoretic focusing device through one or more separation ports positioned midway along the separation chamber between the inlet port and the outlet port. Basically, the desired analyte can be focused to a region of the chamber from which the analyte can be eluted through a port. Analytes can be eluted from the separation chamber by electric field, pressure, vacuum, or other motive force.

Certain preferred embodiments of the device can further include a monitoring feature which detects analyte migration. Suitable analyte detectors include the same type of detectors discussed above with regard to the titration chamber, which discussion is incorporated here by reference. Optical methods include providing a clear window in the first chamber so that an operator can observe the focusing of the bands directly, and further include optical methods such as UV/Visible spectroscopy that can be monitored by the operator or by computer. Optional integration of the signal put forth from the monitoring feature with software allows automation and computer optimization of analyte loading, separation, and elution steps.

The electrophoretic focusing device can be operated in a continuous mode in which analyte for focusing and/or separation is continuously loaded into the separation chamber and focused to offtake ports where the analytes are continuously eluted. In the alternative, the device can be operated in a batch mode in which the analyte is loaded in its entirety and then focused.

An electrophoretic method for focusing a charged analyte is employs device in accordance with the embodiments above. A first fluid comprising at least one charged analyte is introduced into the separation chamber and an electric field gradient is applied to the charged analyte in the separation chamber to focus the charged analyte in the electric field gradient, wherein the separation chamber contains molecular sieve operative to shift the location at which a stationary focused band of a charged analyte forms under a given set of focusing process parameters. In certain preferred embodiments, the electric field gradient is established at least in part by the non-uniformity of the titration chamber, the electrode chamber, or both. The electric field gradient is preferably generated by an electrode array by individually adjusting the electrode voltages of each element of the array. Certain preferred embodiments employ an electrode array in conjunction with a configured titration chamber, electrode chamber, or both. In certain preferred embodiments, the electric field gradient is dynamically controlled, that is to say the electric field gradient is changed or adjusted while the focusing takes place.

In certain preferred embodiments a hydrodynamic force is applied to the first fluid by pumping the first fluid through the separation chamber. The first fluid typically is a liquid with flow rates ranging, e.g., from 0.1 to 10 L/min. for analytical applications, and, e.g., from 10 to 200 L/min. for preparative applications. The flow rate is chosen to provide the desired separation, in other words so that the hydrodynamic force, when combined with the effect of the molecular sieve, counters the electric field gradient at a position between the weakest and the strongest part of the electric field. In this fashion, the analyte will be retained within the first chamber. Factors that affect the choice of flow rate include, for example, the viscosity and density of the liquid, strength of the electric field gradient, net charge of the analyte, etc. Suitable flow rates will depend, therefore, in part upon the electric field gradient that is chosen. Suitable flow rates can be readily determined by routine trial and error.

In operation, the device includes the flow of a first fluid, typically a liquid, through the first, or separation chamber and the flow of a second fluid, also typically a liquid, through the second, or electrode chamber. Generally, the first liquid is an electrophoretic eluant (e.g., buffer solution) and the second liquid is a coolant. Suitable liquids include simple liquids such as buffered water, complex fluids, for example mixtures of water and solvent, etc. The first liquid can be the same as or different from the second liquid. During focusing and separation, and depending on the requirements of the particular separation, the composition of either the first and/or the second liquid can be changed to achieve the desired result. As noted above, liquid flow through the separation chamber preferably opposes the direction of electrophoretic migration of the analyte and can be driven by any one of a variety of forces including electric field, pressure, vacuum, or other motive force. In a preferred embodiment, the direction of liquid flow through the separation chamber is opposite that through the electrode chamber.

Figure 20:
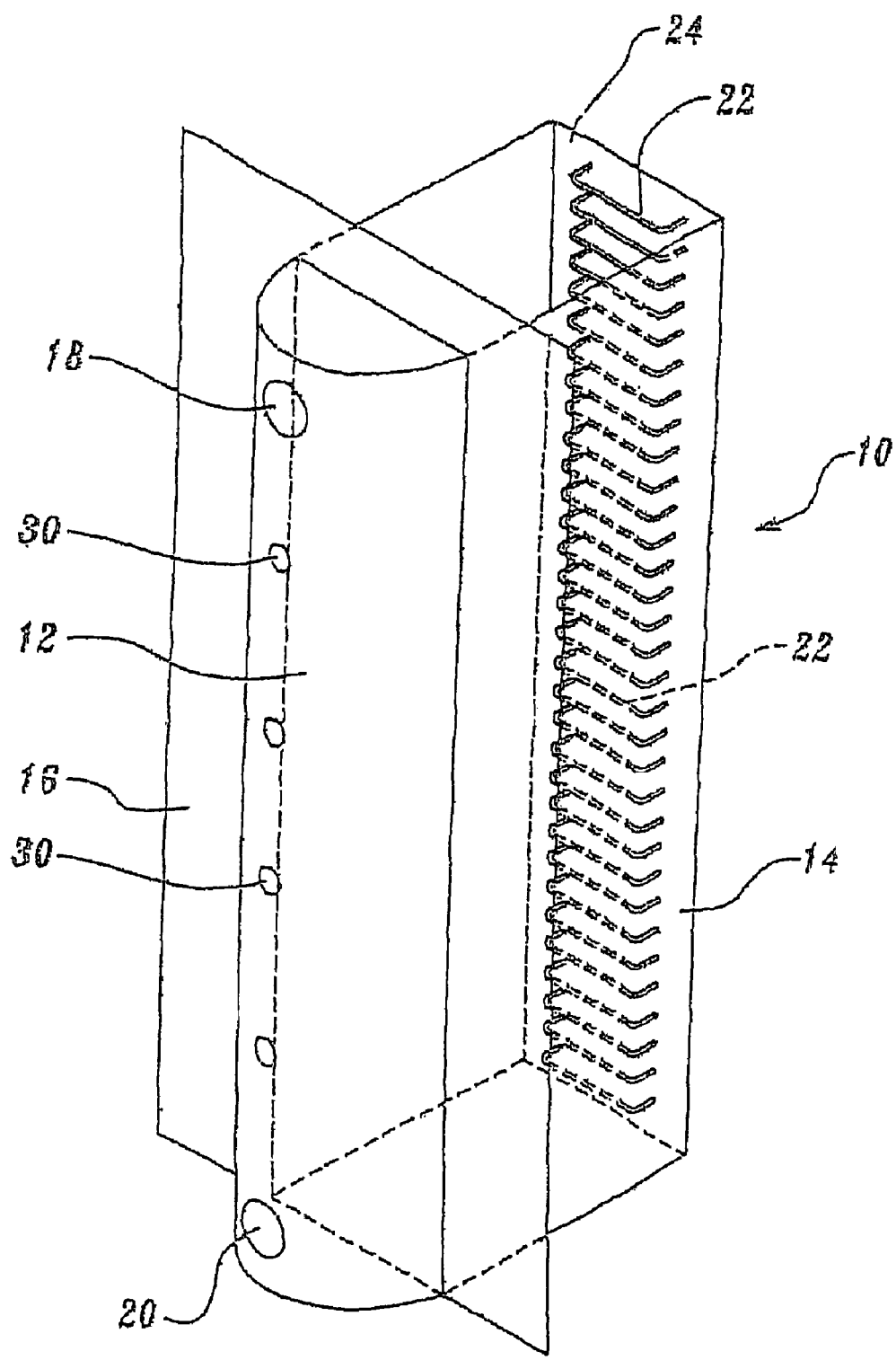
FIG. 20 is a schematic perspective view of a first embodiment of the devices disclosed here.
Figure 21:
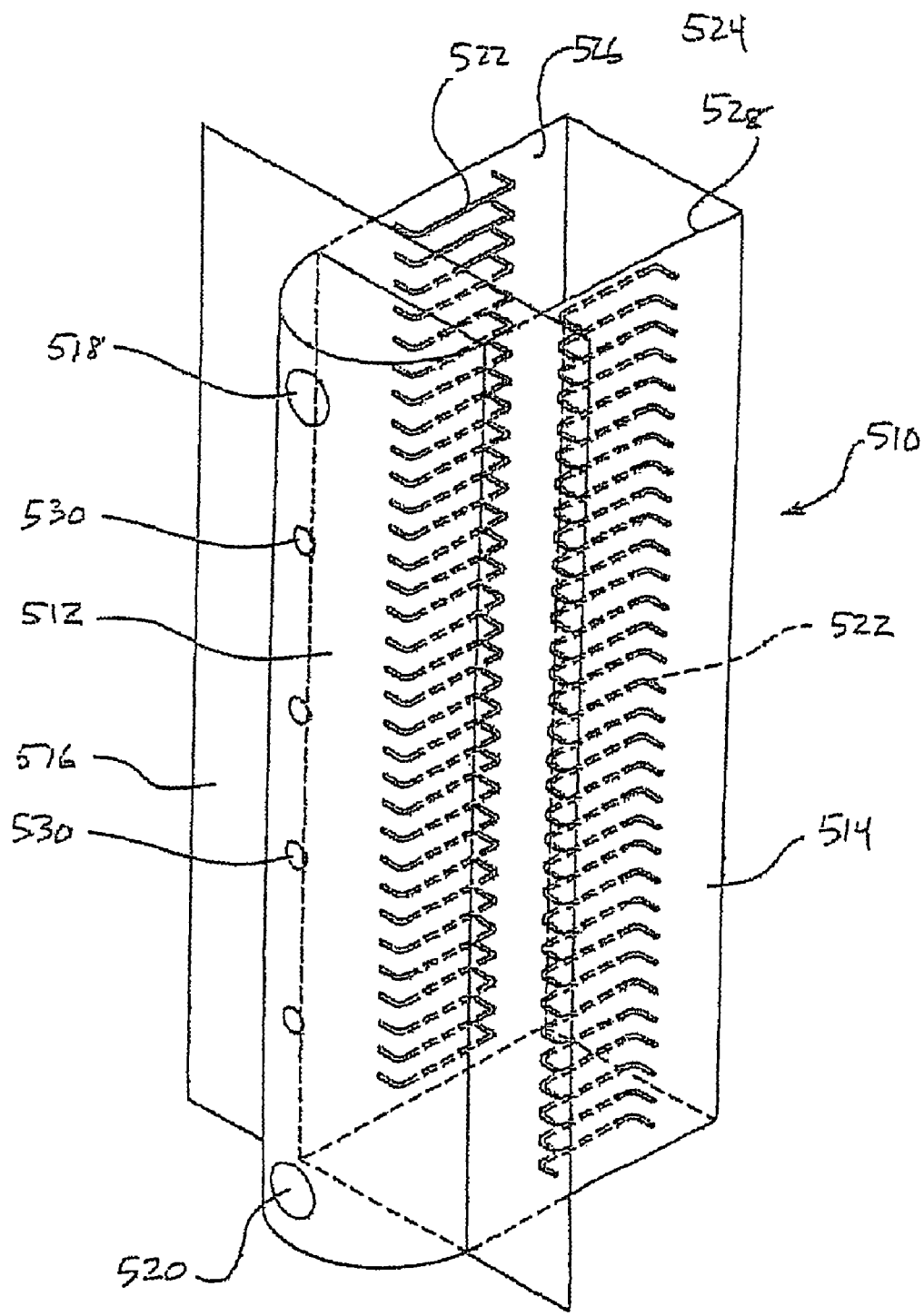
FIG. 21 is a schematic perspective view of another embodiment of the devices disclosed here.

A focusing chamber comprising an electrode array is shown schematically in FIG. 20. Referring to FIG. 20, focusing chamber 10 includes separation chamber 12 and electrode chamber 14 separated by permeable member 16. The electrode chamber 12 shown in FIG. 1 is uniform axially; in practice, the electrode chamber would of course be non-uniform axially. Separation chamber 12 includes elution buffer inlet 18 and outlet 20. In operation, in one embodiment, elution buffer flows downward from inlet 18 through chamber 12 exiting outlet 20, and coolant buffer flows through electrode chamber 14, preferably upwardly. Electrode chamber 14 includes an array of electrodes 22. As shown in FIG. 20, the electrode array can be positioned on the electrode chamber surface 24 opposing separation chamber 12 and permeable member 16. The device can further include one or more ports 30 for eluting analytes from the separation chamber. Alternatively, as shown in FIG. 21, the electrode chamber 514, which again is shown for clarity purposes to be uniform axially, includes a pair of electrode arrays 522. Referring to FIG. 21, in this embodiment, the electrode array includes an electrode array positioned on electrode chamber surfaces 526 and 528 adjacent separation chamber 512 and permeable member 516. Device 510 can further include one or more ports 530 for eluting analytes from the separation chamber.

In certain preferred embodiments, each electrode of the array is individually controlled to provide an electric field gradient that can be dynamically controlled (i.e., maintained and adjusted during the course of analyte focusing and/or separation). Techniques involving such dynamic control of the electric field gradient are referred to herein as "Dynamic Field Gradient Focusing" or "DFGF." Control can be manual from the device controller, manually from the device's associated computer, or automatically from the computer once the computer has received feedback from a monitor, such as an optical monitor, for example a video signal, or other suitable monitoring device, following analyte focusing. The controller can sense the electrode's voltage and reset its voltage to its initial setting. Such monitoring allows for computer detection of various peaks, optimization of the separation by locally adjusting the field gradient to tease separated peaks apart, and then pull off those peaks that were selected by the operator either before or during a separation. Suitable configurations of the electrodes, controls, computer equipment and the like will be readily apparent to those of ordinary skill in the art, given the benefit of the present disclosure, for example, configurations presented in U.S. Pat. No. 6,277,258, which as noted above is incorporated herein in its entirety for all purposes. The inclusion of an electrode array is particularly advantageous in that the strength and shape of the electric field gradient can be altered during the run, for example, to elute focused bands of analyte off one by one, thus permitting each band to be subject to individual treatment following separation in the device. In accordance with certain preferred embodiments of the device and methods, the electronically generated field can take on arbitrary shapes including exponential profiles, steps, and even locally reversed gradients, for example, to elute proteins. The field shape can be monitored and maintained by computer and modified "on-the-fly" on a point-by-point basis, both spatially and temporally. During a run the operator can optimize the local properties of the field to sharpen an individual band, move a band to an offtake port or set up a moving gradient to elute one or more bands from the separation chamber. With online monitoring, for example optical such as UV/Visible monitoring, or potentiometric monitoring, in place, the operator could be replaced by a computer programmed to detect focused peaks and automatically adjust the field shape to optimize the separation and, when necessary, offload products. Suitable monitoring systems and configurations will be readily apparent to those of ordinary skill in the art, given the benefit of the present disclosure.

Figure 22A:
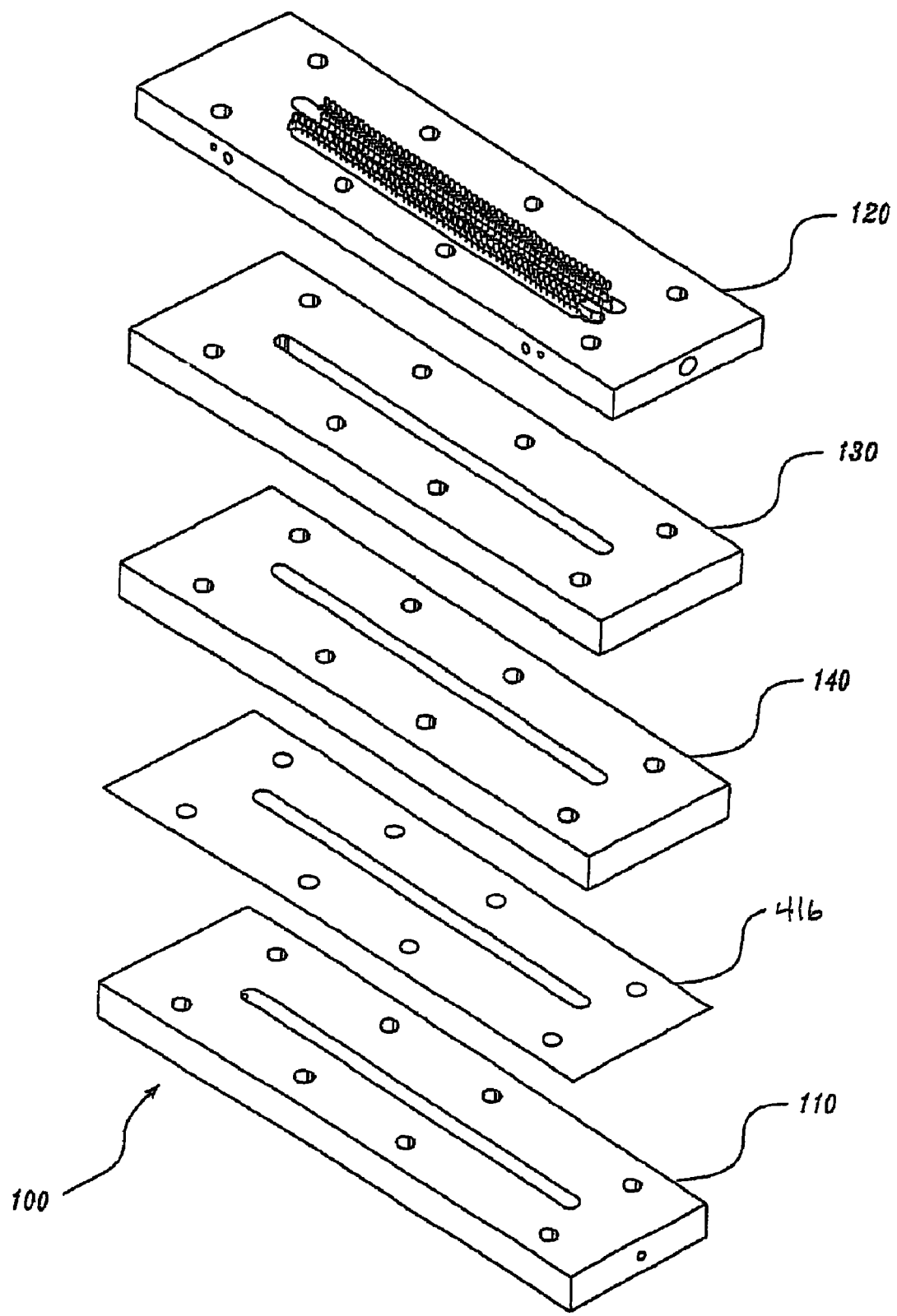
FIG. 22A is an exploded view of another embodiment of the devices disclosed here.
Figure 22B:
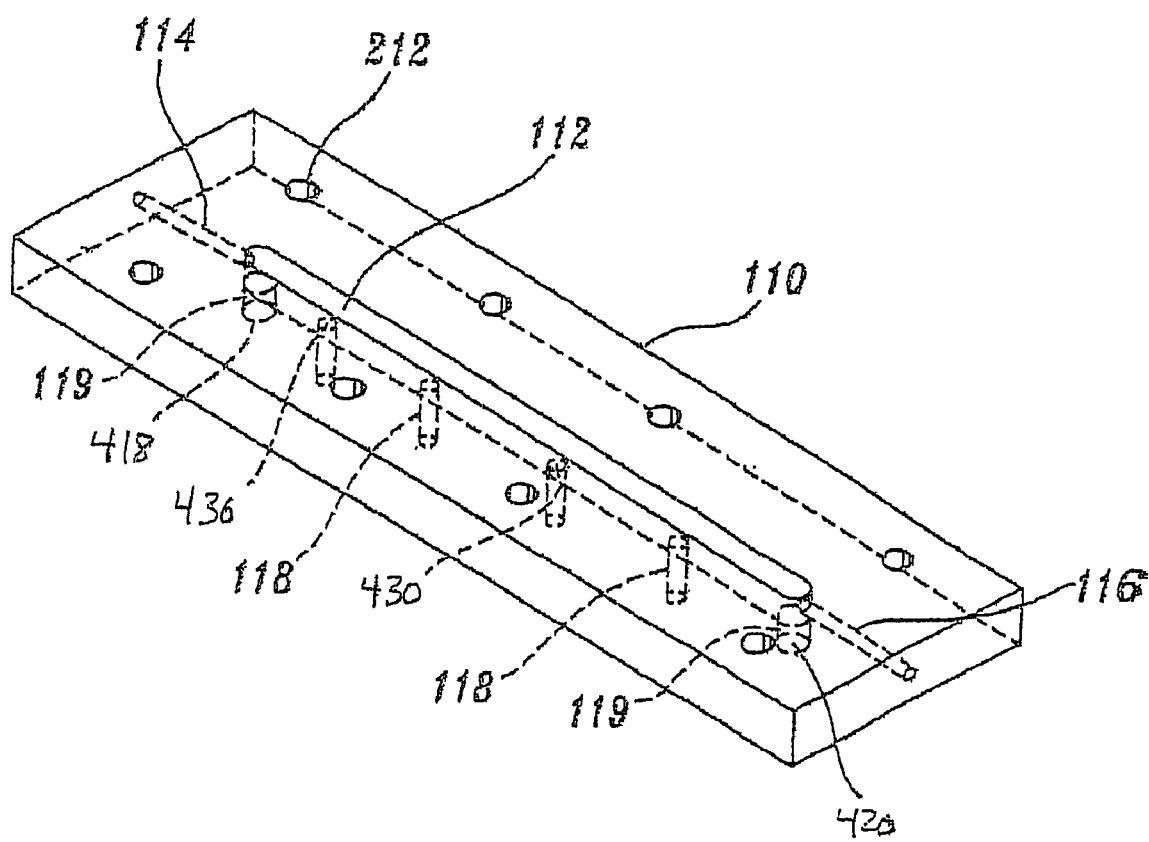
FIGS. 22B-22E are schematic perspective views of selected components of the device illustrated in FIG. 22A.
Figure 22C:
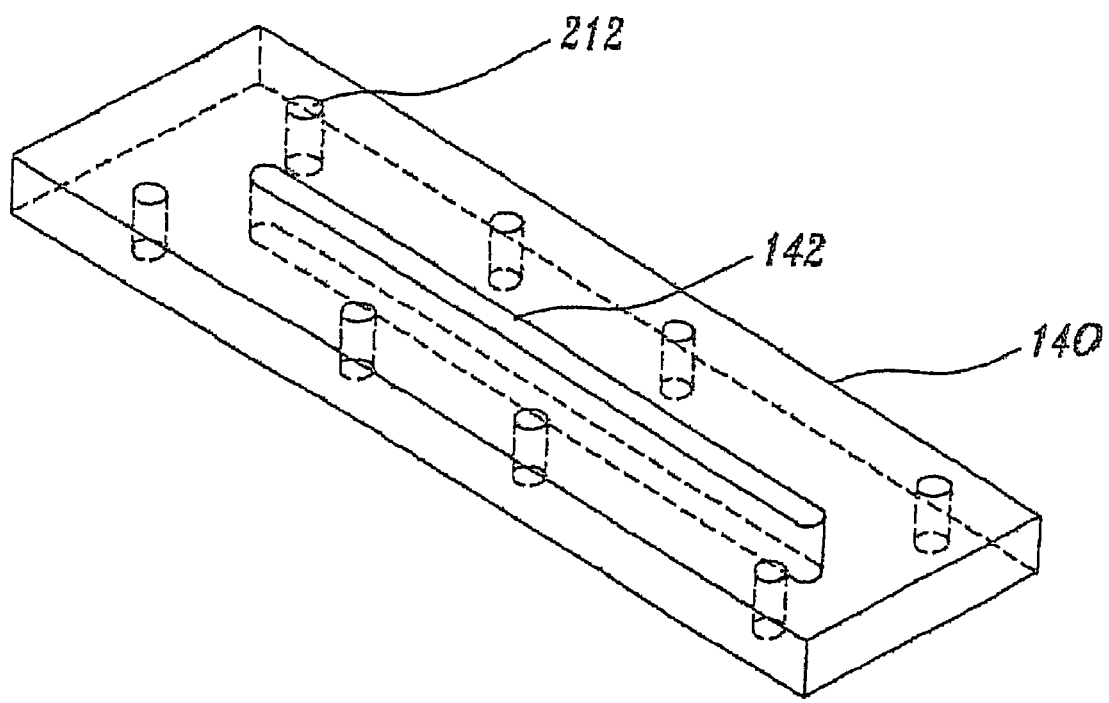
Figure 22D:
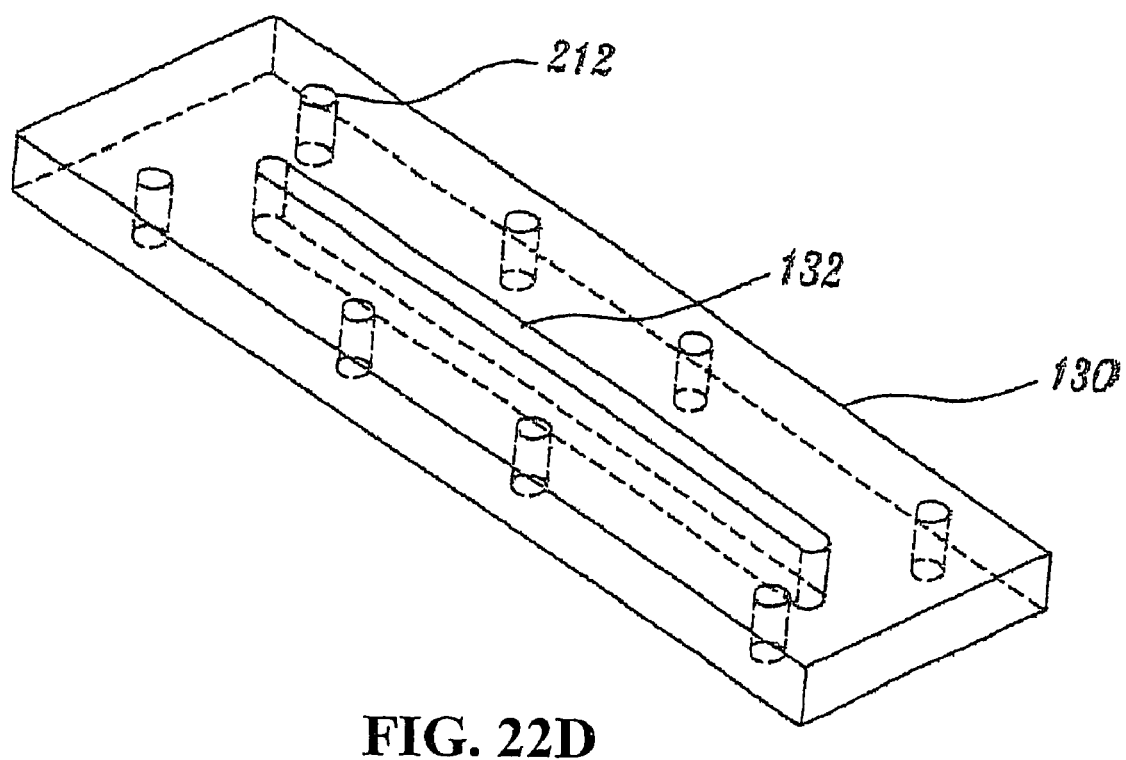
Figure 22E:
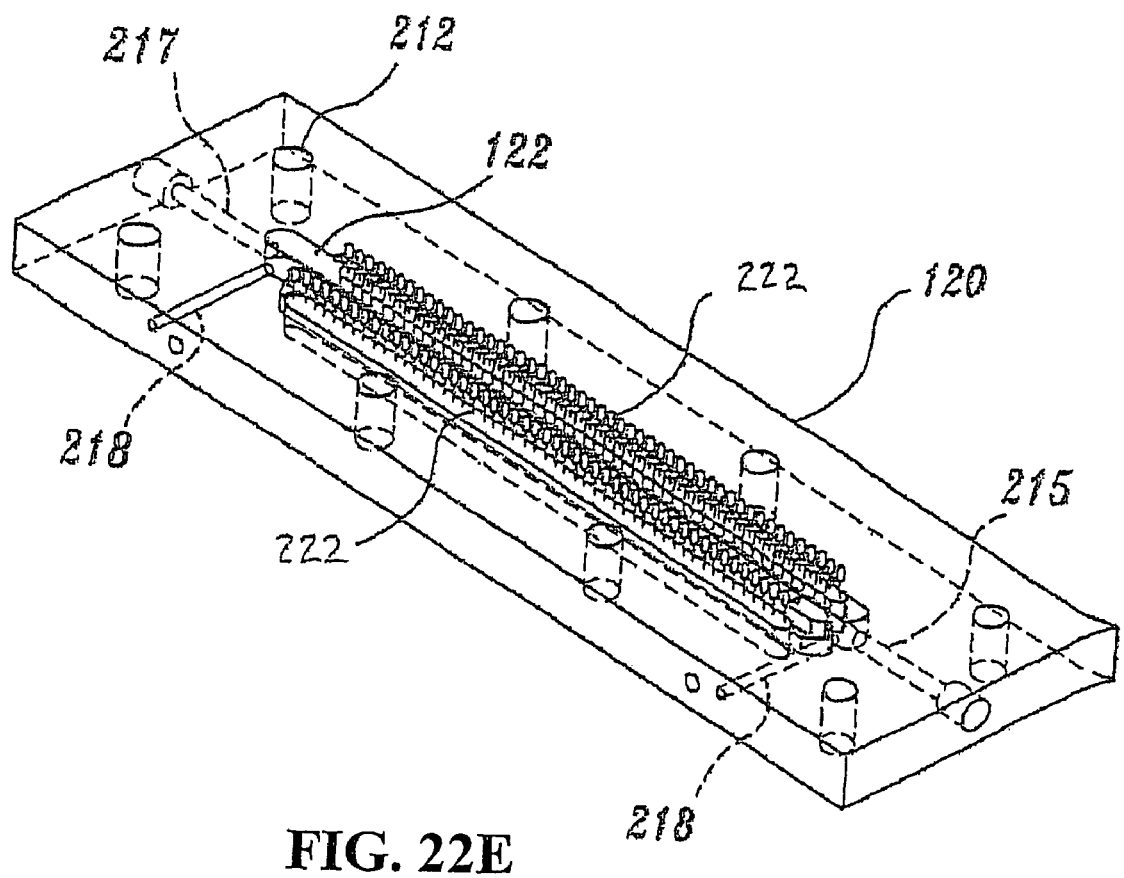
Figure 23:
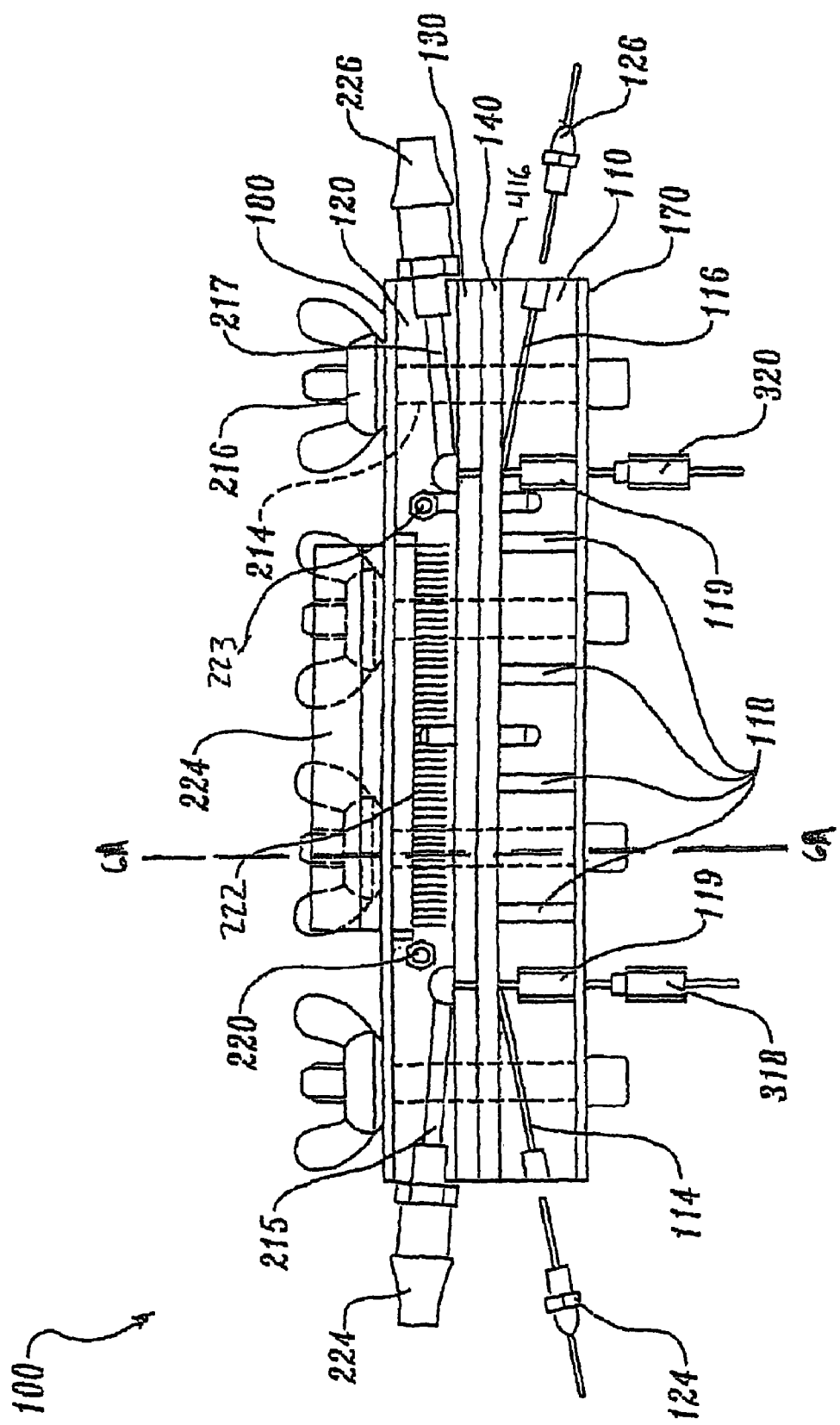
FIG. 23 is an elevation view, partly in section, of the device of FIGS. 22A-22E in assembly.
Figures 24A, 24B:
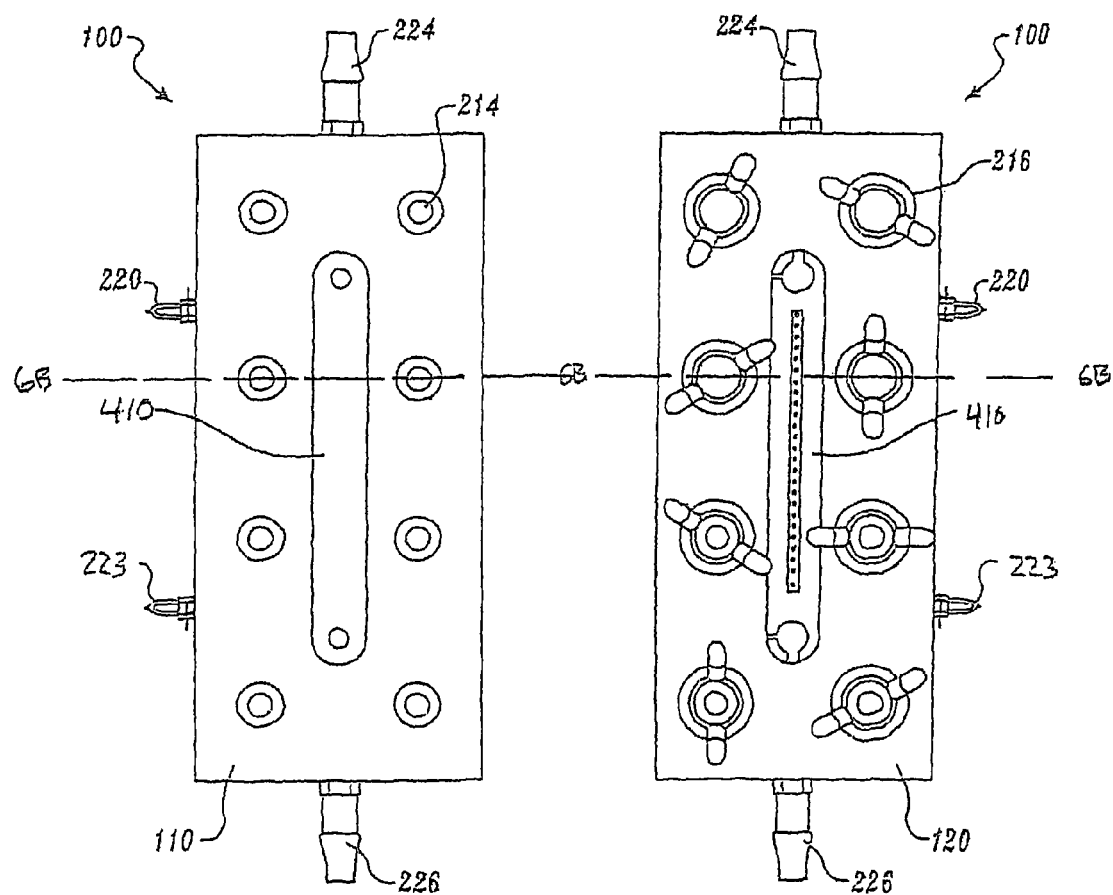
FIGS. 24A and 24B are front and back plan views, respectively, of the device of FIGS. 22-22E and 23 in assembly.

A representative electrophoretic device including a focusing chamber as described above is shown in FIGS. 22-25. FIG. 22A shows an exploded view of the device including front and rear portions. An elevation view of the device is shown in FIG. 23, and forward and rear plan views of the device as illustrated in FIGS. 24A and 24B, respectively. A cross-sectional view of a portion of a representative device illustrating the separation chamber, permeable membrane, and electrode chamber is shown in FIG. 25.

A representative device including a focusing chamber is shown in FIG. 22. The embodiment illustrated in FIG. 22 includes side-by-side electrode arrays as shown in FIG. 21. Referring to FIG. 22, device 100 has basic components including first block 110 and second block 120 separated by intermediate sheets 130 and 140. Permeable member 416 is intermediate block 110 and sheet 140. Blocks 110 and 120 and intermediate sheets 130 and 140 are formed from machinable materials. Preferably, blocks 110 and 120 and intermediate sheet 130 are formed from PLEXIGLAS and sheet 140 is formed from TEFLON. In one embodiment, each component includes a plurality of apertures 212 that are coincident with the apertures of the other components when the components are assembled. Apertures 212 receive bolts 214 (see FIG. 23) for securing the assembled components and assist in sealing the assembly. As shown in FIG. 4, the components are secured through tightening nuts 216 on bolts 214.

To form the focusing chamber, first block 110 and second block 120 include troughs 112 and 122, respectively. Trough 122 includes the electrode arrays, each array comprising a plurality of electrodes 222. Sheets 130 and 140 include apertures 132 and 142, respectively. When the components are assembled, troughs 112 and 122 and apertures 132 and 142 are coincident and form a portion of the focusing chamber 410. Intermediate sheet 140 and block 110 is permeable member 416 which divides chamber 410 into separation chamber 412 and electrode chamber 414.

First block 110 includes conduits 114 and 116 which terminate in opposing ends of trough 112. Conduits 114 and 116 serve as inlet and outlet, respectively, for introducing a first liquid to and for removing the first liquid from the separation chamber. First block 110 further includes channels 118 which terminate in trough 112, which provide for eluting focused analytes from the device through offtake ports 30 (see FIGS. 20 and 21). Channels 119 also terminate in trough 112 and provide for introducing charged analyte and eluant to the separation chamber through inlet 418 and exiting eluant through outlet 420.

Second block 120 includes conduits 215 and 217, which terminate in opposing ends of trough 122. These conduits serve to introduce and exit liquid flow (e.g., coolant) through the electrode chamber. For embodiments of the device that include an electrode pair in addition to the electrode array, second block 120 further includes channels 218 which terminate in trough 122. Channels 218 receive electrodes 220 and 223, which like the electrode array, are in electrical communication with liquid in the electrode chamber when the device is in operation.

The assembled device is illustrated in FIGS. 23 and 24. Referring to FIG. 23, device 100 includes blocks 110 and 120 and sheets 130 and 140, and permeable member 16. Conduits 114, 116, 215, and 217, noted above, are illustrated along with connecting devices 124, 126, 224, and 226, respectively, which serve to connect the focusing chamber with its respective supplies. Inlet connection device 318 and outlet connecting device 320 are illustrated and communicate with channels 119 and separation chamber inlet 418 and outlet 420, respectively. Connector 224 leads to the device's controller and provides current to the electrode array. The representative device further includes first and second plates 170 and 180, respectively, which overlie the outward surfaces of blocks 110 and 120, respectively. Plates 170 and 180 can reinforce the assembly. Plates 170 and 180 are preferably steel plates.

Figure 25A:
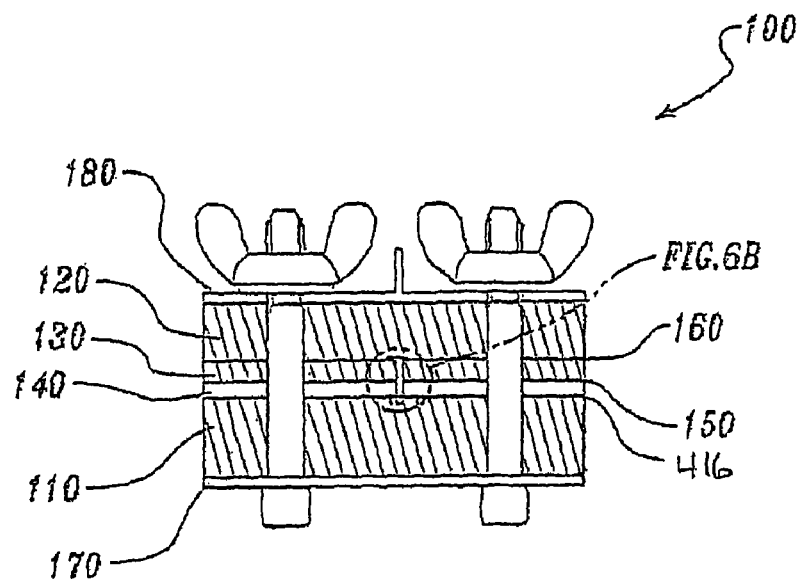
FIGS. 25A and 25B are views, partially in section, of the device of FIGS. 22A-22E, 23 and 24A-24B, in assembly, taken through line 6A-6A in FIG. 23 and line 6B-6B in FIGS. 24A and 24B, respectively.
Figure 25B:
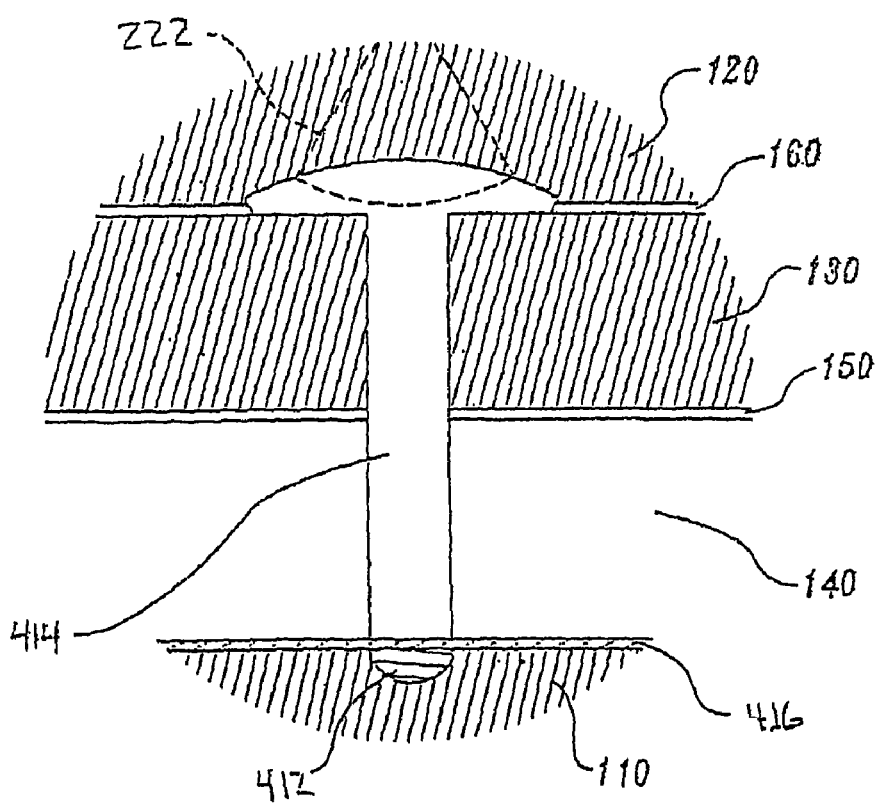
Figure 26A:
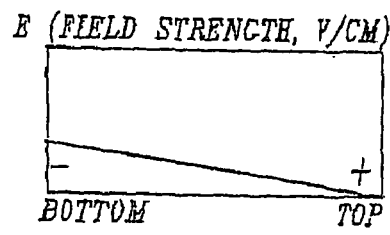
FIGS. 26A-26F present schematic representations and graphical representations of two approaches for conducting electric field gradient focusing in accordance with certain embodiments of the devices and methods disclosed here.
Figure 26B:
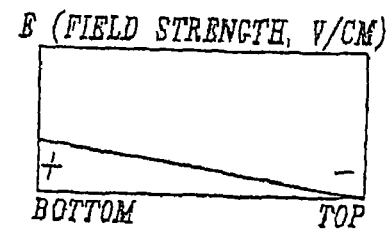
Figure 26C:
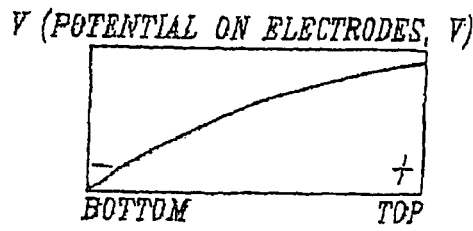
Figure 26D:
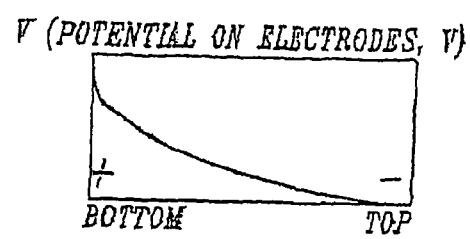
Figure 26E:
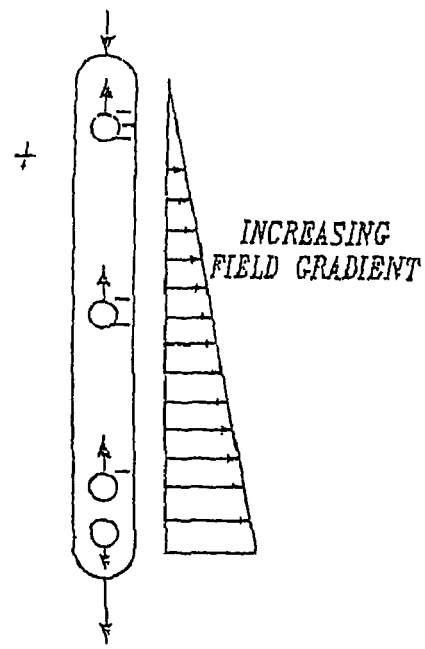
Figure 26F:
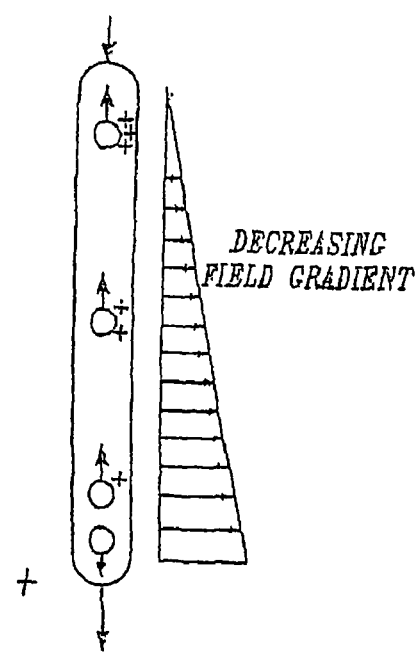

FIGS. 25A and 25B are cross-sectional views of a portion of the representative device described above, taken through line 6A-6A in FIG. 23 and through line 6B-6B in FIG. 24. Referring to FIG. 25B, device 100 includes blocks 110 and 120 and sheets 130 and 140. Intermediate block 110 and sheet 140 is permeable material 416 which divides the focusing chamber into separation chamber 412 and electrode chamber 414. Sheet 140 serves as a spacer for adjusting the depth of electrode chamber 414 and, accordingly, the thickness of sheet 140 can be varied as desired. Sheet 140 is a resilient sheet and also serves to seal block 110 to the remaining components of the assembly.

Intermediate sheet 140 and sheet 130 is sealant layer 150. Sealant layer 150 includes a sealant that effectively joins sheet 140 to sheet 130 and prevents liquid from escaping the electrode chamber. Intermediate block 120 and sheet 130 is adhesive layer 160. Adhesive layer 160 includes an adhesive that effectively joins sheet 130 to block 120.

A representative device including a focusing chamber was formed from two blocks of $15 \times 6 \times 1.2$ cm$^3$ PLEXIGLAS and a 0.3 cm thick TEFLON spacer. The front block, which houses the separation chamber (i.e., separation column or electrochromatography column), has a trough $8 \times 0.1 \times 0.05$ cm$^3$ machined into it, the rear block, which houses 50 controllable electrodes, has a trough $6.4 \times 0.3 \times 1.5$ cm$^3$, and the spacer has a $6.5 \times 0.2$ cm$^2$ slot machined through it. The trough in the front block is isolated from the spacer by the permeable material. The rear trough and slot admit a recirculating buffer that can have the same composition as the running (i.e., elution) buffer, acts both as coolant, anolyte, or cathalyte, and removes electrolysis products from electrode array. Because the coolant is in contact with the separation column via a permeable material, the coolant can also be used to dialyze the running buffer to exchange salts or other low molecular weight analytes. The coolant inlet and outlet are shown in FIGS. 23 and 24.

Outside of the focusing chamber, the coolant buffer is circulated through a glass heat-exchange reservoir submerged in an ice bath. From here the coolant is introduced into the bottom of the focusing chamber and is passed over the electrodes at about 15 mL/s using a centrifugal pump (Cole-Parmer). A syringe pump controls the flow of the running buffer through the chamber at 15-150 L/h. The running buffer enters the chamber in the upper flow inlet on the front face and exits from the lower flow outlet on the front face. All lines are PEEK with flangeless fittings; sample is loaded through a 10-L loop on a six-port injection valve (Upchurch).

The 50 chamber electrodes are made from 0.25-mm-o.d. platinum wire (Aldrich Chemical), mounted in the rear PLEXIGLAS block with a 0.05-in. pitch, and are connected to a SCSI ribbon cable using SMS-series microstrips (Samtec). Each of the SCSI leads is connected to its own printed-circuit (PC) monitor/controller board mounted on the wire wrap motherboard. Each monitor/controller board is segregated into three areas: high voltage, monitoring, and control. The high-voltage area isolates the chamber electrode voltages, which can be as high as 600 V, from the relatively sensitive electronics used to measure and adjust the electrode voltages. The monitor area of each PC board scales down the electrode voltage by about 100× and sends this signal to a commercial thermocouple board which digitizes the signal before sending it to the computer. The computer scans all 50 electrodes, compares these readings with the programmed profile, and sends a digital signal to a set of 50 DACs which tell the optical isolators to adjust the effective resistance of high-voltage line to reduce the departure of the measured electrode voltages from the programmed voltage profile. A complete scan/control cycle of the 50 controllers is taken every second. Each of the 50 controllers is mounted vertically on a wire-wrapped motherboard; power to the controllers' motherboard is drawn from the computer. A 600-V power supply (Xantrex) provides current to the column's 50 high-voltage electrodes via the 50 voltage controllers.

The device is operated as follows. After the recirculating coolant has reached operating temperature and the separating chamber has been cleaned, e.g., with 7 M urea, and equilibrated with running buffer, 10 L of sample is injected into the chamber using a standard sample loop. Before analyte reaches the outlet, the controller is booted using a default voltage pattern and the power supply is brought up to a voltage in the range 200-600 V. The operator then selects the initial electric field gradient, and the computer program adjusts the electrode voltages until this gradient is attained, typically less than 5 min. from a "cold" start.

Where the electrophoretic mobilities or charge to mass ratios of two analytes are sufficiently close, the electric field gradient alone may be insufficient to separate them. Without wishing to be bound to any theory, it is currently understood that analytes are separated by the methods and devices disclosed here on the basis of their molecular weights by effectively applying different hydrodynamic forces to differently-sized molecules; that is to say, due to the sieving affect of the molecular sieve, molecules of different sizes effectively are subject to different hydrodynamic forces for a given flow rate of first liquid.

Although the above examples illustrate the use of linear electric field gradients, where an electrode array is employed the software can be modified to allow point-by-point adjustment of the field including reversing the field to aid in elution of fractionated bands, isolating and mobilizing a single protein band, or stepping the gradient to improve processing capacity. In addition, because the electronic controller and the technique are largely independent of chamber capacity, there is no reason it cannot be applied at larger or smaller scales.

The dynamic electric field gradient focusing provided by preferred embodiments of the methods and devices optionally relies in part on field gradient control, which includes hardware and software. Representative gradient control hardware and software are discussed below.

Figure 29:
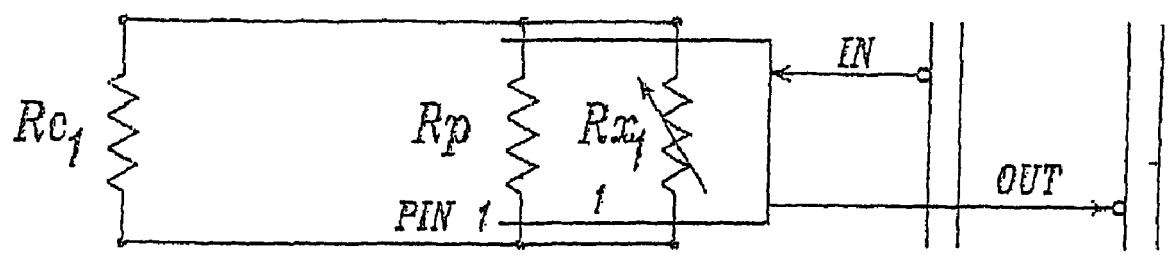
FIG. 29 is a schematic representation of the resistance between two adjacent electrodes in another embodiment of the methods and devices disclosed here.
Figure 30:
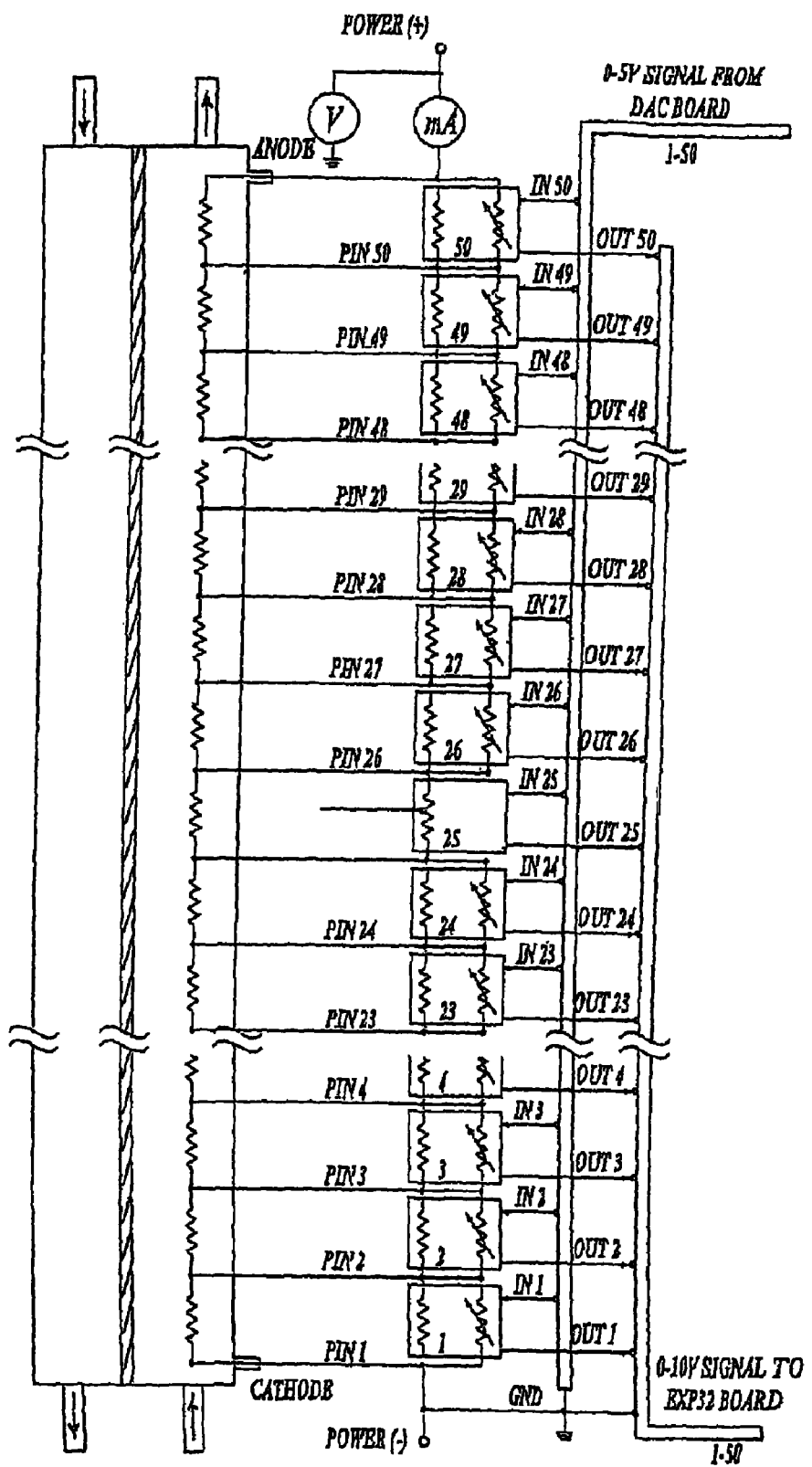
FIG. 30 is a schematic diagram of a representative electric field gradient focusing gradient control model of an embodiment of the methods and devices disclosed here.

The control circuits are designed to manipulate the field gradient by adjusting the effective electrical resistance between each two adjacent electrodes (see FIG. 29). In one embodiment, each pair of electrodes is connected to one of the 50 controller units. A schematic of such an embodiment is shown in FIG. 30, in which the blocks with dash line frames are controller units and each of the controller units handles the data acquisition and the resistance control of two adjacent electrodes.

The electrical resistance between two adjacent electrodes $R_i$ is determined by the sum of the resistance of three parallel resistors, $Rc_i$, $Rp_i$, and $Rx_i$. Note that the buffer between electrodes is considered as a resistor $Rc_i$.

$$R_i = \frac{Rc_i \cdot Rp_i \cdot Rx_i}{Rc_i \cdot Rp_i + Rc_i \cdot Rx_i + Rp_i \cdot Rx_i} \quad (1)$$

The resistors $Rp_i$ are used for protective purpose and have 1M resistance. Because $R_p \gg Rc_i$, $R_p \gg Rx_1$. Equation (1) can be simplified as $$R_i = \frac{Rc_i \cdot Rx_i}{Rc_i + Rx_i} \quad (2)$$

By changing each $Rx_i$, the circuits adjust each $R_i$ indirectly. By Ohms Law, the potential drop between two electrodes is determined by the resistance between them if the total current going through is constant. The potential drop between the two adjacent electrodes is given by $$V_i = V_{total} \cdot \frac{R_i}{\sum_{i}^{50} R_i} \quad (3)$$

Since the field strength is proportional to the potential drop with the electrodes equally spaced, we can manipulate the field strength point by point by adjusting each $Rx_i$, independently.

$$E_i = \frac{V_i}{d} = \frac{V_{total}}{d} \cdot \frac{R_i}{\sum_{i}^{50} R_i} \quad (4)$$

where d is the distance between the two adjacent electrodes. An electric field gradient in any shape, linear or nonlinear, continuous or stepwise, can be produced with a limitation to the conductivity of the buffer. Note that the resistance between two parallel-connected resistors is always less than any one of them, in other words, $R_i < Rc_i$ must be satisfied.

There is more than one group of $R_i$ that satisfies Equation 4, in other words, different groups of $Rx_i$ can be used to establish the same field gradient with the total current going through the chamber arbitrarily. There is no unique equilibrium state. To solve the problem, a small modification to unit No. 25 is made by disabling its control function and replacing $Rp_{25}$ with a 5 k resistor. The total current going through the chamber was fixed, and given by $$I = \frac{V_{25} \cdot Rp_{25} \cdot Rc_{25}}{(Rp_{25} + Rc_{25})} \quad (5)$$

$V_{25}$ has a unique value for a specific field gradient, and can be calculated from the total potential drop across the chamber. $Rc_i$ is determined by the conductivity of the buffer. Therefore, there is a unique value of $Rx_i$ that satisfies Equation 4.

Figure 27:
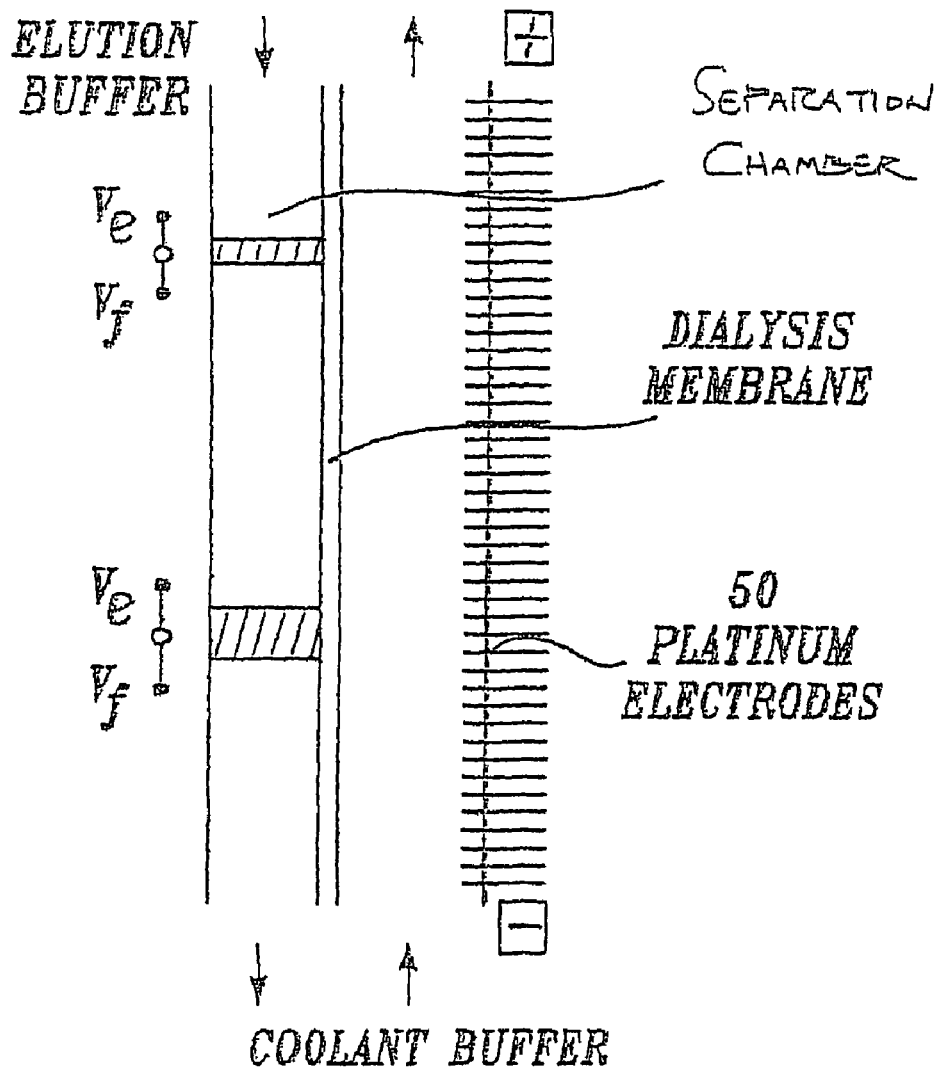
FIG. 27 is a schematic drawing of another embodiment of a device in accordance with the present disclosure.
Figure 28A:
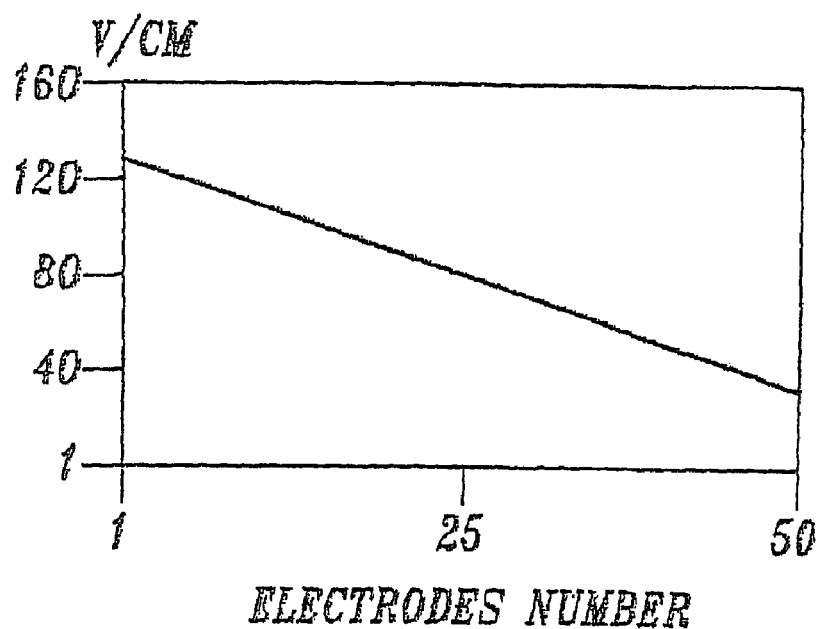
FIGS. 28A and 28B each is a graphical representation of the field strength profile and potential profile, respectively, of a linear field gradient (15.5 v/cm$^2$) in accordance with another embodiment of the methods and devices disclosed here.
Figure 28B:
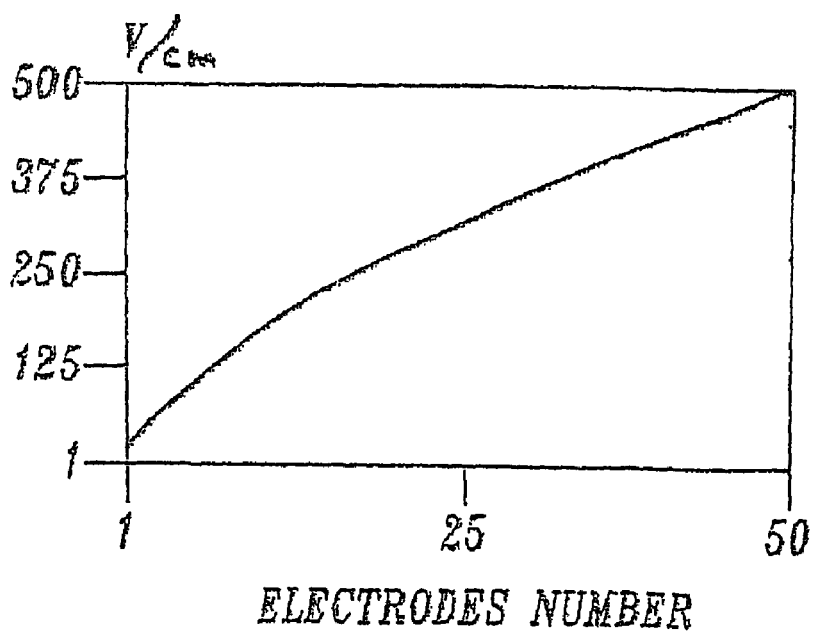

In certain preferred embodiments, dynamic electric field gradients are created by a computer-controlled external circuit, which manipulates the field strength between each pair of adjacent electrodes, as exemplified in FIG. 27. Varying field strength along the separation chamber can thus be achieved. FIGS. 28A and 28B are graphical representations of linear electric field gradients so generated.

Figure 31:
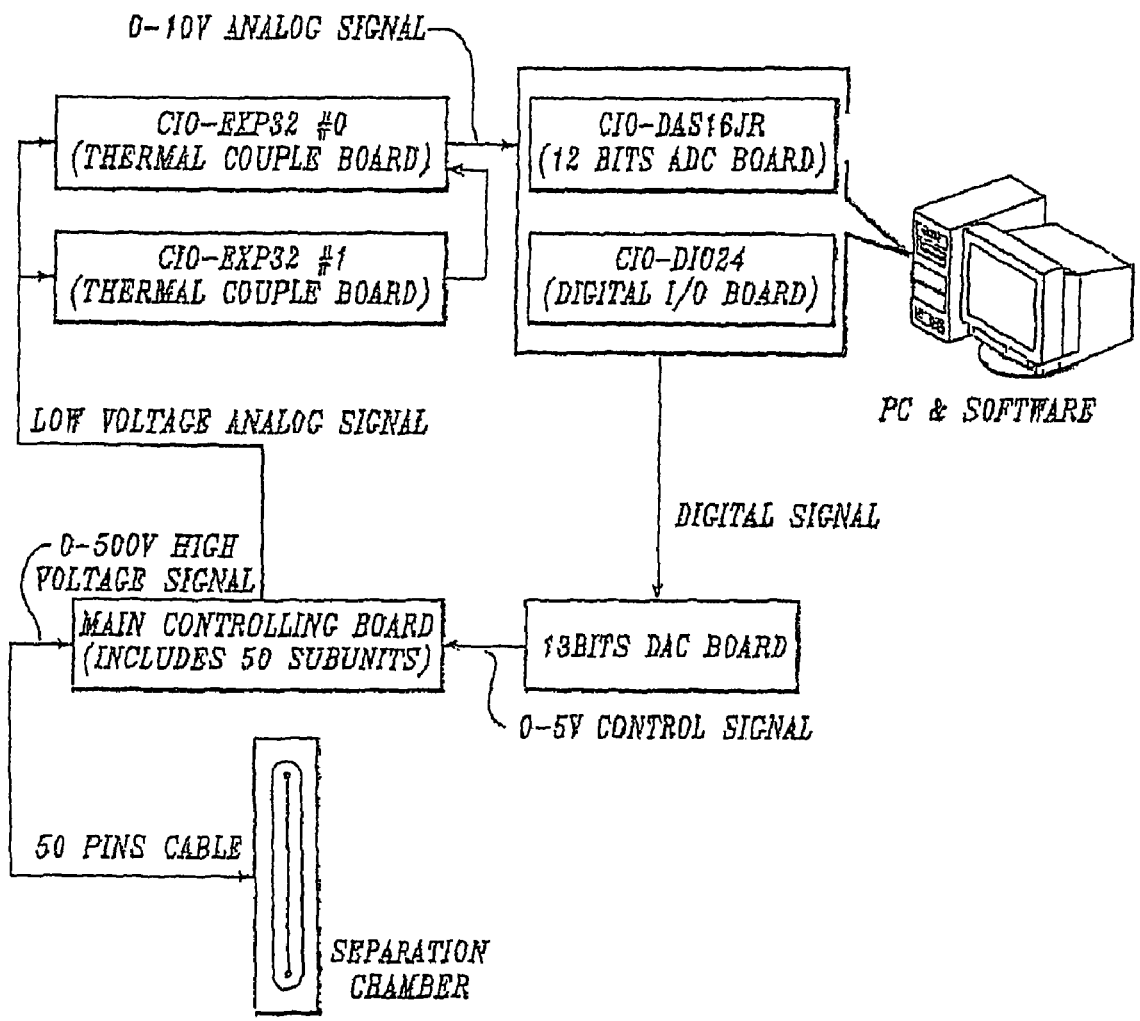
FIG. 31 is a schematic diagram of a representative electric field gradient focusing gradient control circuits.

Representative gradient control circuits are shown schematically in FIG. 31. The blocks represent electronic boards, the lines represent standard ribbon cables. Referring to FIG. 31, the PC monitor/controller board and the 13 bit DAC board were built in our laboratory. Some modifications have been made for better performance. The data channels between the two CIO-EXP32 boards and the CIO-DAS16Jr boards are programmed rather than being physically connected. CIO-DAS16Jr and CIO-DIO24 are plugged into extension slots of the PC. The two thermocouple boards CIO-EXP32, the 16-channel ADC board CIO-DAS16/Jr and the 24-channel Digital I/O board CIO-DIO24 were purchased from ComputerBoards, Inc. Standard SCSI ribbon cables are used to connect all the boards. There are 50 controller units plugged into the mother board. Each unit corresponds to one pair of electrodes. The whole system was grounded to protect the circuits from unexpected shock.

Figure 32:
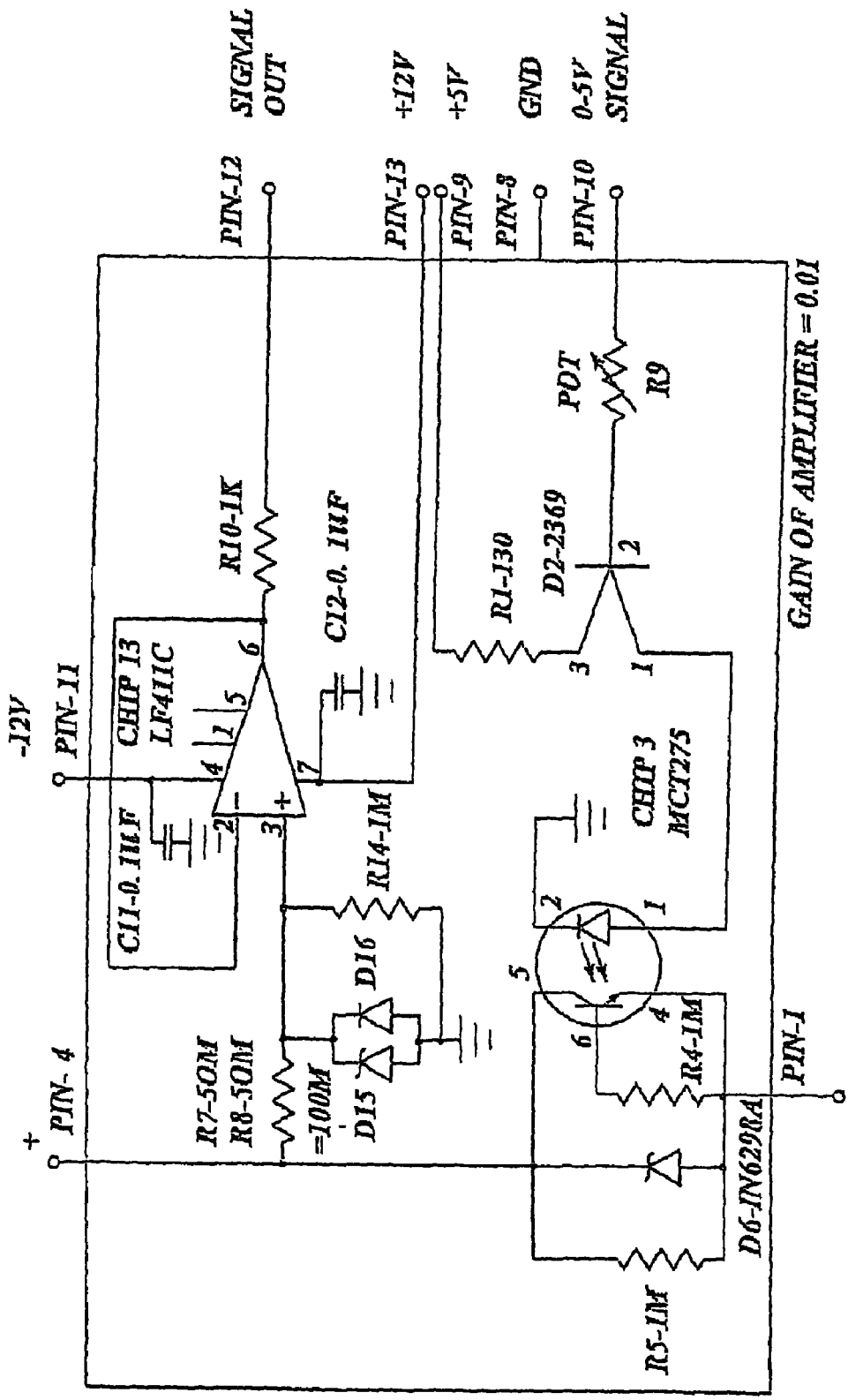
FIG. 32 is a circuit diagram of a representative controller unit.
Figure 33:
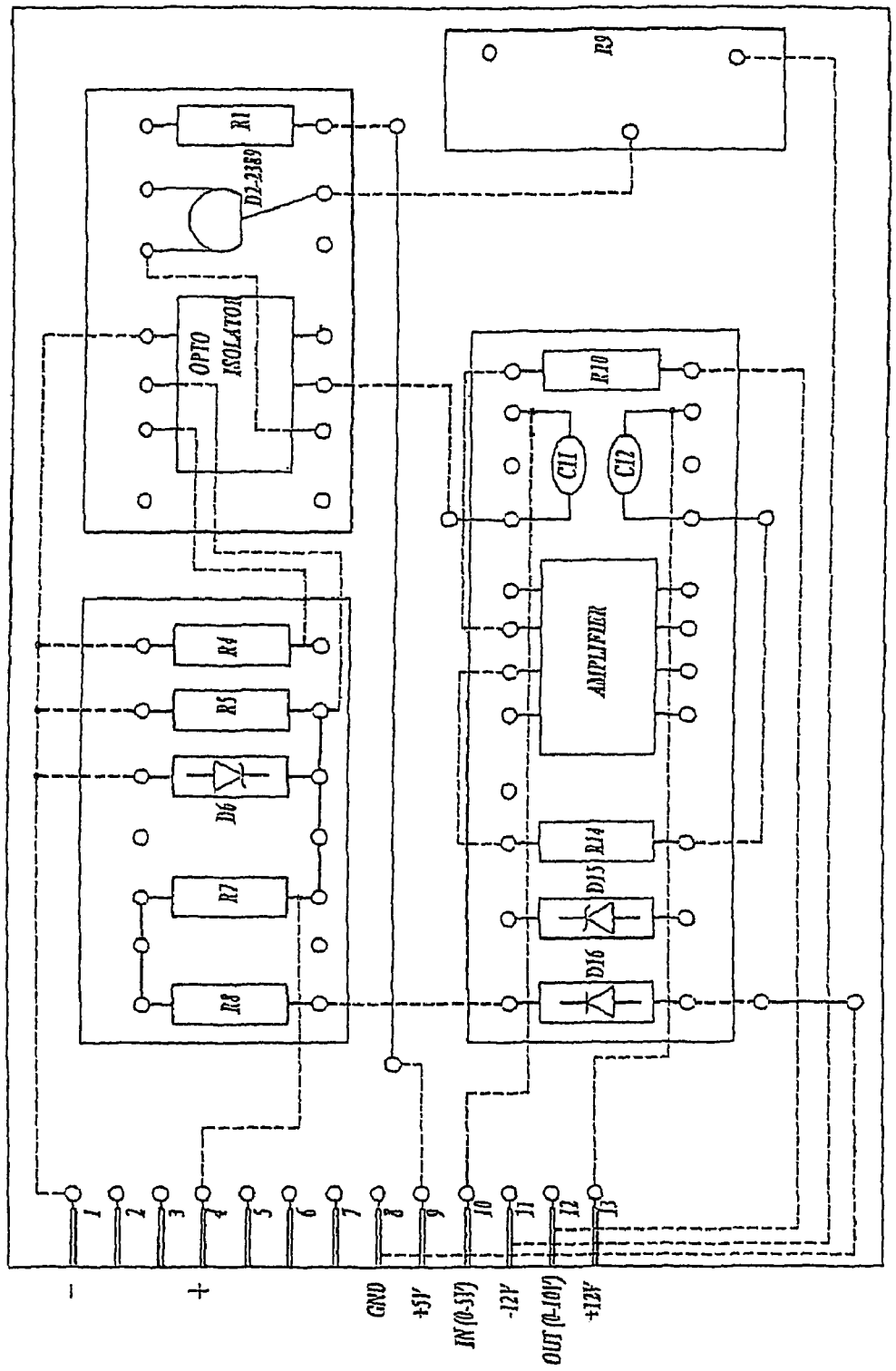
FIG. 33 is a circuit diagram of a representative controller unit.
Figure 34:
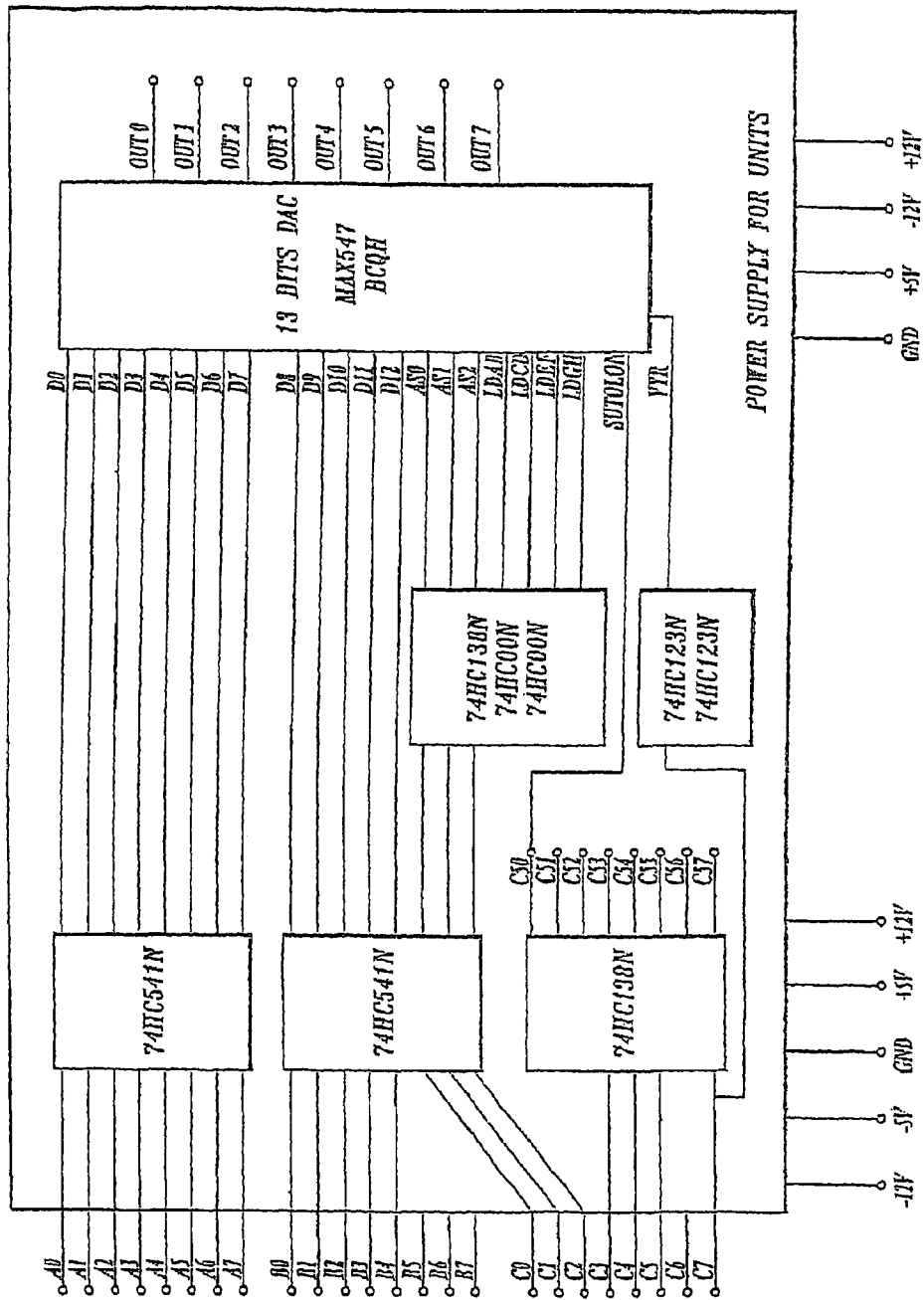
FIG. 34 is a schematic illustration of a representative DAC board circuit diagram illustrating connections.
Figure 35A:
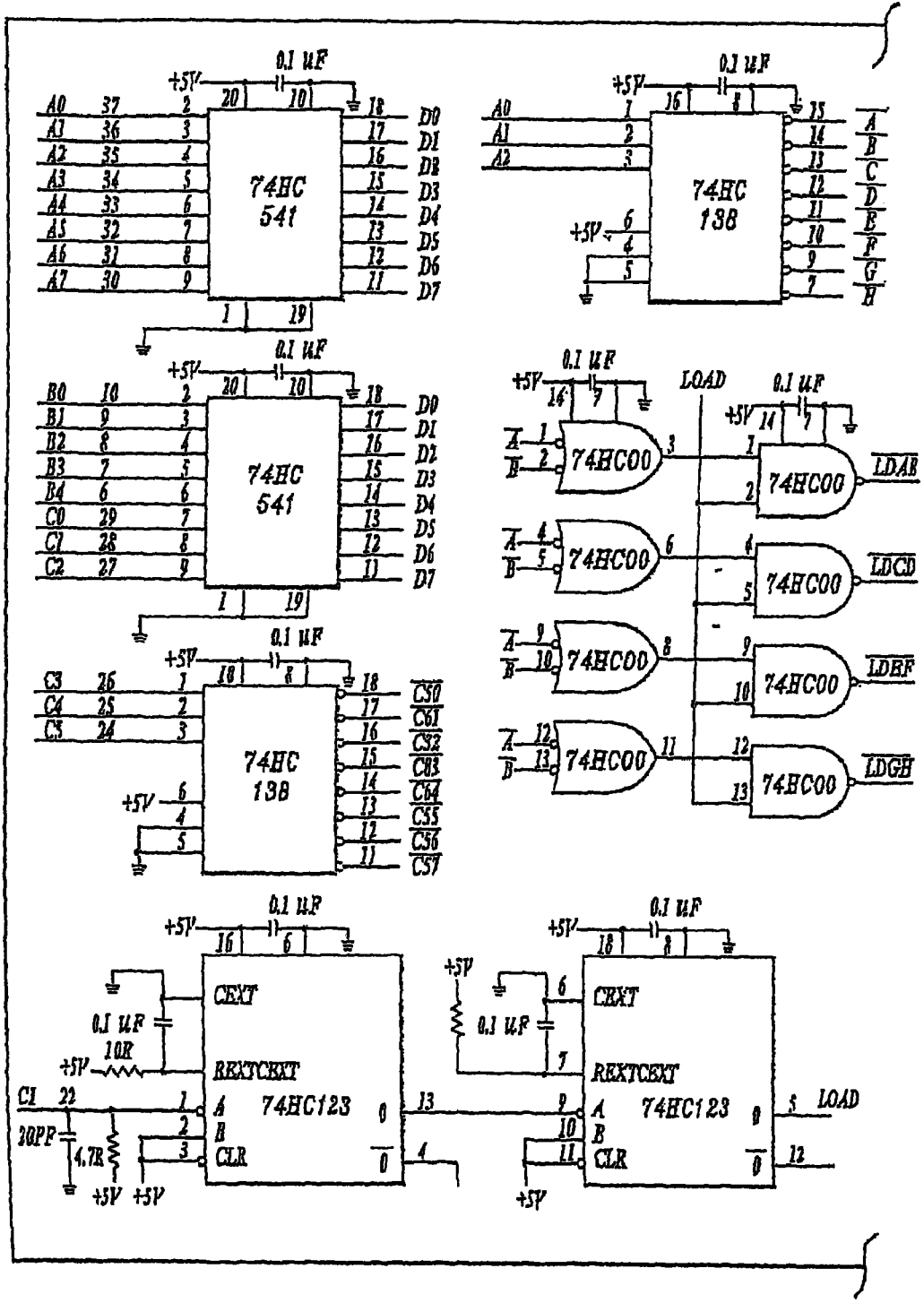
FIGS. 35A and 35B are schematic illustrations of a representative DAC board circuit diagram illustrating components.
Figure 35B:
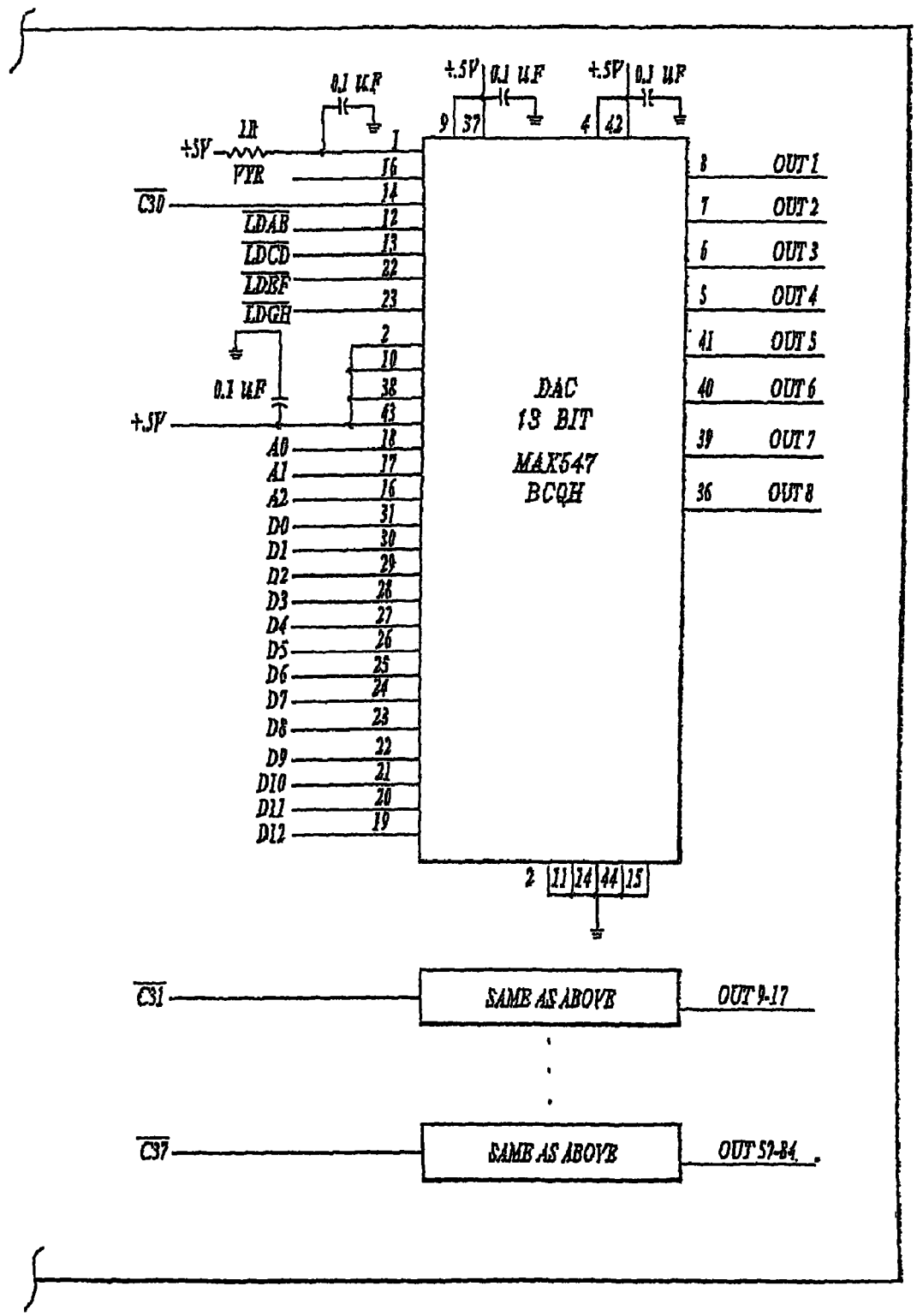

The gradient control is accomplished with PC-controlled circuits, diagrammed in FIG. 32, which are composed of electronic circuit boards. Pin 1 and 4 are connected to electrodes and neighboring units. The electrical potential on the electrode is reduced by 1/100, then enters amplifier LF411C where the load of the signal is increased. The signal is then sent to EXP32 board through pin 12, and the control signal (pin 10, 0-5 V) from the DAC board adjusts the current going through the optical isolator MCT275. A circuit diagram of the controller unit is shown in FIG. 33. A logic diagram for circuit diagram for ADC board is shown in FIG. 34. A circuit diagram for the ADC board with components identified is shown in FIG. 35. The circuits scan all 50 electrodes and scale the signals down by 1/100. Then the signals were sent to ADC board where 0-10V analog signals are digitized. The computer compares these readings with the programmed gradient, then sends its commands in digital signals to DAC board via the Digital I/O boards. In the DAC board, the command signals are converted to 0-5V analog signals, then sent to the 50 units on the PC monitor/controller board. Those units adjust the current going through the units, or we can say change the values of resistance $Rx_i$. Note that the $Rx_i$ do not exist physically, and they are the resistance to current going through the chip MCT275, an optically isolated controller. The scan/response cycle for the circuits is set at about 0.5 sec, and could be adjusted by the program.

A 600V DC power supply (Xantrex) supplies power to the chamber. The power to all the boards is supplied by the computer. As noted above, the second chamber can include more than one electrode array. For example, two electrode arrays can be associated with a single separation chamber in a configuration in which the separation chamber is positioned in between the two arrays. Similarly, the second chamber can include, for example, four arrays positioned about a separation chamber in a quadrupole-type configuration. Other preferred embodiments can include more than one second chamber, each having one or more electrode arrays.

Figure 36:
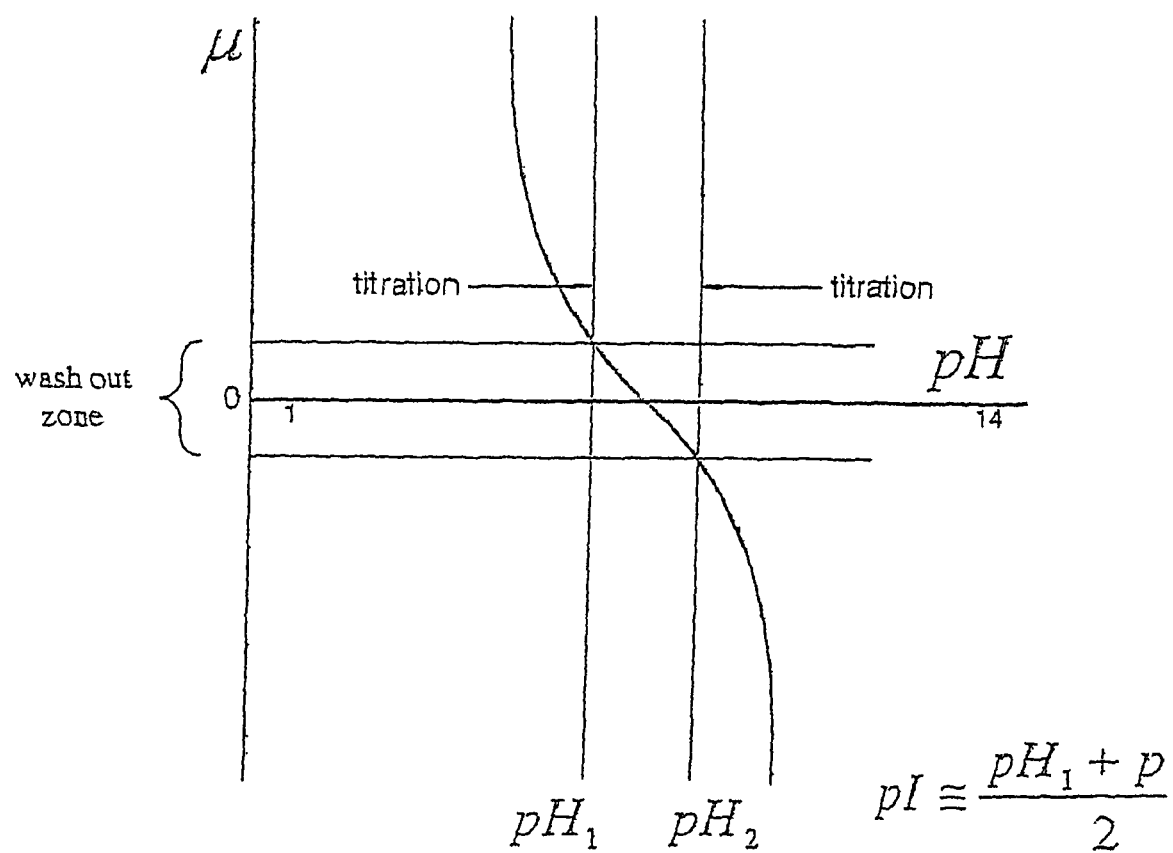
FIG. 36 is a graphical representation of the relationship between electrophoretic mobility and pH for a charged analyte.
Figure 37:
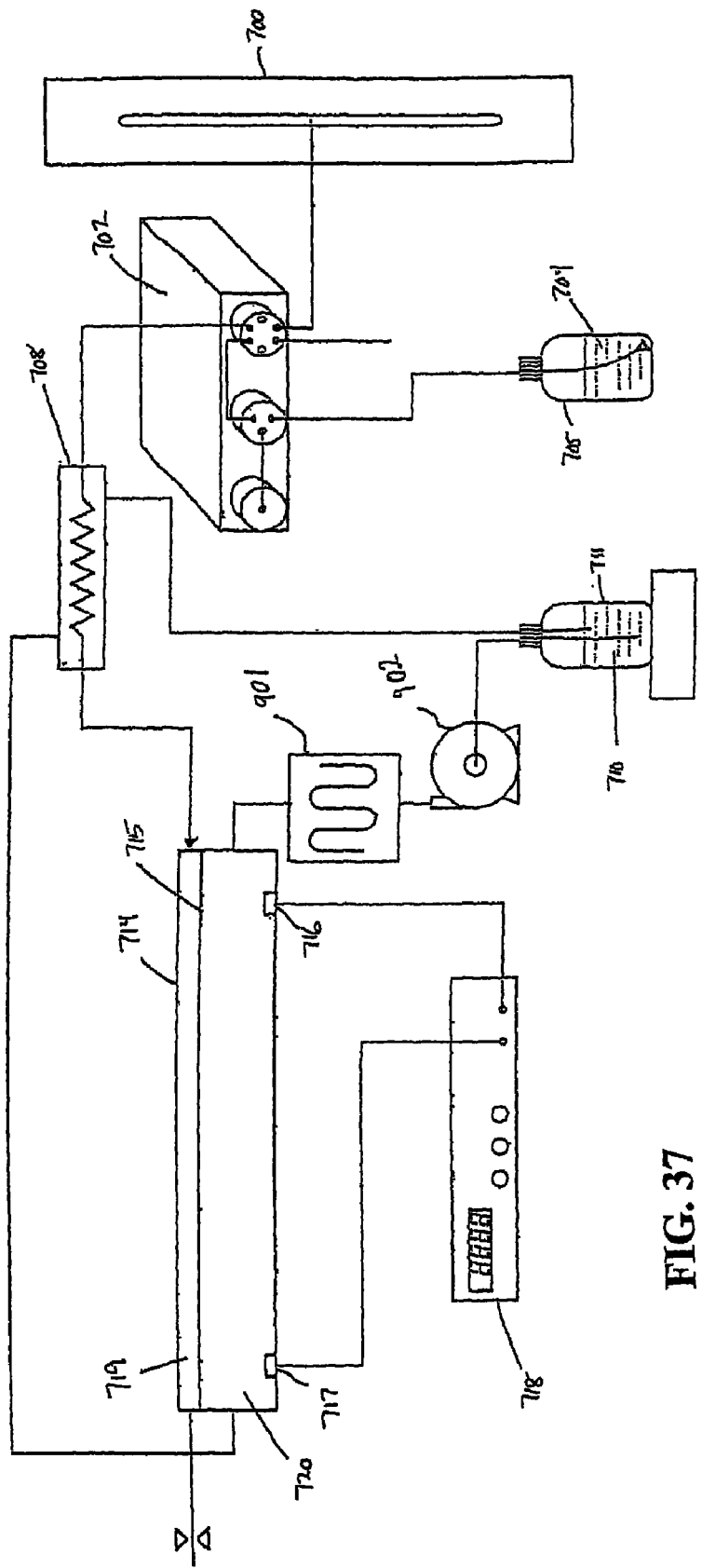
FIG. 37 is a schematic illustration of a system in accordance with a preferred embodiment.

Returning now to a discussion of the titration aspect of the methods and apparatus for determining the isoelectric point of a charged analyte, FIG. 36 illustrates the typical relationship between buffer pH and electrophoretic mobility of a molecule. As the pH of the system approaches the isoelectric point of an analyte, the electrophoretic mobility of the analyte will tend to zero. Thus, it is possible to determine the pI from the μ-pH curve. For most molecules, the μ-pH curves are symmetric about the pI and measurement of the mobility over the entire pH range allows elucidation of the pI value. In certain preferred embodiments, measurements need only be taken on one side of the μ-pH curve to enable elucidation of the isoelectric point. In certain preferred embodiments, the pI can be estimated from two data points, which bracket the isoelectric point.

Without wishing to be bound to a theory, it is presently believed that a charged analyte can be subjected to an electric field, thereby inducing an electrophoretic velocity in one direction. The field-induced velocity is countered in the opposite direction by a hydrodynamic velocity, typically resulting from pumping buffer through the chamber, such that the analyte is held or focused as a band at or about a single location in the chamber. While holding the molecule in the chamber, the pH of the system is incremented until the position of the band shifts within the chamber. Changes in the pH will result in protonation or deprotonation of target molecules, thereby affecting the entities' overall surface charge and electrophoretic mobility. The pH can be changed until a point is reached where the magnitude of the entity's surface charge becomes too low for the electric field gradient to counter the hydrodynamic flow, at which point the molecule elutes or washes out from the electric field. By measuring the changes in electrophoretic mobility and in pH, the isoelectric point can be determined. In certain preferred embodiments, "wash-out" point $pH_1$ corresponding to the upper bracketing pH value that brackets the isoelectric point is determined by adjusting the buffer pH up from a low starting pH, and "wash-out" point $pH_2$ corresponding to the lower bracketing pH is determined by adjusting the buffer pH down from high starting pH. In determining these two points, the magnitude of electric field and buffer flow rate are held equal for both titrations, with the fields having opposite polarities due to the charge states of the molecules. The average of $pH_1$ and $pH_2$ is considered to be the pI of a particular molecule. Since there are two independent titration procedures involved in this embodiment, the data can either be collected in parallel or serial fashion. Regardless of the instrument configuration, the electric field and flow rate are maintained at same magnitude.

More accurate pI determination is achievable by narrowing the mobility "window", the pH segment where the molecule does not possess a large enough mobility to be held in the chamber and is instead washed out. Therefore, in practice, a high electric field and a low flowrate are preferred. Note, the magnitude of the electric field is limited by the heat-dissipation capability of the chamber and the buffer flowrate affects the maximum analysis throughput.

In accordance with one exemplary embodiment, a substantially planar electrophoresis device in accordance with those disclosed herein has the following attributes:

Applied voltages up 300 V. This corresponds to a maximum electric field of 200 V/cm.
  Electrode buffer flowrate of 0-20 mL/min.
  Separation chamber buffer counterflow flowrate 0-10 microliters/min
  Buffer conductivity 0-1 S/cm. The conductivity of 20 mM Tris-phosphate at pH 7.25 is approximately $1.025 \times 10^3$ microSiemens/cm.
  Dimensions of the electrode chamber are 1 mm wide×0.5 mm deep×2.54 cm long.
  Depth of the separation chamber is 3.2 mm.
  Distance between the main pair of electrodes is 2.54 cm.
  Width of the separation chamber is 1.6 mm at the most narrow point and 1.6 cm at the widest.
    The focusing chamber has an active region of from 1 cm to 12.7 cm for varying scales of the device, e.g., 2.54 cm for the other attributes listed here.
    The configured chamber is defined by side walls (i.e., walls substantially perpendicular to the plane of the porous, conductive membrane) with a hyperbolic shape resulting in a linear electric field gradient (see FIGS. 1 and 2). The chamber shape can be tailored to generate a specified electric field (e.g. non-linear) to perform a custom separation.
  A single separation chamber suitable for focusing either positively or negatively charged molecules.

The following are adaptations of the device configuration and the application identified:

A single chamber with a switchable power supply to select focusing either positively or negatively charged molecules.
  Two chambers configured in a serial fashion, at least one of which is in accordance with the devices disclosed herein, with a three-way diverter valve positioned at an intermediate point, to allow "filtering" and isolation of target molecule(s). (See, e.g., FIG. 3.)
  Two chambers, at least one of which is in accordance with the devices disclosed herein, configured in a serial fashion to focus both positive and negative molecules simultaneously.

The device can be constructed of any suitable material that is compatible with either aqueous or organic solvents, or both, depending on the intended application and environment of use. Exemplary materials include PEEK, TEFLON, acrylic, etc. Thus, for example, the separation chamber can be etched or otherwise formed as a configured groove or channel in a substrate of such material. The membrane seated against the substrate completes the separation chamber, leaving the ends open (preferably valved) for flow. The device may be constructed of material that is optically clear over the UV-Vis-IR spectral range to permit imaging or detection of isolated molecules in the chamber. This may include UV transparent acrylic, quartz, TEFLON AF, etc.

Detection strategies for such devices may also include monitoring the entering and exiting streams for tracking of materials. These would be considered point detectors. If the device is constructed of optically clear material, as mentioned above, point detectors could be spatially distributed along the length of the chamber, as opposed to imaging the entire chamber. Point detectors may be distributed throughout the system for overall tracking of material (e.g., at the exit of a switching valve to monitor routing of peaks).

As disclosed and described above, the electrophoresis device uses a porous layer to separate the electrode chamber from the separation chamber. The porous layer may be a dialysis membrane, ceramic membrane or other porous material that allows conduction of ions and electrical current. The molecular weight cut-off (MWCO) for the porous layer may range from 100-30,000 MW. Typically, small molecule applications may require a porous layer having a 100-200 MWCO and proteins applications may require a porous layer having a MWCO>1000.

An exemplary system in accordance with the present disclosure may employ auxiliary equipment such as any or all of the following:

- A dynamic power controller unit to provide a supply of up to 300 V on 25 independently controlled channels, the user optionally having full control over voltage settings, with built in data acquisition for recording of voltage settings.
- Capillary-scale UV-Vis flowcell to allow UV-Vis interrogation of streams for performing absorbance spectrophotometry across the spectral range 200-1100 nm.
- UV-Vis light source with fiber-optic coupling capability to provide illumination energy for absorbance spectrometry over the range 200-1100 nm.
- HTSL-1100 microfluidic sample loader to provide the ability to automatically inject microliter quantities of sample into a precision controlled flow stream with flowrates of 1-20 microliters/min.
- A GUI software control bench to interface the HTSL for flexible control of sample loader operations.
- A suitable computer, such as, for example, a Pentium IV 2.0 GHz computer, 512 MB Ram, 30 GB HD, CD-RW to provide computational power to execute and manage the HTSL and spectrometer software and data acquisition.

A preferred device configuration is shown in FIG. 27. FIG. 27 includes a DFGF device 700 for separating and focusing the charged analyte prior to determining the isoelectric point. The sample is eluted from the DFGF device and flowed into a sample loop such as an HTSL 702 where it is injected into a carrier liquid 704 that is pumped from a carrier liquid reservoir 705. The charged analyte may be eluted from the DFGF device using either pressure-driven or electrophoretic processes. The carrier liquid containing the charged analyte is flowed into a microdialyzer 708 where the pH of the carrier liquid is incremented by titrating solution 710, which is pumped from titration reservoir 711. The carrier liquid flows into the titration chamber 719 of a device 714 in accordance with any of the device aspects and embodiments presented herein, which comprises electrodes 716 and 717 for generating the electric field gradient. The electrode chamber is separated from the titration chamber by permeable material 715. The electrodes are monitored and adjusted by an HV power supply 718, which can be itself monitored and adjusted by an operator or by computer control, not shown. The system as shown further comprises a thermoelectric cooling, vacuum degassing module 901 and a pump 902.

In practice, the titrating solution, which also serves as a purge buffer flowing through the electrode chamber 720 flowing through the electrode chamber undergoes continuous titration to alter the pH value of the overall system. The pH of the system is monitored to control rate of titration and correlation of the "wash-out" point with pH. The carrier liquid entering the sample chamber is dialyzed against the titrating solution through an inline dialysis module to ensure coincident pH conditions for the purge and cross-flow streams. Visualization of the titration process can be performed in the chamber or at the outlet of the titration chamber. Modes of detection may include those discussed above.

Figure 38:
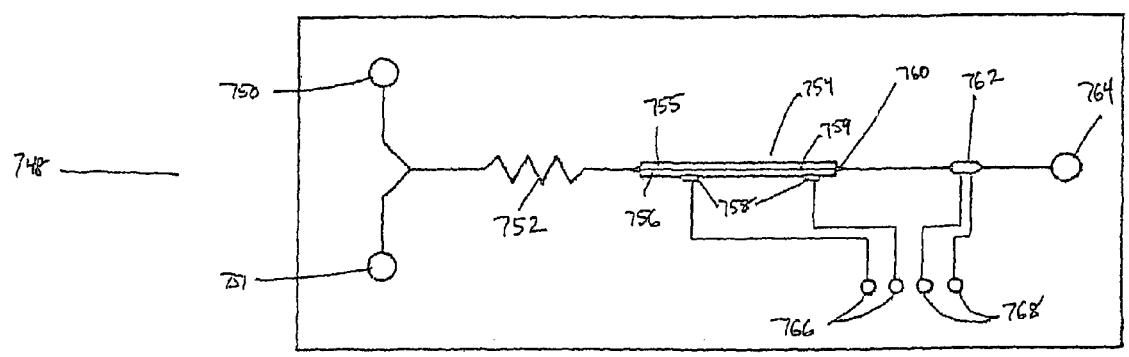
FIG. 38 is an schematic view of a system in accordance with another preferred embodiment.

An alternative device for pI determination is illustrated in FIG. 38. The device comprises a microfluidic chip 748. The carrier liquid containing the charged analyte enters through the carrier port 750, and the titrating solution through titrating solution port 751. The carrier liquid and the titrating solution are mixed in an online mixer 752 and then flow into the titrating chamber 755 of a device 754 in accordance with the any of the aspects and embodiments presented herein. Electrodes 758 are contained in electrode chamber 756, which is separated from the titration chamber by permeable material 759. An analyte band detector 762 is located just after the outlet 760 of the titration chamber. After eluting from the titration chamber and being sensed by the analyte band detector, the analyte exits the chip through exit port 764, from which the analyte can be quenched and returned to the chip for a second run, flowed onto a second such chip for a second run, or flowed elsewhere for further analysis or use. Electrodes 758 and analyte band detector 762 are electrically connected to connection posts 766 and 768, respectively, which can be connected to appropriate monitoring and control apparatus as required.

Devices in accordance with this embodiment preferably employ microfluidic technology. Using a microfluidic device simplifies the titration system by eliminating the need for a recirculating purge buffer and an inline dialyzer. At small length-scales, the voltage requirements are reduced, while generating equivalent electric fields. Also, the heat dissipation challenges faced with larger scale devices become insignificant in the microdevice configuration. In practice, the titration of buffer pH can be carried out by mixing on-chip the two buffer streams. Measurement of pH and detection of sample peaks can be accomplished by integrating advanced detectors directly into the device flow channels.

Figure 39A:
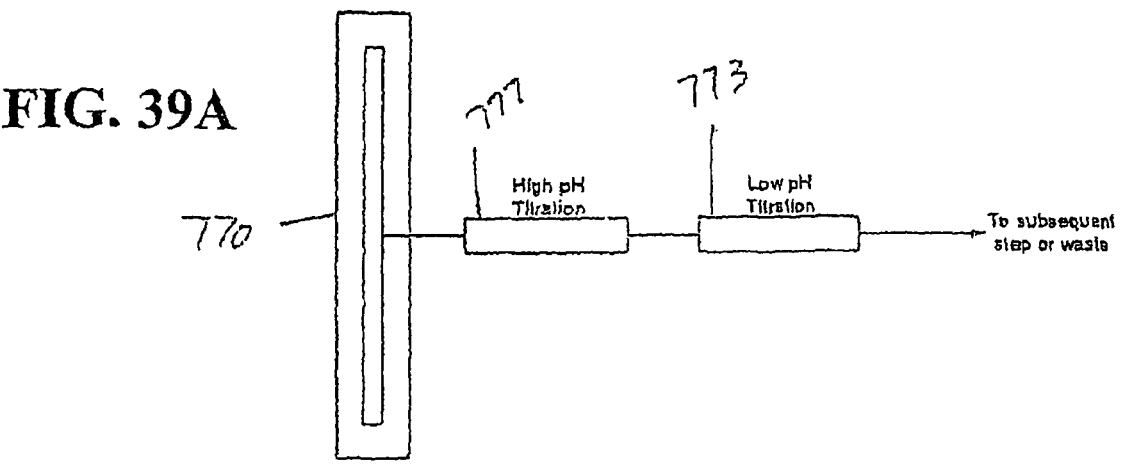
FIGS. 39A-C are schematic illustrations of systems in accordance with alternative preferred embodiments.
Figure 39B:
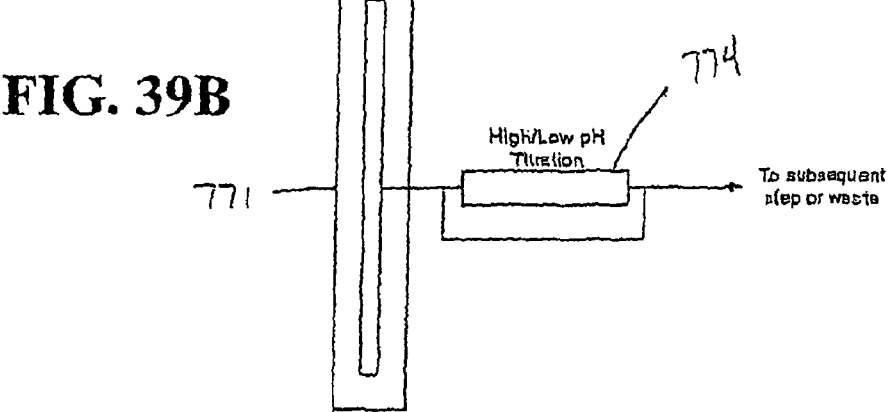
Figure 39C:
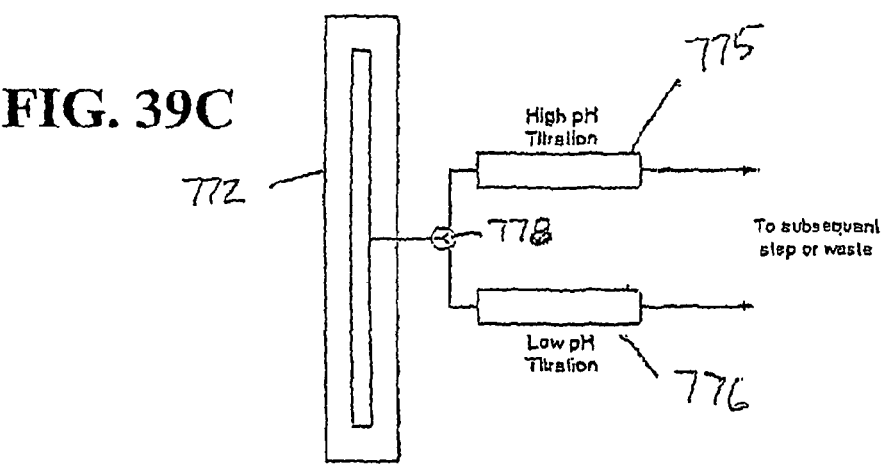

The titration procedures in certain preferred embodiments can be performed in either a serial or parallel fashion. FIG. 39A-C presents a conceptual view of possible system layouts. The titration of samples for determination of a pI could be performed in a serial (FIG. 39A), a serial using recycle (FIG. 39B), or a parallel fashion (FIG. 39C). In each of these figures, a DFGF device 770, 771, 772 provides separation and focusing of the charged analyte and pI determination is performed on one or more devices 773, 774, 775, 777 and 778 in accordance with aspects and methods presented herein. A sample splitter 776 in FIG. 29C serves to split a sample of charged analyte into two portions which then proceed to the pI determination in separate devices.

In terms of a serial approach to determination of a pI, a sample is eluted from a separation device such as a DFGF device and injected into the first of two chambers, as shown in FIG. 39A. Titration of the buffer pH is carried out from a high value down to the "wash-out" point, at which time the sample is eluted to the second chamber. At an intermediary point between the two chambers, the pH of the sample has to be quenched to a low value, thereby inducing a surface charge of opposite polarity to the first titration. The quenching step is necessary to avoid sweeping the target molecule through the second chamber. In the case of FIG. 39B, the sample is eluted from the chamber and recycled for re-injection. Prior to re-injection, the buffer composition of the system has to be exchanged to conditions appropriate for the second titration. FIG. 39C illustrates a parallel processing configuration for the titration procedure. In the case of parallel processing, the sample is divided and routed to the individual chambers for titration.

The devices for separation and titration may be independent physical entities or, in the case of a small footprint titration device, the chambers may be integrated into a single device with a layered 3-dimensional structure. FIG. 40 presents a conceptual view of an integrated unit 780 comprising a DFGF device 781 and a pair of isoelectric point determination devices in accordance with any of the aspects and embodiments disclosed herein, 782 and 783. The DFGF device includes an electrode chamber 784 and a separation chamber 785 separated by permeable material 790. Isoelectric point determination devices 782 and 783 comprise titration chambers 786 and 787 and electrode chambers 788 and 789, each separated by permeable material 791 and 792. The permeable materials 790, 791 and 792 may be the same as or different from each other as desired, although advantageously the permeable materials 791 and 792 used in the isoelectric point determination devices are the same. The particular details of the devices are omitted. The chamber are offset from each other in the device to allow for thru-chamber visualization, if desired.

In certain preferred embodiments, the analyte(s) of interest are separated and focused and the isoelectric point of the analyte(s) is determined in accordance with any of the devices and methods provided above. Advantageously, the sample is flowed from the device used to determine the isoelectric point directly into the device which will determine the molecular weight, as in for example a microfluidic system in which the separation and focusing device, isoelectric point determining device, and molecular weight determining device are each on interconnectable chips. Multiple charged analytes in certain preferred embodiments can be separated on a DFGF device, optionally a DFGF device in which molecular sieve, operative to shift the location at which each stationary focused band of charged analyte forms under the focusing process parameters, is incorporated in the separation chamber, to fractionate or separate the multiple charged analytes into each of the component charged analytes. Each of the multiple charged analytes can then be individually eluted and the isoelectric point can be determined by any of the methods and devices disclosed herein. Optionally, the charged analytes are not eluted from the DFGF device, and instead the isoelectric points are determined directly in the DFGF chamber. Other steps generally would be necessary once the analyte(s) had been focused into separate bands. Suitable techniques for determining molecular weight are known and will be readily apparent to those skilled in the art in view of the present disclosure, such as, for example, mass spectroscopy, particularly MALDI-MS. Other suitable molecular weight devices and configurations of systems comprising the separation and isolation, isoelectric point determination, molecular weight determination devices and other desirable devices will be readily apparent to those of skill in the art, given the benefit of the present disclosure.

In certain preferred embodiments, the isoelectric point and the molecular weight of a charged analyte can be configured or displayed as desired. For example, a two-dimensional display of the molecular weights vs. isoelectric points can be developed. A fractionated or separated sample, for example a biomacromolecules such as a protein or a DNA sample, can be analyzed and a "virtual" 2D-PAGE plot of the sample can be developed. The plot is virtual in the sense that it is composed of data points, whereas the typical 2D-PAGE results comprise the fractionated sample itself on an electrophoresis plate. Other suitable data manipulations will be readily apparent to those of ordinary skill in the art, given the benefit of the present disclosure.

In certain preferred embodiments of the devices herein presented, the second or electrode chamber need not include an inlet and an outlet and instead can be a sealed chamber, in the sense that nothing passes into or out of the chamber except through the permeable material. Other embodiments may not have a second chamber at all, and instead have the electrodes located in the first chamber. In such embodiments, the electrodes are preferably shielded from the analyte, by a permeable membrane or other suitable shielding material, which may shield the electrodes as a single sheet or instead may optionally coat each electrode. Other suitable configurations will be readily apparent to those of ordinary skill in the art, given the benefit of the present disclosure.

Figure 42:
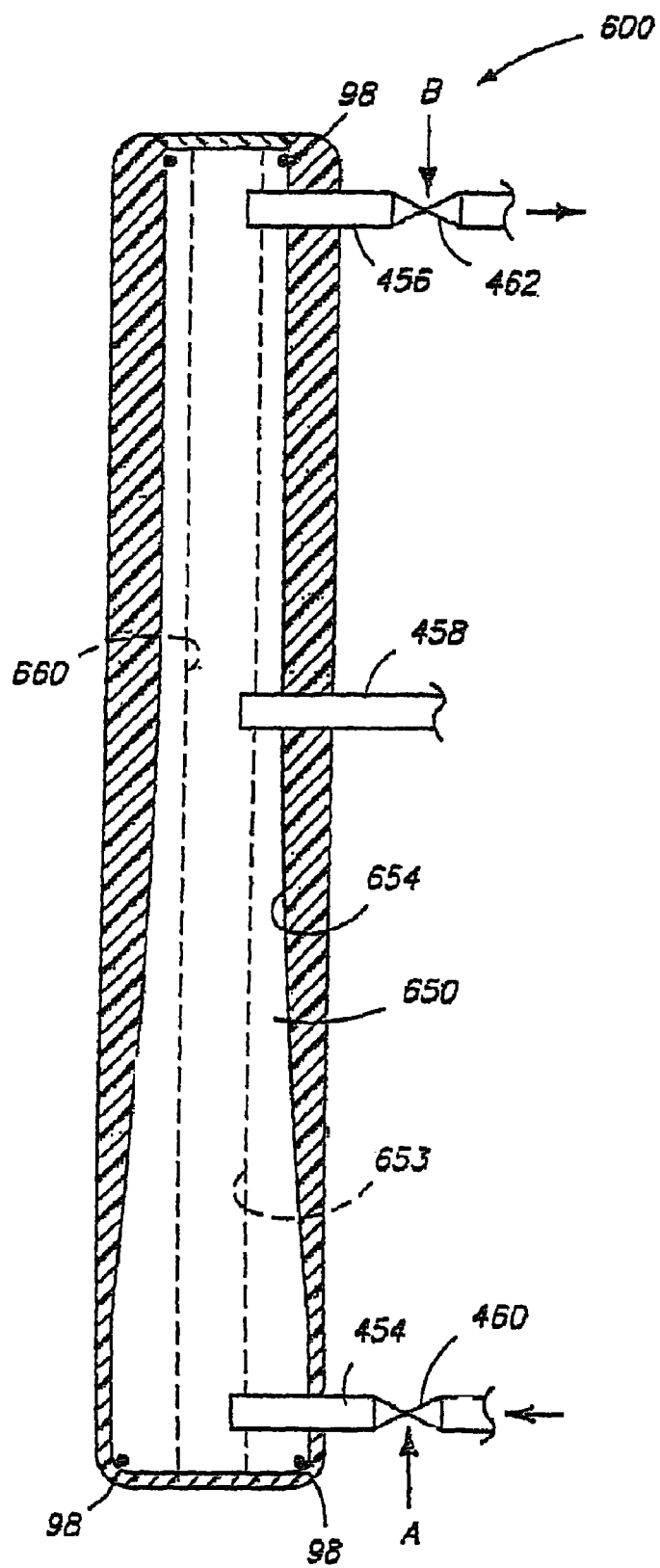
FIG. 42 is a diagrammatic sectional view of a representative device.

FIG. 42 illustrates another preferred embodiment. Device 600 includes electrode chamber 650 having a varying cross-sectional area defined by electrode chamber walls 654. Positioned within the electrode chamber is a permeable conduit membrane 660, which defines separation chamber 653. The separation chamber 653 is encircled longitudinally by the electrode chamber 650. As illustrated in FIG. 42, permeable membrane 660 is uniform cross-sectionally such that the fluid velocity within the separation chamber is uniform. In certain preferred embodiments the membrane 660, and thereby the separation chamber 653, is tubular, preferably cylindrically tubular. In other preferred embodiments, the separation chamber can be non-tubular, i.e., can be some other geometry, and can be non-uniform cross-sectionally. Membrane 660 is in certain preferred embodiments a dialysis membrane. Sample fluid flows into the separation chamber 653 through inlet port 454, and exits the chamber through outlet port 456. Valves 460 and 462 are provided in-line with inflow and outflow ports 454 and 456, respectively. These valves are operably connected via control signals A and B to a controller, which can be manually controlled or can be computer-controlled as desired. The valves can thus be opened or closed, either fully or partially, to govern the flow rate and volume of fluid introduced into the chamber. An additional port 458 is located intermediate the inlet and outlet ports of the separation chamber and permits the removal or addition of fluid to or from the separation chamber. For example, a focused band of charged analyte could be brought under the additional port and the analyte band could be extracted through the port, for example, by any of the means identified herein. Of course, more than one such additional port could be incorporated. Device 600 further includes electrodes 98, which in certain preferred embodiments are annular, located at proximate ends of the electrode chamber 650, preferably adjacent electrode chamber walls 654 and thus remote from the membrane 660. The converging walls 654 of the electrode chamber 650 cause the current density of electrical current flowing between electrodes 98 to concentrate toward the converging upper end to create a gradient in the electric field within the separation chamber.

While various preferred embodiments of the methods and devices have been illustrated and described, it will be appreciated that various modifications and additions can be made to such embodiments without departing from the spirit and scope of the methods and devices as defined by the following claims.

We claim:

1. A method of determining the isoelectric point of a charged analyte comprising: focusing a charged analyte in a flowing liquid in an electric field gradient to form in the flowing liquid a focused band of the charged analyte at a first stable position in the electric field gradient; changing the pH of the flowing liquid at least once by an amount sufficient to change the position of the focused band of the charged analyte within the electric field gradient to a second stable position in the electric field gradient; obtaining pH and corresponding position data for the charged analyte, comprising determining the pH of the flowing liquid and the corresponding position of the focused band of the charged analyte at a plurality of band positions within the electric field gradient; and determining the isoelectric point of the charged analyte based on the pH and corresponding position data.

2. The method of claim 1, wherein the isoelectric point is determined by extrapolation.

3. The method of claim 1, wherein the pH is incremented to a plurality of pH's above the isoelectric point of the charged analyte and to a plurality of pH's below the isoelectric point of the charged analyte.

4. The method of claim 3, wherein the isoelectric point is determined by interpolation.

5. The method of claim 1, wherein the pH of the flowing liquid is incremented by mixing the flowing liquid with a titrating solution.

6. The method of claim 1, wherein the pH of the flowing liquid is incremented by dialyzing ions from a titrating solution into the flowing liquid.

7. The method of claim 3, wherein the pH is incremented from above the isoelectric point downward until an upper bracketing pH at which the charged analyte elutes is reached;

the pH is incremented from below the isoelectric point upward until a lower bracketing pH at which the charged analyte elutes;

the upper bracketing pH and the lower bracketing pH are obtained; and the isoelectric point is determined by averaging the upper bracketing pH and the lower bracketing pH.

8. The method of claim 1, wherein the charged analyte is first focused in a DFGF chamber.

9. The method of claim 8, wherein the DFGF chamber comprises a separation chamber which comprises molecular sieve operative to shift the location at which each stationary focused band of charged analyte forms under the focusing process parameters.

10. The method of claim 1, wherein the charged analyte comprises a biomacromolecules.

11. The method of claim 10, wherein the biomacromolecules comprises protein.

12. The method of claim 10, wherein the biomacromolecules comprises DNA.

13. The method of claim 1, wherein the charged analyte comprises multiple charged analytes.

14. The method of claim 7, wherein an analyte band detector is used to sense elution of the charged analyte.

15. The method of claim 7, wherein the sample is split and portions of the sample are separately focused and incremented.

16. The method of claim 1, wherein the pH is determined by calculation from mixing a known amount of a titrating solution of known pH with a known amount of a flowing liquid of known pH.

17. The method of claim 1, wherein the charged analyte is first focused in an EFGF chamber.

18. The method of claim 17, wherein the EFGF chamber comprises a separation chamber which comprises molecular sieve operative to shift the location at which each stationary focused band of charged analyte forms under the focusing process parameters.

19. The method of claim 17, wherein the EFGF chamber comprises a configured electrode chamber.

20. The method of claim 17, wherein the EFGF chamber comprises a configured separation chamber.

* * * * *